(12) United States Patent
Rowlands et al.

(10) Patent No.: US 10,450,701 B2
(45) Date of Patent: Oct. 22, 2019

(54) PULPING LIQUORS AND USES THEREOF

(71) Applicants: Licella Pty Ltd, Somersby (AU);
Canfor Pulp Ltd, Vancouver (CA)

(72) Inventors: William Rowlands, Alexandria (AU);
Leonard James Humphreys, Roseville Chase (AU); Robert Downie, Laguna (AU); Paul Watson, Vancouver (CA)

(73) Assignees: Licella Pty Ltd, Somersby (AU);
Canfor Pulp Ltd, Vancouver (CA)

( * ) Notice: Subject to any disclaimer, the term of this patent is extended or adjusted under 35 U.S.C. 154(b) by 0 days.

(21) Appl. No.: 15/486,785

(22) Filed: Apr. 13, 2017

(65) Prior Publication Data

US 2017/0218287 A1 Aug. 3, 2017
US 2017/0369802 A2 Dec. 28, 2017

Related U.S. Application Data

(63) Continuation of application No. PCT/AU2015/000617, filed on Oct. 15, 2015.

(30) Foreign Application Priority Data

Oct. 15, 2014 (AU) ................................. 2014904129

(51) Int. Cl.
*D21C 11/00* (2006.01)
*C12P 7/08* (2006.01)
(Continued)

(52) U.S. Cl.
CPC .......... *D21C 11/0007* (2013.01); *C07C 29/88* (2013.01); *C07C 41/44* (2013.01);
(Continued)

(58) Field of Classification Search
CPC ............................. D21C 11/0007; C10G 1/00
See application file for complete search history.

(56) References Cited

U.S. PATENT DOCUMENTS

| 4,347,220 A | 8/1982 | Nelson et al. |
| 4,381,035 A | 4/1983 | Hradel |
(Continued)

FOREIGN PATENT DOCUMENTS

| WO | 99/07936 | 2/1999 | |
| WO | WO-0052256 A1 * | 9/2000 | ............. D21B 1/021 |
(Continued)

OTHER PUBLICATIONS

Authorized Officer, Asoka Dias-Abey, Australian Patent Office, International Search Report, International Application No. PCT/AU2015/000617, 5 pages, dated Dec. 22, 2015.
(Continued)

*Primary Examiner* — Ellen M McAvoy
*Assistant Examiner* — Ming Cheung Po
(74) *Attorney, Agent, or Firm* — Sunstein Kann Murphy & Timbers LLP

(57) ABSTRACT

The present invention relates generally to the generation of bio-products from organic matter feedstocks. More specifically, the present invention relates to the use of pulping liquors in the hydrothermal/thermochemical conversion of lignocellulosic and/or fossilised organic feedstocks into biofuels (e.g. bio-oils) and/or chemical products (e.g. platform chemicals).

18 Claims, 2 Drawing Sheets

(51) Int. Cl.
*C10L 1/02* (2006.01)
*D21C 3/02* (2006.01)
*D21C 3/20* (2006.01)
*C10G 1/00* (2006.01)
*C10G 1/04* (2006.01)
*C10L 3/00* (2006.01)
*C10G 1/08* (2006.01)
*C10G 1/10* (2006.01)
*C10G 3/00* (2006.01)
*C07C 29/88* (2006.01)
*C07C 41/44* (2006.01)
*C07C 45/85* (2006.01)
*C10L 5/44* (2006.01)
*C10L 5/48* (2006.01)

(52) U.S. Cl.
CPC .............. *C07C 45/85* (2013.01); *C10G 1/00* (2013.01); *C10G 1/04* (2013.01); *C10G 1/086* (2013.01); *C10G 1/10* (2013.01); *C10G 3/00* (2013.01); *C10L 1/02* (2013.01); *C10L 3/00* (2013.01); *C10L 5/442* (2013.01); *C10L 5/48* (2013.01); *C12P 7/08* (2013.01); *D21C 3/02* (2013.01); *D21C 3/20* (2013.01); *C10G 2300/1003* (2013.01); *C10G 2300/1014* (2013.01); *C10L 2200/0469* (2013.01); *C10L 2290/06* (2013.01); *C10L 2290/24* (2013.01); *C10L 2290/544* (2013.01); *C10L 2290/547* (2013.01); *Y02E 50/10* (2013.01); *Y02E 50/14* (2013.01); *Y02E 50/30* (2013.01); *Y02E 50/32* (2013.01); *Y02P 20/582* (2015.11); *Y02P 30/20* (2015.11)

(56) References Cited

U.S. PATENT DOCUMENTS

| | | | |
|---|---|---|---|
| 5,019,135 A | 5/1991 | Sealock, Jr. et al. | |
| 7,262,331 B2 * | 8/2007 | van de Beld | C10G 1/00 585/240 |
| 8,003,833 B2 * | 8/2011 | Appel | B01D 3/009 585/240 |
| 2004/0079498 A1 * | 4/2004 | Haaslahti | D21C 3/02 162/19 |
| 2006/0096163 A1 | 5/2006 | Dickinson et al. | |
| 2011/0232162 A1 | 9/2011 | Siskin et al. | |
| 2011/0275869 A1 | 11/2011 | Prochazka et al. | |
| 2012/0152836 A1 * | 6/2012 | Powell | C07G 1/00 210/620 |

FOREIGN PATENT DOCUMENTS

| | | | |
|---|---|---|---|
| WO | WO 2002/20699 A1 | 3/2002 | ............ C10G 1/00 |
| WO | 2004/087619 | 10/2004 | |
| WO | WO-2004087619 A2 * | 10/2004 | ............ C02F 11/18 |
| WO | 2006/053020 | 5/2006 | |
| WO | 2009/028969 | 3/2009 | |
| WO | 2011/138633 | 11/2011 | |
| WO | WO 2012/000033 A1 | 1/2012 | ............ C10G 1/04 |
| WO | 2012/047832 | 4/2012 | |
| WO | 2012/175796 | 12/2012 | |
| WO | WO-2012175796 A1 * | 12/2012 | ............ C10G 2/00 |
| WO | WO 2016/058031 A1 | 4/2016 | ............ C10L 1/00 |

OTHER PUBLICATIONS

Authorized Officer, Asoka Dias-Abey, Australian Patent Office, Written opinion of the International Searching Authority, International Application No. PCT/AU2015/000617, 4 pages, dated Dec. 22, 2015.

* cited by examiner

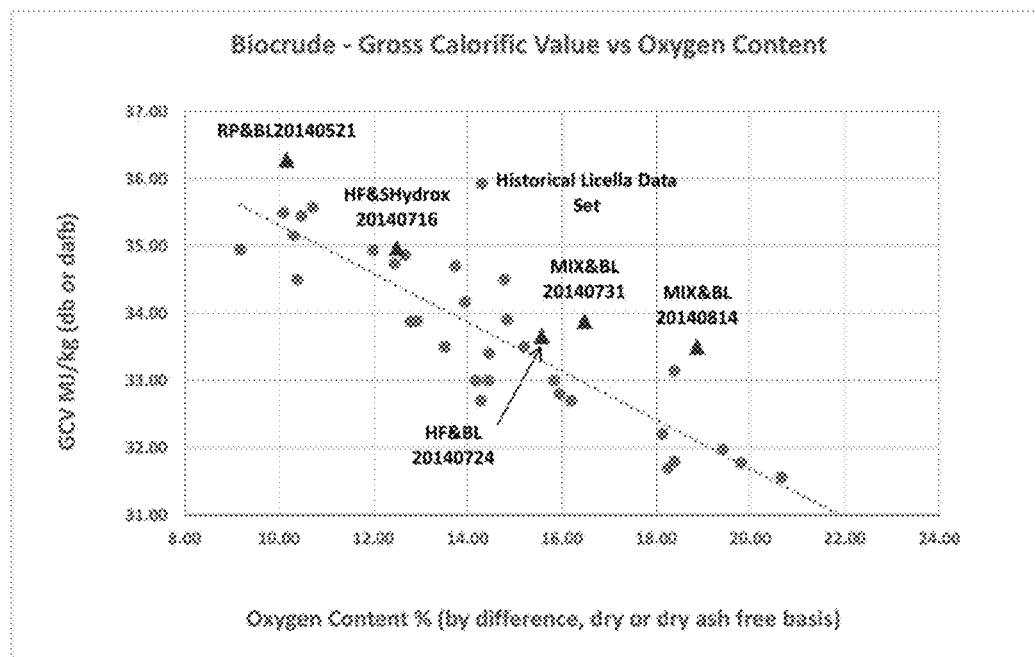
FIGURE ONE

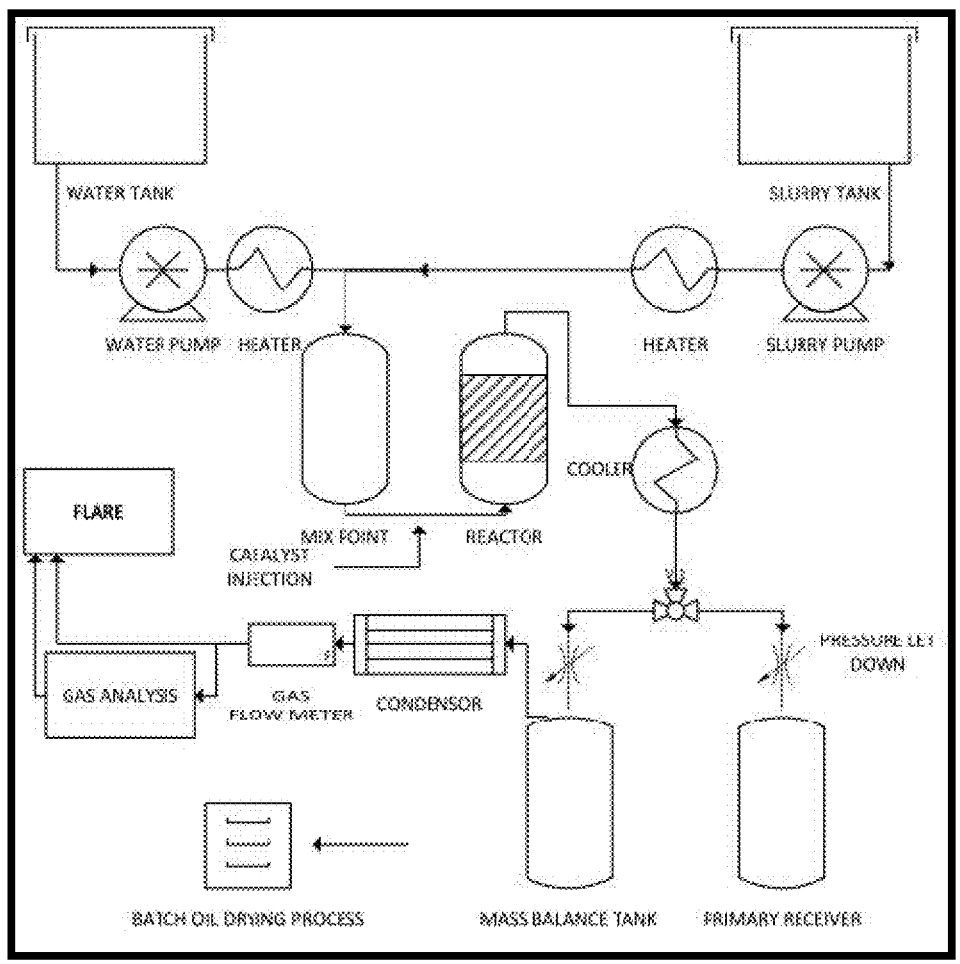
FIGURE TWO

PULPING LIQUORS AND USES THEREOF

CROSS-REFERENCE TO RELATED APPLICATIONS

This application is a continuation of International Patent Application No. PCT/AU2015/000617, filed on Oct. 15, 2015, designating the United States of America, which derives priority from Australian provisional patent application number 2014904129, filed on Oct. 15, 2014. Each of the above-referenced applications is incorporated by reference herein in its entirety.

TECHNICAL FIELD

The present invention relates generally to the generation of bio-products from organic matter feedstocks. More specifically, the present invention relates to the use of pulping liquors in the hydrothermal/thermochemical conversion of lignocellulosic and/or fossilised organic feedstocks into bio-fuels (e.g. bio-oils) and/or chemical products (e.g. platform chemicals).

BACKGROUND

The global demand for energy continues to rise while reserves of conventional petroleum (e.g. oil, gas, and natural gas liquids) are in decline. This has led to increased focus and research into unconventional fuel resources (e.g. heavy oil, oil sands, oil shale) and other non-fossil sources of energy (e.g. lignocellulosic materials).

A significant amount of research in the field of "alternative" energy production has focussed on the generation of biofuels from lignocellulosic matter. This technology raises the prospect of a shift to an abundant and renewable feedstock for energy production as an alternative to the depleting reserves of hydrocarbon-based raw materials. The enrichment of low energy density fossil fuels (e.g. lignite, peat and oil shale) into high energy fuel products also represents an attractive alternative given the relative abundance of those resources.

In particular, the thermochemical conversion of biomass and other complex organic matter into biofuels and chemicals based on hydrothermal reactions has shown significant promise. Gasification processes are generally conducted at higher temperatures (e.g. 400° C.-700° C.) and can produce methane or hydrogen gases in high yields. Liquefaction processes are generally conducted at lower temperatures (e.g. 200° C.-400° C.) and produce liquid products referred to in the field as "bio-oil" or "bio-crude". To provide a viable replacement or supplement to existing fossil fuels, bio-oils generated from these and related technologies need characteristics (e.g. high energy/yield, low oxygen/water content, reduced viscosity) approximating those of crude oils. Additionally, it is highly important for processes of this nature to be cost-efficient for economic feasibility.

Numerous modifications to improve thermochemical processes for bio-oil production have been developed. For example, the prior removal of hemicellulose under mild conditions from plant materials can improve the production of bio-oils from lignocellulosic feedstocks (see PCT publication No. WO 2010/037178). It has also been demonstrated that rather than gradually heating feedstock slurry to reaction temperature, contacting the slurry with an already supercritical solvent can provide advantageous effects in bio-oil production (see PCT publication No. WO 2012/000033). Incorporating oil into a feedstock slurry, which may also be a recycled bio-oil product, has been shown to improve process efficiency and product characteristics (see PCT publication No. WO 2012/092644). The inclusion of a solid substrate in organic matter feedstock used in thermochemical conversion processes has been shown to reduce scaling and/or reduce the development of pressure differentials during treatment (see PCT application No. PCT/AU2014/00601). Despite these advances, new modifications to thermochemical processes capable of increasing process efficiency, lowering costs and/or improving product characteristics are still desirable.

Many if not most processes for the thermochemical conversion of biomass into biofuels utilise catalysts to increase process efficiency and/or improve product characteristics. A wide range of catalysts have been used in these processes (see, for example, PCT publication No. WO 2011/123897) and the identification of appropriate catalyst combinations and/or alternative sources of catalysts provides an opportunity to improve existing bio-oil production methods.

SUMMARY OF THE INVENTION

The present inventors have unexpectedly identified that pulping liquors such as black liquor can be used as an effective source of catalysts to facilitate the efficient thermochemical conversion of biomass into biofuels. In view of its organic content (e.g. cellulosic matter) pulping liquors also provide a source of additional feedstock material capable of conversion into bio-products, which can in turn provide a cost benefit by reducing the amount of feedstock material required.

In a first aspect, the present invention provides a method for producing a bio-product from organic matter feedstock, the method comprising:

providing a reaction mixture comprising the organic matter feedstock, a solvent, and pulping liquor;

treating the reaction mixture in a reactor vessel at a reaction temperature and pressure suitable for conversion of all or a portion of the organic matter feedstock into a product mixture comprising the bio-product; and depressurising and cooling the product mixture;

wherein the reaction mixture and product mixture move in continuous flow through reactor vessel during said treating.

In one embodiment, the organic matter feedstock is lignocellulosic feedstock.

In one embodiment, the organic matter feedstock is coal feedstock (e.g. lignite feedstock).

In one embodiment, the organic matter feedstock and the pulping liquor are both black liquor.

In one embodiment, the pulping liquor is black liquor and the organic matter feedstock is not a pulping liquor.

In one embodiment, the organic matter feedstock and the pulping liquor both comprise or consist of black pulping liquor (black liquor).

In one embodiment, the pulping liquor comprises or consists of black liquor and the organic matter feedstock does not comprise or consist of pulping liquor.

In one embodiment, the pulping liquor is black liquor.

The black liquor may have been separated from pulp following a chemical pulping process in which a wood feedstock has been digested with pulping chemicals under heat and pressure.

The black liquor may comprise between about 2.5 and 7.0 weight % sodium hydroxide (NaOH) on dry black liquor solids (DBLS), between about 0.06 and 3.0 wt % sodium sulfide ($Na_2S$), between about 4.5 and about 16.0 wt % sodium carbonate ($Na_2CO_3$), between about 0.5 g/l and about 5 g/l sodium sulfite ($Na_2SO_3$), between about 1.9 and about 16.6 wt. % sodium sulfate ($Na_2SO_4$), between about 2.4 and about 7.5 wt. % sodium thiosulfate ($Na_2S_2O_3$), and between about 50 and about 70 wt. % organic solids on dry black liquor solids.

The black liquor may comprise between about 0.5 g/l and 2.5 g/l sodium hydroxide (NaOH), between about 2.5 g/l and 6.0 g/l sodium sulfide ($Na_2S$), between about 5 g/l and about 10 g/l sodium carbonate ($Na_2CO_3$), between about 0.5 g/l and about 5 g/l sodium sulfite ($Na_2SO_3$), between about 0.5 g/l and about 5 g/l sodium sulfate ($Na_2SO_4$), between about 1.0 g/l and about 6 g/l sodium thiosulfate ($Na_2S_2O_3$), and between about 10 g/l and about 100 g/l organic solids.

The black liquor may comprise between about 1.0 g/l and 2.0 g/l sodium hydroxide (NaOH), between about 3.5 g/l and 5.5 g/l sodium sulfide ($Na_2S$), between about 6.5 g/l and about 9.0 g/l sodium carbonate ($Na_2CO_3$), between about 1.0 g/l and about 3.0 g/l sodium sulfite ($Na_2SO_3$), between about 2.0 g/l and about 4 g/l sodium sulfate ($Na_2SO_4$), between about 2.0 g/l and about 4.5 g/l sodium thiosulfate ($Na_2S_2O_3$), and between about 20 g/l and about 50 g/l organic solids.

The black liquor may comprise between about 4 wt % and 10 wt % sodium hydroxide (NaOH), between about 10 wt % and 30 wt % sodium sulfide ($Na_2S$), between about 25 wt % and about 50 wt % sodium carbonate ($Na_2CO_3$), between about 5 wt % and about 15 wt % sodium sulfite ($Na_2SO_3$), between about 8 wt % and about 20 wt % sodium sulfate ($Na_2SO_4$), between about 10 wt % and about 25 wt % sodium thiosulfate ($Na_2S_2O_3$), and between about 10 wt % and about 90 wt % organic solids or between about 30% and about 70% organic solids.

The black liquor may comprise between about 5 wt % and 9 wt % sodium hydroxide (NaOH), between about 15 wt % and 25 wt % sodium sulfide ($Na_2S$), between about 25 wt % and about 45 wt % sodium carbonate ($Na_2CO_3$), between about 5 wt % and about 15 wt % sodium sulfite ($Na_2SO_3$), between about 10 wt % and about 15 wt % sodium sulfate ($Na_2SO_4$), between about 13 wt % and about 20 wt % sodium thiosulfate ($Na_2S_2O_3$), and between about 40 wt % and about 90 wt % organic solids or between about 50% and about 80% organic solids, or between about 60% and about 75% organic solids.

The black liquor may comprise any one or more of inorganic elements, dissolved wood substances, acetic acid, formic acid, sugars, caboxylic acids, xylans, and methanol.

In one embodiment, the pulping liquor is a green pulping liquor (green liquor).

The green liquor may comprise between about 9 g/l and 20 g/l sodium hydroxide (NaOH), between about 25 g/l and 55 g/l sodium sulfide ($Na_2S$), between about 80 g/l and about 145 g/l sodium carbonate ($Na_2CO_3$), between about 4.0 g/l and about 8.0 g/l sodium sulfite ($Na_2SO_3$), between about 6.0 g/l and about 15.0 g/l sodium sulfate ($Na_2SO_4$), and between about 3.0 g/l and about 9.0 g/l sodium thiosulfate ($Na_2S_2O_3$).

The green liquor may be obtained by processing the black liquor. The green liquor may be obtained by burning the black liquor in an oxygen deficient environment and dissolving the resultant material in a solvent (e.g. water). The concentration of organic solids in the black liquor may be increased prior to burning the black liquor in the oxygen deficient environment to obtain the green liquor. Concentration of the organic solids in the black liquor may be achieved by evaporation.

The green liquor may comprise between about 11 g/l and 20 g/l sodium hydroxide (NaOH), between about 25 g/l and 50 g/l sodium sulfide ($Na_2S$), between about 80 g/l and about 130 g/l sodium carbonate ($Na_2CO_3$), between about 4.0 g/l and about 8.0 g/l sodium sulfite ($Na_2SO_3$), between about 8.0 g/l and about 15.0 g/l sodium sulfate ($Na_2SO_4$), and between about 3.0 g/l and about 9.0 g/l sodium thiosulfate ($Na_2S_2O_3$).

The green liquor may comprise between about 13 g/l and 18 g/l sodium hydroxide (NaOH), between about 30 g/l and 45 g/l sodium sulfide ($Na_2S$), between about 95 g/l and about 120 g/l sodium carbonate ($Na_2CO_3$), between about 5.0 g/l and about 7.0 g/l sodium sulfite ($Na_2SO_3$), between about 9.0 g/and about 13.0 g/l sodium sulfate ($Na_2SO_4$), and between about 4.0 g/l and about 7.0 g/l sodium thiosulfate ($Na_2S_2O_3$).

The green liquor may comprise between about 4 wt % and 12 wt % sodium hydroxide (NaOH), between about 15 wt % and 25 wt % sodium sulfide ($Na_2S$), between about 50 wt % and about 70 wt % sodium carbonate ($Na_2CO_3$), between about 1 wt % and about 7 wt % sodium sulfite ($Na_2SO_3$), between about 2 wt % and about 10 wt % sodium sulfate ($Na_2SO_4$), and between about 1 wt % and about 5 wt % sodium thiosulfate ($Na_2S_2O_3$).

The green liquor may comprise between about 5 wt % and 10 wt % sodium hydroxide (NaOH), between about 17 wt % and 23 wt % sodium sulfide ($Na_2S$), between about 55 wt % and about 65 wt % sodium carbonate ($Na_2CO_3$), between about 1 wt % and about 4 wt % sodium sulfite ($Na_2SO_3$), between about 3 wt % and about 9 wt % sodium sulfate ($Na_2SO_4$), and between about 1 wt % and about 5 wt % sodium thiosulfate ($Na_2S_2O_3$).

In one embodiment, the pulping liquor is a white pulping liquor (white liquor).

The white liquor may be obtained by processing the green liquor. The white liquor may be obtained by reacting the green liquor with lime or a derivative thereof (e.g. calcium oxide (CO), calcium hydroxide (CaOH)).

The white liquor may comprise between about 80 g/l and 110 g/l sodium hydroxide (NaOH), between about 30 g/l and 45 g/l sodium sulfide ($Na_2S$), between about 18 g/l and about 35 g/l sodium carbonate ($Na_2CO_3$), between about 3.0 g/l and about 6.0 g/l sodium sulfite ($Na_2SO_3$), between about 7.0 g/l and about 12.0 g/l sodium sulfate ($Na_2SO_4$), and between about 3.0 g/l and about 9.0 g/l sodium thiosulfate ($Na_2S_2O_3$).

The white liquor may comprise between about 85 g/l and 105 g/l sodium hydroxide (NaOH), between about 32 g/l and 43 g/l sodium sulfide ($Na_2S$), between about 20 g/l and about 30 g/l sodium carbonate ($Na_2CO_3$), between about 3.5 g/l and about 5.5 g/l sodium sulfite ($Na_2SO_3$), between about 8.0 g/l and about 10.0 g/l sodium sulfate ($Na_2SO_4$), and between about 4.5 g/l and about 7.5 g/l sodium thiosulfate ($Na_2S_2O_3$).

The white liquor may comprise between about 40 wt % and 65 wt % sodium hydroxide (NaOH), between about 10 wt % and 30 wt % sodium sulfide ($Na_2S$), between about 8 wt % and about 22 wt % sodium carbonate ($Na_2CO_3$), between about 1 wt % and about 6 wt % sodium sulfite ($Na_2SO_3$), between about 2 wt % and about 10 wt % sodium sulfate ($Na_2SO_4$), and between about 1 wt % and about 5 wt % sodium thiosulfate ($Na_2S_2O_3$).

The white liquor may comprise between about 45 wt % and 60 wt % sodium hydroxide (NaOH), between about 15 wt % and 25 wt % sodium sulfide ($Na_2S$), between about 10 wt % and about 20 wt % sodium carbonate ($Na_2CO_3$), between about 2 wt % and about 5 wt % sodium sulfite ($Na_2SO_3$), between about 2 wt % and about 7 wt % sodium sulfate ($Na_2SO_4$), and between about 1.5 wt % and about 4 wt % sodium thiosulfate ($Na_2S_2O_3$).

In one embodiment, the treating comprises treating the reaction mixture at a temperature of between 250° C. and 450° C., and a pressure of between 100 bar and 300 bar.

The treating may comprise heating the slurry to a temperature selected from the group consisting of at least about 250° C., at least about 300° C., at least about 350° C., at least about 370° C., at least about 390° C., at least about 400° C., between about 200° C. and about 400° C., between about 200° C. and about 400° C., between about 300° C. and about 400° C., between about 350° C. and about 400° C., and between about 370° C. and about 450° C.

The treating may comprise pressurising the reaction mixture at a pressure of between about 100 bar and about 400 bar, between about 150 bar and about 400 bar, between about 200 bar and about 400 bar, between about 150 bar and about 350 bar, between about 180 bar and about 350 bar, between about 150 bar and about 300 bar, between about 150 bar and about 280 bar, between about 150 bar and about 270 bar, or between about 200 bar and about 300 bar.

The treating may comprise treating the reaction mixture at a temperature of between 310° C. and 360° C., and a pressure of between 160 bar and 250 bar.

The treating may comprise treating the reaction mixture at a temperature of between 320° C. and 360° C., and a pressure of between 220 bar and 250 bar.

The treating may comprise treating the reaction mixture at:
(i) a temperature of between 200° C. and 450° C., and a pressure of between 100 bar and 300 bar;
(ii) a temperature of between 250° C. and 350° C., and a pressure of between 140 bar and 240 bar.

In one embodiment, the method comprises preparing a slurry comprising the organic matter and the pulping liquor, generating subcritical or supercritical steam independently of the slurry, and contacting the slurry with the subcritical or supercritical steam in at least one vessel or chamber of said reactor vessel.

The slurry may comprise lignocellulosic feedstock, coal (e.g. lignite), or a combination thereof.

The slurry may be at ambient or near ambient temperature and pressure prior to the contacting with the subcritical or supercritical steam.

The treating may comprise heating the slurry to a temperature selected from the group consisting of at least about 100° C., at least about 150° C., at least about 200° C., at least about 250° C., at least about 300° C., at least about 350° C., between about 200° C. and about 250° C., between about 200° C. and about 400° C., between about 250° C. and about 400° C., between about 250° C. and about 350° C., and between about 250° C. and about 350° C.; generating subcritical or supercritical steam independently of the slurry; and contacting the slurry with the subcritical or supercritical steam in at least one vessel or chamber of the reactor vessel.

The slurry may be pressurised prior to and/or after said contacting.

In one embodiment, the method comprises preparing a slurry comprising the organic matter, heating the slurry to a temperature of between at least about 100° C., at least about 150° C., at least about 200° C., at least about 250° C., at least about 300° C., at least about 350° C., between about 200° C. and about 250° C., between about 200° C. and about 400° C., between about 250° C. and about 400° C., between about 250° C. and about 350° C., and between about 250° C. and about 350° C.; mixing the pulping liquor with the slurry after heating the slurry to said temperature; and contacting the slurry comprising the lignocellulosic feedstock and black liquor with subcritical or supercritical steam in at least one vessel or chamber of the reactor vessel, wherein the subcritical or supercritical steam is generated independently of the slurry.

The slurry may comprise lignocellulosic feedstock, coal (e.g. lignite), or a combination thereof.

In one embodiment, the method comprises a first preheating stage in which the reaction mixture is heated to a temperature that is below the reaction temperature, and a second heating stage in which the reaction mixture is heated to the reaction temperature.

The second heating stage may comprise contacting the reaction mixture with subcritical or supercritical steam.

In one embodiment, the pulping liquor is mixed with the feedstock and/or solvent prior to the treating.

In one embodiment the pulping liquor is added to the reaction mixture after the reaction mixture reaches said reaction temperature and pressure.

In one embodiment the reaction mixture comprises between 1% and 30%, between 5% and 30%, between 10% and 30%, between 5% and 30%, between 5% and 20%, between 5% and 15%, between 10% and 30%, between 10% and 30%, between 10% and 15%, less than 20%, less than 30%, less than 25%, less than 15%, less than 10%, or less than 5%, of the pulping liquor by weight.

In one embodiment the reaction mixture comprises between 1% and 100%, between 90% and 100%, between 95% and 100%, between 50% and 100%, between 50% and 90%, between 50% and 95%, between 50% and 95%, between 50% and 80%, between 50% and 70%, between 50% and 60%, between 30% and 90%, between 40% and 90%, or between 20% and 75%, of the pulping liquor by weight.

In one embodiment, the reaction mixture comprises less than 20%, less than 30%, less than 35%, less than 40%, less than 40%, less than 70%, less than 80%, less than 90%, less than 95%, between 10% and 95%, between 30% and 95%, between 50% to 70%, or between 60% to 80%, of the solvent by weight.

In one embodiment, the solvent is an aqueous solvent, an oil solvent, or a mixture of an aqueous solvent and an oil solvent.

The oil solvent or the mixture of the aqueous solvent and the oil solvent may comprise crude tall oil, distilled tall oil, or a combination thereof.

The aqueous solvent may comprise water, water only, or water and an alcohol.

The aqueous solvent may comprise water and an alcohol, and the alcohol may be selected from ethanol, methanol, or a combination of methanol and ethanol.

The reaction mixture may comprise a percentage by weight of the alcohol of more than 3%, more than 5%, more than 10%, more than 15%, more than 20%, more than 25%, more than 30%, less than 30%, less than 25%, less than 20%, less than 15%, less than 10%, less than 5%, or less than 3%.

In one embodiment, the lignocellulosic feedstock may be lignocellulosic matter comprising at least 10% lignin, at least 35% cellulose, and at least 20% hemicellulose.

The lignocellulosic feedstock may comprise more than about 10% of each of lignin, cellulose, and hemicellulose.

In one embodiment, the reaction mixture comprises more than 10%, more than 15%, more than 20%, more than 30%, more than 35%, or more than 40%, of the organic matter by weight.

The organic matter may be lignocellulosic feedstock, coal (e.g. lignite), or a combination thereof.

In one embodiment, the reaction mixture comprises less than 10%, less than 15%, less than 20%, less than 30%, less than 35%, less than 40%, less than 50%, between 5% and 40%, between 10% to 35%, or between 15% and 30%, of the organic matter by weight.

The organic matter may be lignocellulosic feedstock, coal (e.g. lignite), or a combination thereof.

In one embodiment, the organic matter is provided in the form of a slurry comprising some or all of the solvent.

The organic matter may be lignocellulosic feedstock, coal (e.g. lignite), or a combination thereof.

The organic matter may be provided in the form of a slurry comprising some or all of the solvent and/or some or all of the pulping liquor.

The treating may comprise treating the organic matter, the solvent, and the pulping liquor in the form of a slurry with a flow velocity of above 0.01 cm/s, above 0.05 cm/s, above 0.5 cm/s, above 0.1 cm/s, above 1.5 cm/s, or above 2.0 cm/s.

In one embodiment, the reaction mixture is subjected to:
(a) heating and pressurisation to a target temperature and pressure,
(b) treatment at target temperature(s) and pressure(s) for a defined time period (i.e. the "retention time"), and
(c) cooling and de-pressurisation,
under continuous flow conditions.

In one embodiment, the treating is for a time period of between about 20 minutes and about 30 minutes.

In one embodiment, the method comprises the step of heating the organic matter feedstock (e.g. lignocellulosic feedstock, coal (e.g. lignite), or a combination thereof) and solvent to the temperature in a time period of less than about 2 minutes, prior to the treating.

In one embodiment, the method comprises the step of heating and pressurising the organic matter feedstock (e.g. lignocellulosic feedstock, coal (e.g. lignite), or a combination thereof) and solvent to the temperature and pressure in a time period of less than about 2 minutes, prior to the treating.

In one embodiment, the method comprises the steps of:
(i) cooling the product mixture to a temperature of between about 160° C. and about 200° C. in a time period of less than about 30 seconds after said treating; and
(ii) depressurisation and cooling the product mixture to ambient temperature by release through a pressure let down device.

The pressure let down device may be enveloped in ambient temperature water.

The depressurising and cooling of the product mixture may occur simultaneously.

The depressurising and cooling of the product mixture may occur separately.

In one embodiment the lignocellulosic feedstock is wood (e.g. *radiata* pine).

In one embodiment, the reaction mixture further comprises a solid substrate, wherein the solid substrate is solid or substantially solid at the reaction temperature and pressure, sequesters organic and/or inorganic matter that de-solubilises within the reaction mixture or the product mixture; and/or alters one or more flow characteristics of the reaction mixture and/or the product mixture in the reactor vessel.

The organic matter may be lignocellulosic feedstock, coal (e.g. lignite), or a combination thereof.

The solid substrate may inhibit scaling in the reactor vessel.

The solid substrate may inhibit development of a pressure gradient in the reactor vessel during the conversion of the organic matter feedstock into the bio-product.

The depressurising may be facilitated by a pressure let down device in the reactor vessel.

The reaction mixture may be pressurised to a maximum pressure prior to or during the treating.

Prior to the depressurising facilitated by the pressure let down device, the product mixture may be pressurised at less than 98%, less than 95%, less than 90%, less than 85%, less than 80%, less than 75%, less than 70%, less than 65%, less than 60%, less than 55%, or less than 50%, of the maximum pressure.

The solid substrate may generate additional metal surface area within the reactor vessel by an abrasive action, to thereby provide additional metal surface area for provision of additional heterogeneous catalysts to the reaction mixture.

The solid substrate may be inert or substantially inert at the reaction temperature and pressure.

The solid substrate may be chemically inert or substantially chemically inert at the reaction temperature and pressure.

The solid substrate may be a carbonaceous material comprising at least 50%, at least 60%, at least 70%, at least 80%, or at least 90% by weight carbon.

In one embodiment of the first, second or third aspects, the solid substrate may be selected from the group consisting of: coals, anthracitic coal, meta-anthracite, anthracite semianthracite, bituminous coal, subbituminous coal, lignite (i.e. brown coal), coking coal, coal tar, coal tar derivatives, coal char, coke, high temperature coke, foundry coke, low and medium temperature coke, pitch coke, petroleum coke, coke oven coke, coke breeze, gas coke, brown coal coke, semi coke, charcoal, pyrolysis char, hydrothermal char, carbon black, graphite fine particles, amorphous carbon, carbon nanotubes, carbon nanofibers, vapor-grown carbon fibers, and any combination thereof.

In one embodiment of the first, second or third aspects, the solid substrate may be a non-carbonaceous material comprising no more than 10%, no more than 5%, no more than 1%, or no carbon.

The solid substrate may be selected from the group consisting of fly ash, a mineral, calcium carbonate, calcite, a silicate, silica, quartz, an oxide, a metal oxide, an insoluble or substantially insoluble metal salt, iron ore, a clay mineral, talc, gypsum, and any combination thereof.

The solid substrate may be selected from the group consisting of carbonates of calcium, carbonates of magnesium, carbonates of calcium and magnesium, calcite, limestone, dolomite, hydroxides of calcium, hydroxides of magnesium, oxides of calcium, oxides of magnesium, hydrogen carbonates of calcium, hydrogen carbonates of magnesium, kaolinite, bentonite, illite, zeolites, calcium phosphate, hydroxyapataite, phyllosilicates, and any combination thereof.

The solid substrate may be provided in the form of a powder, or a slurry comprising the powder.

The solid substrate may be present in the reaction mixture at a concentration of more than 0.5%, more than 1%, more than 3%, more than 5%, more than 10%, more than 25%, or more than 30% by weight.

The solid substrate is may be present in the reaction mixture at a concentration of less than 0.5%, less than 1%, less than 3%, less than 5%, less than 10%, less than 25%, or less than 50% by weight.

Organic and/or inorganic matter may be sequestered by the solid substrate by adsorbing the organic matter and/or inorganic matter onto a surface of the solid substrate or into the solid substrate.

In one embodiment of the first, second or third aspects, the reaction mixture comprises the organic matter feedstock (e.g. lignocellulosic matter) and the solid substrate at a ratio of about 1:1, about 3:2, about 2:1, about 3:1, about 4:1, about 5:1, about 6:1 about 8:1, about 10:1, about 20:1, or about 30:1.

In one embodiment of the first, second or third aspects, the solid substrate constitutes: at least 1%, at least 2%, at least 3%, at least 4%, at least 5%, at least 6%, at least 7%, at least 8%, at least 9%, at least 10%, at least 15%, at least 20%, at least 30%, at least 40%, at least 50%, between 1 wt % and 20%, between 1% and 10%, between 1% and 5%, between 5% and 10%, between 5% and 15%, between 5% and 20%, between 20% and 40%, between 20% and 50%, between 20% and 30%, between 30% and 40%, or between 40% and 50% of the total combined mass of the solid substrate and organic matter feedstock (e.g. lignocellulosic matter) in the reaction mixture.

In one embodiment, the method further comprises separating the solid substrate from the product mixture after the depressurising and cooling, and recycling the solid substrate into a second slurry or second reaction mixture comprising organic matter feedstock.

In one embodiment, the solid substrate is made from residue obtained by distillation or pyrolysis of the bio-product.

In one embodiment, the reaction mixture further comprises an oil additive.

The oil additive may be mixed with the feedstock and/or solvent prior to the treating.

The reaction mixture may comprise between 5% and 60%, between 5% and 50%, between 5% and 40%, between 5% and 30%, between 5% and between 20%, more the 5%, more than 10%, more than 15%, more than 20%, more than 30%, less than 20%, less than 15% or less than 10% of the oil additive by weight.

The oil additive may be selected from the group consisting of paraffinic oil, gas-oil, crude oil, synthetic oil, coal-oil, bio-oil, shale oil, kerogen oil, mineral oil, white mineral oil, aromatic oil, tall oil, distilled tall oil, plant or animal oils, fats and their acidic forms and esterified forms, and any combination thereof.

In one embodiment the solvent is a mixed solvent comprising an aqueous solvent component and an oil solvent component, wherein the two components are substantially immiscible or partly miscible at ambient temperature.

The oil component may be crude tall oil, distilled tall oil or a combination thereof.

In one embodiment, the solvent comprises water and oil in a ratio of about 1:1 by mass, of about 1:2 by mass, of about 2:1 by mass, of about 3:1 by mass, of about 1:3 by mass, of about 1:4 by mass, of about 4:1 by mass, of about 1:5 by mass, of about 5:1 by mass, of about 1:6 by mass, of about 6:1 by mass, of about 1:7 by mass, of about 7:1 by mass, of about 1:8 by mass, of about 8:1 by mass, of about 1:9 by mass, of about 9:1 by mass, of about 1:10 by mass, or of about 10:1 by mass.

In one embodiment, the method further comprises separating oil from the product and recycling the oil into a second slurry or second reaction mixture comprising organic matter feedstock.

In one embodiment, the method further comprises separating the solid substrate and oil from the product, and recycling the solid substrate and the oil into a second slurry or second reaction mixture comprising organic matter feedstock.

In one embodiment, the oil solvent is recycled from a bio-product produced according to the method.

In one embodiment, the solid substrate is recycled from a bio-product produced according to the method.

In one embodiment, the oil solvent and solid substrate are recycled in a mixture from a bio-product produced according to the method, and the mixture of recycled oil and recycled substrate is solid at ambient temperature.

In one embodiment, the bio-product comprises a compound selected from the group consisting of: waxes; aldehydes; carboxylic acids; carbohydrates; phenols; furfurals; alcohols; ketones; resins; resin acids; compounds structurally related to resin acids; alkanes; alkenes; fatty acids; fatty acid esters; sterols; sterol-related compounds; furanic oligomers; cyclopentanones; cyclohexanones; alkyl- and alkoxy-cyclopentanones; alkyl- and alkoxy-cyclohexanones; cyclopenteneones; alkyl- and alkoxy-cyclopentenones; aromatic compounds; naphthalenes; alkyl- and alkoxy-substituted naphthalenes; cresols; alkyl- and alkoxy-phenols; alkyl- and alkoxy-catechols; alkyl- and alkoxy-dihydroxybezenes; alkyl- and alkoxy-hydroquinones; indenes; indene-derivatives, and any combination thereof.

In one embodiment, the bio-product comprises an oil component having a gross calorific value of at least 30 MJ/kg, at least 32 MJ/kg, at least 35 MJ/kg, or at least 36 MJ/kg.

In one embodiment, the bio-product comprises an oil component having a gross calorific value of at least 30 MJ/kg, at least 32 MJ/kg, at least 35 MJ/kg, or at least 36 MJ/kg, and a mixed substrate and oil component having a gross calorific value of at least 26 MJ/kg, at least 28 MJ/kg, at least 30 MJ/kg, at least 32 MJ/kg, or at least 33 MJ/kg.

In one embodiment, the method comprises dissolving bio-oil from the bio-product in a purifying solvent and filtering the dissolved bio-oil to remove particulates and solid material.

In one embodiment, the purifying solvent comprises any one or more of: acetone, ethyl acetate, ethanol, benzene, toluene, xylene, tetralin, tetrahydrofuran, methyl ethyl ketone, dichloromethane, chloroform, ketones, alcohol, furans, light cycle oil, naphtha, and/or a distilled fraction of bio-oil from a bio-product produced in accordance with the methods of the present invention.

In one embodiment, the distilled fraction is obtained by boiling said bio-oil from a bio-product produced in accordance with the methods of the present invention, at a temperature of between about 60° C. and about 150° C.

In one embodiment, the purifying solvent is recovered by distillation following said filtration.

In a second aspect, the present invention provides a bio-product obtained or obtainable by the method of the first aspect.

The bio-product may be a bio-oil.

BRIEF DESCRIPTION OF THE FIGURES

Preferred embodiments of the present invention will now be described, by way of example only, with reference to the accompanying Figures wherein:

FIG. 1 shows gross calorific value (GCV) vs oxygen content in biocrudes generated from *Radiata* Pine plus sodium hydroxide (circles), and from hog fuel and black liquor feeds (triangles—as labelled), in accordance with methods of the present invention; and FIG. 2 is a schematic representation of a pilot plant reactor for performing feedstock conversion under continuous flow according to the methods of present invention.

DEFINITIONS

As used in this application, the singular form "a", "an" and "the" include plural references unless the context clearly dictates otherwise. For example, the term "a catalyst" also includes a plurality of catalysts.

As used herein, the term "comprising" means "including." Variations of the word "comprising", such as "comprise" and "comprises," have correspondingly varied meanings. Thus, for example, a bio-product "comprising" a bio-oil may consist exclusively of bio-oil or may include other additional substances.

As used herein, the terms "organic matter" and "organic materials" have the same meaning and encompass any material comprising carbon including both fossilised and non-fossilised materials. Non-limiting examples of organic matter include renewable sources of biomass (e.g. lignocellulosic matter), as well as hydrocarbon-containing materials (e.g. lignite, oil shale and peat) which may be non-renewable.

As used herein the term "bio-product" encompasses any product that can be obtained by the treatment of organic matter feedstock as defined above in accordance with the methods of the present invention. Non-limiting examples of bio-products include biofuels (e.g. bio-oils, char products, gaseous products) and chemical products (e.g. platform chemicals, organic acids, furanics, furfural, hydroxymethylfurfural, levoglucosan, sorbitol, cylitol, arabinitol, formaldehyde, acetaldehyde).

As used herein, the term "biofuel" refers to an energy-containing material derived from the treatment of organic matter feedstock as defined above in accordance with the methods of the present invention. Non-limiting examples of biofuels include bio-oils, char products (e.g. upgraded pulvarised coal injection (PCI) equivalent products and fuels for direct injection carbon engines (DICE)), and gaseous products (a gaseous product comprising methane, hydrogen, carbon monoxide and/or carbon dioxide).

As used herein the term "bio-oil" refers to a complex mixture of compounds derived from the treatment of organic matter feedstock as defined above in accordance with the methods of the present invention. The bio-oil may comprise compounds including, but not limited to, any one or more of alkanes, alkenes, aldehydes, carboxylic acids, carbohydrates, phenols, furfurals, alcohols, and ketones. The bio-oil may comprise multiple phases including, but not limited to, a water-soluble aqueous phase which may comprise, compounds including, but not limited to, any one or more of carbohydrates, aldehydes, carboxylic acids, carbohydrates, phenols, furfurals, alcohols, and ketones, resins and resin acids, and compounds structurally related to resin acids, alkanes and alkenes, fatty acids and fatty acid esters, sterols and sterol-related compounds, furanic oligomers, cyclopentanones, and cyclohexanones, alkyl- and alkoxy-cyclopentanones, and cyclohexanones, cyclopenteneones, alkyl- and alkoxy-cyclopentenones, aromatic compounds including naphthalenes and alkyl- and alkoxy-substituted naphthalenes, cresols, alkyl- and alkoxy-phenols, alkyl- and alkoxy-catechols, alkyl- and alkoxy-dihydroxybezenes, alkyl- and alkoxy-hydroquinones, indenes and indene-derivatives; and a water-insoluble phase which may comprise, compounds including, but not limited to, any one or more of waxes, aldehydes, carboxylic acids, carbohydrates, phenols, furfurals, alcohols, and ketones, resins and resin acids, and compounds structurally related to resin acids, alkanes and alkenes, fatty acids and fatty acid esters, sterols and sterol-related compounds, furanic oligomers, cyclopentanones, and cyclohexanones, alkyl- and alkoxy-cyclopentanones, and cyclohexanones, cyclopenteneones, alkyl- and alkoxy-cyclopentenones, aromatic compounds including naphthalenes and alkyl- and alkoxy-substituted naphthalenes, cresols, alkyl- and alkoxy-phenols, alkyl- and alkoxy-catechols, alkyl- and alkoxy-dihydroxybezenes, alkyl- and alkoxy-hydroquinones, indenes and indene-derivatives.

As used herein, the term "lignocellulosic" encompasses any substance comprising lignin, cellulose, and hemicellulose. By way of non-limiting example, lignocellulosic matter may comprise at least 10% lignin, at least 10% cellulose and at least 10% hemicellulose.

As used herein, the term "fossilised organic matter" encompasses any organic material that has been subjected to geothermal pressure and temperature for a period of time sufficient to remove water and concentrate carbon to significant levels. For example, fossilised organic material may comprise more than about 10%, 20%, 30%, 40%, 50%, 60%, 70%, 75%, 80%, 85%, 90% or 95 wt % carbon. Non-limiting examples of fossilised organic matter include coals (e.g. anthracitic coals such as meta-anthracite, anthracite and semianthracite; bituminous coals; subbituminous coals; lignite (i.e. brown coal), coking coal, coal tar, coal tar derivatives, coal char), cokes (e.g. high temperature coke, foundry coke, low and medium temperature coke, pitch coke, petroleum coke, coke oven coke, coke breeze, gas coke, brown coal coke, semi coke), peat (e.g. milled peat, sod peat), kerogen, tar sands, oil shale, shale tar, asphalts, asphaltines, natural bitumen, bituminous sands, or any combination thereof.

As used herein, the term "pulping liquor" will be understood to encompass "black liquor", "green liquor", "white liquor", and any combination thereof.

As used herein, the term "black liquor" will be understood to mean an alkaline aqueous solution arising from the treatment of lignocellulosic matter (e.g. pulpwood) into paper pulp using pulping chemicals (e.g. alkaline solution of soda and/or sulfate) which act to free the cellulose fibers from the wood. Black liquor comprises a mixture of dissolved organics (e.g. lignin residues, hemicellulose), inorganic chemicals, and water. It can be separated from the generated pulp using conventional techniques and may optionally be concentrated by removal of water. "Strong" black liquor may, for example, comprise 46-57% solids by weight. "Heavy" black liquor may, for example, comprise 63%-80% solids by weight. The precise chemical makeup of black liquor will depend on the type of lignocellulosic material subjected to the pulping process, concentration/make-up of pulping chemicals and so on. By way of non-limiting example, black liquor may comprise 12%-20% solids (50%-70% organics, 20%-40% inorganics), 5-10% NaOH, 15%-30% $Na_2S$, 30%-40% $Na_2CO_3$, 5%-15% $Na_2SO_3$, 8%-18% $Na_2SO_4$, and/or 10%-20% $Na_2S_2O_3$.

As used herein, the term "green liquor" will be understood to mean an aqueous solution of black liquor smelt dissolved in a solvent (e.g. water), and comprising sodium carbonate. The black liquor smelt may arise from the incineration of black liquor that has been concentrated by the evaporation of water (for example, to over 60% solids content). The precise mechanical make-up of green liquor will depend on factors such as the chemical make-up and degree of solids content of the black liquor material from which it is derived, specifics of the incineration process to produce black liquor smelt, and so on. way of non-limiting example, green liquor may comprise NaOH (5%-10%), $Na_2S$ (15%-25%%), $Na_2CO_3$ (55%-65%), $Na_2SO_3$ (1%-6%), $Na_2SO_4$ (3%-9%), and $Na_2S_2O_3$ (1%-6%).

As used herein, the term "white liquor" will be understood to mean an alkaline aqueous solution comprising sodium hydroxide and sodium sulfide, and other sodium salts, such as sodium sulfate ($Na_2SO_4$) and sodium carbonate ($Na_2CO_3$) and small amounts of sulfites and chlorides. White liquor may arise from treatment of green liquor with lime (CaO/ $Ca(OH)_2$). The green liquor may optionally be clarified to remove insoluble materials (e.g. calcium compounds, unburned carbon, metals) prior to treatment with the lime. The precise chemical makeup of white liquor will depend on factors such as the specific reaction conditions used to prepare it from green liquor, and the nature of the green liquor from which it is derived. By way of non-limiting example, white liquor may comprise between about 48 wt % and 58 wt % sodium hydroxide (NaOH), between about 15 wt % and 25 wt % sodium sulfide ($Na_2S$), between about 10 wt % and about 20 wt % sodium carbonate ($Na_2CO_3$), between about 1 wt % and about 5 wt % sodium sulfite ($Na_2SO_3$), between about 2 wt % and about 7 wt % sodium sulfate ($Na_2SO_4$), and between about 1.5 wt % and about 4 wt % sodium thiosulfate ($Na_2S_2O_3$).

As used herein, the term "solvent" includes within its scope an "aqueous solvent", an "oil solvent", and combinations thereof.

As used herein, the term "aqueous solvent" refers to a solvent comprising at least one percent water based on total weight of solvent. An "aqueous solvent" may therefore comprise between one percent water and one hundred percent water based on total weight of solvent. An "aqueous solvent" will also be understood to include within its scope "aqueous alcohol", "aqueous ethanol", and "aqueous methanol".

As used herein, the term "aqueous alcohol" refers to a solvent comprising at least one percent alcohol based on total weight of solvent.

As used herein, the term "aqueous ethanol" refers to a solvent comprising at least one percent ethanol based on total weight of solvent.

As used herein, the term "aqueous ethanol" refers to a solvent comprising at least one percent methanol based on total weight of solvent.

As used herein, the term "oil solvent" refers to a solvent comprising any suitable oil, non-limiting examples of which include paraffinic oil, gas-oil, crude oil, synthetic oil, coal-oil, bio-oil, shale oil/kerogen oil, aromatic oils (i.e. single or multi-ringed components or mixtures thereof), tall oils, triglyceride oils, fatty acids, ether extractables, hexane extractables, and any mixture of any of the previous components, and in which the oil constitutes at least one percent of the solvent based on total solvent weight.

As used herein the term "oil additive" refers to any suitable oil component for inclusion in a feedstock, solvent and/or reaction mixture according to the present invention, non-limiting examples of which include paraffinic oil, gas-oil, crude oil, synthetic oil, coal-oil, bio-oil, shale oil/kerogen oil, aromatic oils (i.e. single or multi-ringed components or mixtures thereof), tall oils, triglyceride oils, fatty acids, ether extractables, hexane extractables, and any mixture of any of the previous components. The oil additive may constitute at least one percent portion of the feedstock, solvent and/or reaction mixture to which it is added, based on total weight of the feedstock, solvent and/or reaction mixture.

As used herein, a "supercritical" substance (e.g. a supercritical solvent) refers to a substance that is heated above its critical temperature and pressurised above its critical pressure (i.e. a substance at a temperature and pressure above its critical point).

As used herein, a "subcritical" substance (e.g. a subcritical solvent) refers to a substance at a temperature and/or pressure below the critical point of the substance. Accordingly, a substance may be "subcritical" at a temperature below its critical point and a pressure above its critical point, at a temperature above its critical point and a pressure below its critical point, or at a temperature and pressure below its critical point.

As used herein, a "solid substrate" is a component that is solid or substantially solid at a reaction temperature and pressure used in accordance with the methods of the present invention. The solid substrate may be capable of sequestering organic and/or inorganic matter that de-solubilises within the reaction mixture and/or a product mixture produced from the reaction mixture. Additionally or alternatively, the solid substrate may be capable of altering the flow characteristics of the reaction mixture or the product mixture in a reactor vessel. Solid substrates encompass both carbonaceous and non-carbonaceous materials, non-limiting examples of which include coals, anthracitic coal, meta-anthracite, anthracite semianthracite, bituminous coal, sub-bituminous coal, lignite (i.e. brown coal), coking coal, coal tar, coal tar derivatives, coal char, coke, high temperature coke, foundry coke, low and medium temperature coke, pitch coke, petroleum coke, coke oven coke, coke breeze, gas coke, brown coal coke, semi coke, charcoal, pyrolysis char, hydrothermal char, carbon black, graphite fine particles, amorphous carbon, carbon nanotubes, carbon nanofibers, vapor-grown carbon fibers, fly ash, a mineral, calcium carbonate, calcite, a silicate, silica, quartz, an oxide, a metal oxide, an insoluble or substantially insoluble metal salt, iron ore, a clay mineral, talc, gypsum, carbonates of calcium, carbonates of magnesium, carbonates of calcium and magnesium, calcite, limestone, dolomite, hydroxides of calcium, hydroxides of magnesium, oxides of calcium, oxides of magnesium, hydrogen carbonates of calcium, hydrogen carbonates of magnesium, kaolinite, bentonite, illite, zeolites, calcium phosphate, hydroxyapataite, phyllosilicates, and any combination thereof.

As used herein, the term "continuous flow" refers to a process wherein a slurry comprising lignocellulosic feedstock and any one or more of: a solvent, solid substrate, pulping liquor, and/or oil additive, is subjected to:

(a) heating and pressurisation to a target temperature and pressure, (b) treatment at target temperature(s) and pressure(s) for a defined time period (a "retention time"), and (c) cooling and de-pressurisation;

during which the slurry is maintained in a stream of continuous movement along the length (or partial length) of a given surface of a reactor vessel. It will be understood that "continuous flow" conditions as contemplated herein are defined by a starting point of heating and pressurisation (i.e. (a) above) and by an end point of cooling and de-pressurisation (i.e. (c) above). Continuous flow conditions as contemplated herein imply no particular limitation regarding flow velocity of the slurry provided that it is maintained in a stream of continuous movement.

As used herein, the terms "reactor", "reactor apparatus", and "reactor vessel" are used interchangeably and have the same meaning. Each term encompasses any apparatus suitable for performing the methods of the present invention including, for example, continuous flow reactors and batch reactors.

As used herein a "substantially solid" substrate refers to a substrate that is predominantly solid at a specified reaction temperature and/or pressure in that at least 50%, at least 60%, at least 70%, at least 80%, at least 90%, preferably at least 95%, and more preferably at least 98% of the substrate is in a solid form.

As used herein, a "substantially insoluble" substance is one that is predominantly insoluble at a specified reaction temperature and/or pressure in that at least 90%, preferably at least 95%, and more preferably at least 98% of the substrate is not solubilised.

As used herein, an "inert" or "chemically inert" solid substrate is one that does not chemically react with other components in a reaction mixture or catalyse reactions between components in a reaction mixture, at a specified reaction temperature and pressure or at a range of reaction temperatures and pressures.

As used herein, a "substantially inert" or "substantially chemically inert" solid substrate one that does not to any significant degree chemically react with other components in a reaction mixture or catalyse reactions between components in a reaction mixture, at a specified reaction temperature and pressure or at a range of reaction temperatures and pressures. A "substantially inert" or "substantially chemically inert" solid substrate will be understood to react with any other component in a given reaction mixture, or catalyse a reaction between any given components in a reaction mixture, on less than 5%, less than 4%, less than 3%, less than 2%, or less than 1%, of interaction events with the component(s). It will be understood that use of the term "about" herein in reference to a recited numerical value (e.g. a temperature or pressure) includes the recited numerical value and numerical values within plus or minus ten percent of the recited value.

It will be understood that use of the term "between" herein when referring to a range of numerical values encompasses the numerical values at each endpoint of the range. For example, a temperature range of between 10° C. and 15° C. is inclusive of the temperatures 10° C. and 15° C.

Any description of a prior art document herein, or a statement herein derived from or based on that document, is not an admission that the document or derived statement is a part of the common general knowledge of the relevant art.

For the purposes of description all documents referred to herein are incorporated by reference in their entirety unless otherwise stated.

DETAILED DESCRIPTION OF THE INVENTION

Modifications to processes for the thermochemical conversion of biomass into biofuels that are capable of increasing process efficiency, lowering costs and/or improving product characteristics are still highly sought after.

The present invention relates to the determination that pulping liquors, an abundant byproduct of kraft pulping mill processes, can be used as a source of catalysts for the thermochemical conversion of organic matter feedstocks (e.g. lignocellulosic matter, coals such as lignite) into bio-products. Moreover, in view of their significant cellulosic content, the pulping liquors can also provide a source of feedstock material for conversion into bio-products, thus reducing the amount of feedstock material required.

Black liquor is a waste product of the kraft pulping process in which lignocellulosic matter (e.g. pulpwood) is dissolved under heat and pressure using pulp chemicals. The treatment of the wood in this manner results in a mixture containing pulp and black liquor, a diverse mixture of reacted pulping chemicals/inorganic elements, and dissolved wood substances including acetic acid, formic acid, carboxylic acids, sugars, xylans, and/or methanol. Despite the complex chemical makeup of black liquor and its derivatives, the present inventors have identified that it is a suitable substitute for conventional catalysts used for the thermochemical processing of lignocellulosic matter into bio-oils and related bio-products. Moreover, black liquor contains a significant amount of cellulosic fibers capable of conversion into bio-products via thermochemical processes. Accordingly, the present invention provides a means of increasing the cost-efficiency of thermochemical processes for producing bio-products from organic matter feedstocks.

The present invention thus related to methods for producing bio-products by treating organic matter feedstock with various solvents and in the presence of pulping liquor at increased temperature and pressure. Additional aspects of the present invention relate to bio-products generated by the methods described herein.

The present invention provides methods for the conversion of organic matter feedstock into bio-products (e.g. biofuels including bio-oils; chemical products etc.). As used herein, "organic matter" (also referred to herein as "organic material") encompasses any matter comprising carbon, including both fossilised and non-fossilised forms of carbon-comprising matter.

No limitation exists regarding the particular type of organic matter feedstocks utilised in the methods of the invention, although it is contemplated that the use of a solid substrate in accordance with the methods of the present invention may be more beneficial during the conversion of non-fossilised forms of organic matter (e.g. lignocellulosic matter) compared to fossilised forms of organic matter.

Organic matter utilised in the methods of the invention may comprise naturally occurring organic matter (e.g. lignocellulosic biomass and the like) and/or synthetic organic materials (e.g. synthetic rubbers, plastics, nylons and the like). In some embodiments, organic matter utilised in the methods of the invention comprises a mixture of fossilised organic matter and non-fossilised organic matter (e.g. lignocellulosic matter). In such cases, the fossilised organic matter may remain solid at reaction temperature and pressure in which case it may act as a solid substrate as described herein. In the case where more than one type (i.e. a mixture) of organic matter is utilised, no limitation exists regarding the particular proportion of the different components of organic matter.

In preferred embodiments, organic matter utilised in the methods of the invention is or comprises lignocellulosic matter. Lignocellulosic matter as contemplated herein refers to any substance comprising lignin, cellulose and hemicellulose.

For example, the lignocellulosic matter may be a woody plant or component thereof. Examples of suitable woody plants include, but are not limited to, pine (e.g. *Pinus radiata*), birch, *eucalyptus*, bamboo, beech, spruce, fir, cedar, poplar, willow and aspen. The woody plants may be coppiced woody plants (e.g. coppiced willow, coppiced aspen).

Is Additionally or alternatively, the lignocellulosic matter may be a fibrous plant or a component thereof. Non-limiting examples of fibrous plants (or components thereof) include grasses (e.g. switchgrass), grass clippings, flax, corn cobs, corn stover, reed, bamboo, bagasse, hemp, sisal, jute, *cannabis*, hemp, straw, wheat straw, abaca, cotton plant, kenaf, rice hulls, and coconut hair.

Additionally or alternatively, the lignocellulosic matter may be derived from an agricultural source. Non-limiting examples of lignocellulosic matter from agricultural sources include agricultural crops, agricultural crop residues, and grain processing facility wastes (e.g. wheat/oat hulls, corn fines etc.). In general, lignocellulosic matter from agricultural sources may include hard woods, soft woods, hardwood stems, softwood stems, nut shells, branches, bushes, canes, corn, corn stover, cornhusks, energy crops, forests, fruits, flowers, grains, grasses, herbaceous crops, wheat straw, switchgrass, salix, sugarcane bagasse, cotton seed hairs, leaves, bark, needles, logs, roots, saplings, short rotation woody crops, shrubs, switch grasses, trees, vines, cattle manure, and swine waste.

Additionally or alternatively, the lignocellulosic matter may be derived from commercial or virgin forests (e.g. trees, saplings, forestry or timber processing residue, scrap wood such as branches, leaves, bark, logs, roots, leaves and products derived from the processing of such materials, waste or byproduct streams from wood products, sawmill and paper mill discards and off-cuts, sawdust, and particle board).

Additionally or alternatively, the lignocellulosic matter may be derived from industrial products and by-products. Non-limiting examples include wood-related materials and woody wastes and industrial products (e.g. pulp, paper (e.g. newspaper) papermaking sludge, cardboard, textiles and cloths, dextran, and rayon).

It will be understood that organic material used in the methods of the invention may comprise a mixture of two or more different types of lignocellulosic matter, including any combination of the specific examples provided above.

The relative proportion of lignin, hemicellulose and cellulose in a given sample will depend on the specific nature of the lignocellulosic matter.

By way of example only, the proportion of hemicellulose in a woody or fibrous plant used in the methods of the invention may be between about 15% and about 40%, the proportion of cellulose may be between about 30% and about 60%, and the proportion of lignin may be between about 5% and about 40%. Preferably, the proportion of hemicellulose in the woody or fibrous plant may be between about 23% and about 32%, the proportion of cellulose may be between about 38% and about 50%, and the proportion of lignin may be between about 15% and about 25%.

In some embodiments, lignocellulosic matter used in the methods of the invention may comprise between about 2% and about 35% lignin, between about 15% and about 45% cellulose, and between about 10% and about 35% hemicellulose.

In other embodiments, lignocellulosic matter used in the methods of the invention may comprise between about 20% and about 35% lignin, between about 20% and about 45% cellulose, and between about 20% and about 35% hemicellulose.

In some embodiments, the lignocellulosic matter may comprise more than about 5%, 10%, 15%, 20%, 25%, 30%, 35%, 40%, 45%, or 50% lignin.

In some embodiments, the lignocellulosic matter may comprise more than about 5%, 10%, 15%, 20%, 25%, 30%, 35%, 40%, 45%, or 50% cellulose.

In some embodiments, the lignocellulosic matter may comprise more than about 5%, 10%, 15%, 20%, 25%, 30%, 35%, 40%, 45%, or 50% hemicellulose.

The skilled addressee will recognize that the methods described herein are not constrained by the relative proportions of lignin, hemicellulose and cellulose in a given source of lignocellulosic matter.

In certain embodiments of the invention, a mixture of organic material comprising lignite (brown coal) and lignocellulosic matter may be utilised as organic matter feedstock in the methods of the invention. The lignocellulosic matter of the mixture may, for example, comprise woody plant material and/or fibrous plant material. The proportion of lignite in the mixture may be greater than about 20%, 40%, 60% or 80%. Alternatively, the proportion of lignocellulosic matter in the mixture may be greater than about 20%, 40%, 60% or 80%.

In some preferred embodiments, organic matter utilised in the methods of the invention comprises carbon-containing polymeric materials, non-limiting examples of which include rubbers (e.g. tyres), plastics and polyamides (e.g. nylons).

Non-limiting examples of suitable rubbers include natural and synthetic rubbers such as polyurethanes, styrene rubbers, neoprenes, polybutadiene, fluororubbers, butyl rubbers, silicone rubbers, plantation rubber, acrylate rubbers, thiokols, and nitrile rubbers.

Non-limiting examples of suitable plastics include PVC, polyethylene, polystyrene, terphtalate, polyethylene and polypropylene.

Organic matter feedstocks utilised in the methods of the invention may comprise carbon-containing wastes such as sewage, manure, or household or industrial waste materials.

Pre-Treatment of Organic Matter

Organic matter utilised in the methods of the present invention may optionally be pre-treated prior converting it into bio-product(s).

It will be recognised that no strict requirement exists to perform a pre-treatment step when using the methods described herein. For example, pre-treatment of the organic matter may not be required if it is obtained in the form of a liquid or in a particulate form. However, it is contemplated that in many cases pre-treatment of the organic matter may be advantageous in enhancing the outcome of the methods described herein.

In general, pre-treatment may be used to break down the physical and/or chemical structure of the organic matter making it more accessible to various reagents utilised in the methods of the invention (e.g. oil-based solvent, catalysts and the like) and/or other reaction parameters (e.g. heat and pressure). In certain embodiments, pre-treatment of organic matter may be performed for the purpose of increasing solubility, increasing porosity and/or reducing the crystallinity of sugar components (e.g. cellulose). Pre-treatment of the organic matter may be performed using an apparatus such as, for example, an extruder, a pressurized vessel, or batch reactor.

Pre-treatment of the organic matter may comprise physical methods, non-limiting examples of which include grinding, chipping, shredding, milling (e.g. vibratory ball milling), compression/expansion, agitation, and/or pulse-electric field (PEF) treatment.

Additionally or alternatively, pre-treatment of the organic matter may comprise physio-chemical methods, non-limiting examples of which include pyrolysis, steam explosion, ammonia fiber explosion (AFEX), ammonia recycle percolation (ARP), and/or carbon-dioxide explosion. Pre-treatment with steam explosion may additionally involve agitation of the organic matter.

Additionally or alternatively, pre-treatment of the organic matter may comprise chemical methods, non-limiting examples of which include ozonolysis, acid hydrolysis (e.g. dilute acid hydrolysis using $H_2SO_4$ and/or HCl), alkaline hydrolysis (e.g. dilute alkaline hydrolysis using sodium, potassium, calcium and/or ammonium hydroxides), oxidative delignification (i.e. lignin biodegradation catalysed by the peroxidase enzyme in the presence of $H_2O_2$), and/or the organosolvation method (i.e. use of an organic solvent mixture with inorganic acid catalysts such as $H_2SO_4$ and/or HCl to break lignin-hemicellulose bonds).

Additionally or alternatively, pre-treatment of the organic matter may comprise biological methods, non-limiting examples of which include the addition of microorganisms (e.g. rot fungi) capable of degrading/decomposing various component(s) of the organic matter.

In some embodiments, organic matter used in the methods of the present invention is lignocellulosic matter which may be subjected to an optional pre-treatment step in which hemicellulose is extracted. Accordingly, the majority of the hemicellulose (or indeed all of the hemicellulose) may be extracted from the lignocellulosic matter and the remaining material (containing predominantly cellulose and lignin) used to produce a biofuel by the methods of the invention. However, it will be understood that this pre-treatment is optional and no requirement exists to separate hemicellulose from lignocellulosic matter when performing the methods of the present invention. Suitable methods for the separation of hemicellulose from lignocellulosic matter are described, for example, in PCT publication number WO/2010/034055, the entire contents of which are incorporated herein by reference.

For example, the hemicellulose may be extracted from lignocellulosic matter by subjecting a slurry comprising the lignocellulosic matter (e.g. 5%-15% w/v solid concentration) to treatment with a mild aqueous acid (e.g. pH 6.5-6.9) at a temperature of between about 100° C. and about 250° C., a reaction pressure of between about 2 and about 50 atmospheres, for between about 5 and about 20 minutes. The solubilised hemicellulose component may be separated from the remaining solid matter (containing predominantly cellulose and lignin) using any suitable means (e.g. by use of an appropriately sized filter). The remaining solid matter may be used directly in the methods of the invention, or alternatively mixed with one or more other forms of organic matter (e.g. lignite) for use in the methods of the invention.

Slurry Characteristics

Organic matter feedstock utilised in accordance with the methods of the present invention is preferably treated in the form of a slurry. Accordingly, the reaction mixture may be in the form of a slurry.

The slurry may comprise the organic matter in combination with a solvent (e.g. an aqueous solvent, an aqueous alcohol solvent, an aqueous ethanol solvent, an aqueous methanol solvent) optionally in combination with pulping liquor, solid substrate, a catalyst additive, and/or an oil additive. The slurry may be generated, for example, by generating a particulate form of the organic matter (e.g. by physical methods such as those referred to above and/or by other means) and mixing with the solvent.

No particular limitation exists regarding the relative proportions of solvent, feedstock, oil additive and/or solid substrate in the slurry. Non-limiting examples of potential quantities of these various components are described in the sections below.

Organic Matter Feedstock Component

A slurry for use in accordance with the methods of the present invention will generally comprise organic matter feedstock.

In certain embodiments of the invention, the concentration of organic matter in the slurry may be less than about 85 wt %, less than about 75 wt %, or less than about 50 wt %. Alternatively, the concentration of organic matter may be more than about 10 wt %, more than about 20 wt %, more than about 30 wt %, more than about 40 wt %, more than about 50 wt %, or more than about 60 wt %.

In some embodiments the slurry may comprise between about 35 wt % and about 45 wt % of an oil additive. In other embodiments, the slurry may comprise about 40 wt % oil or 39.5 wt % of an oil additive.

The optimal particle size of solid components of the organic matter feedstock and the optimal concentration of those solids in the slurry may depend upon factors such as, for example, the heat transfer capacity of the organic matter utilised (i.e. the rate at which heat can be transferred into and through individual particles), the desired rheological properties of the slurry and/or the compatibility of the slurry with component/s of a given apparatus within which the methods of the invention may be performed (e.g. reactor tubing). The optimal particle size and/or concentration of solid components of the organic matter components in a slurry used for the methods of the present invention can readily be determined by a person skilled in the art using standard techniques. For example, a series of slurries may be generated, each sample in the series comprising different particle sizes and/or different concentrations of the solid organic matter components compared to the other samples. Each slurry can then be treated in accordance with the methods of the invention under a conserved set of reaction conditions. The optimal particle size and/or concentration of solid organic matter components can then be determined upon analysis and comparison of the products generated from each slurry using standard techniques in the art.

In certain embodiments of the invention, the particle size of solid organic matter components in the slurry may be between about 10 microns and about 10,000 microns. For example, the particle size may be more than about 50, 100, 500, 750, 1000, 2000, 3000, 4000, 5000, 6000, 7000, 8000 or 9000 microns. Alternatively, the particle size may be less than about 50, 100, 500, 750, 1000, 2000, 3000, 4000, 5000, 6000, 7000, 8000 or 9000 microns. In some embodiments, the particle size is between about 10 microns and about 50 microns, between about 10 microns and about 100 microns, between about 10 microns and about 200 microns, between about 10 microns and about 500 microns, between about 10 microns and about 750 microns, or between about 10 microns and about 1000 microns. In other embodiments, the particle size is between about between about 100 microns and about 1000 microns, between about 100 microns and about 750 microns, between about 100 microns and about 500 microns, or between about 100 microns and about 250 microns.

One non-limiting advantage of the present invention is that the methods can be used to process feedstock with a high content of ash or inorganic material.

Pulping Liquor Component

A slurry for use in accordance with the methods of the present invention will generally comprise a pulping liquor component. The pulping liquor may be included in the slurry prior to heating and/or pressurising the slurry to target reaction conditions. Additionally or alternatively, the pulping liquor may be included in the slurry while the slurry is undergoing heating and/or pressurising to target reaction conditions. Additionally or alternatively, the pulping liquor may be included in the slurry after it has undergone heating and/or pressurising to target reaction conditions.

In some embodiments the slurry may comprise pulping liquor (black liquor, green liquor, white liquor, or any combination thereof).

For example, the slurry may comprise between about 1% and about 100%, between about 90% and about 100%, between about 95% and about 100%, between about 50% and about 100%, between about 50% and about 90%, between about 50% and about 95%, between about 50% and about 95%, between about 50% and about 80%, between about 50% and about 70%, between about 50% and about 60%, between about 30% and about 90%, between about 40% and about 90%, or between about 20% and about 75%, of the pulping liquor by weight.

For example, the slurry may comprise between about 60 wt % and about 100 wt % of the pulping liquor, between about 5 wt % and about 60 wt %, between about 1 wt % and about 50 wt %, between about 1 wt % and about 40 wt %, between about 1 wt % and about 30 wt %, between about 1 wt % and about 20 wt %, between about 1 wt % and about 15 wt %, between about 1 wt % and about 10 wt %, between about 1 wt % and about 5 wt %, between about 2 wt % and about 20 wt %, between about 2 wt % and about 10 wt %, between about 3% and about 20 wt %, between about 3 wt % and about 10 wt %, between about 0.5 wt % and about 5 wt %, between about 2 wt % and about 8 wt %, between about 3 wt % and about 5 wt %, or between about 5 wt % and about 15 wt % of the pulping liquor.

In some embodiments, the pulping liquor (black liquor, green liquor, white liquor, or any combination thereof) may be used in an amount of between about 0.1% and about 10% w/v pulping liquor, between about 0.1% and about 7.5% w/v pulping liquor, between about 0.1% and about 5% w/v pulping liquor, between about 0.1% and about 2.5% w/v pulping liquor, between about 0.1% and about 1% w/v pulping liquor, or between about 0.1% and about 0.5% w/v pulping liquor (in relation to the solvent).

Solvent Component

A slurry for use in accordance with the methods of the present invention will generally comprise a solvent component. The solvent may be an aqueous solvent, an oil solvent, or a combination thereof.

The solvent may comprise or consist of water.

In certain embodiments of the invention, the concentration of water in the slurry may be above about 80 wt %, above about 85 wt %, or above about 90 wt %. Accordingly, the concentration of water may be above about 75 wt %, above about 70 wt %, above about 60 wt %, above about 50 wt %, above about 40 wt %, or above about 30 wt %. In some embodiments, the concentration of water is between about 90 wt % and about 95 wt %.

In some embodiments the slurry comprises between about 10 wt % and about 30 wt % water. In other preferred embodiments, the slurry comprises about 20 wt % oil or about 15 wt % water.

In some embodiments, the water is recycled from the product of the process. For example, a portion water present following completion of the reaction may be taken off as a side stream and recycled into the slurry.

The solvent may comprise or consist of one or more aqueous alcohol/s.

For example, it may be suitable or preferable to use an aqueous alcohol as the solvent when the lignocellulosic feedstock used in the methods consists of or comprises a significant amount of lignocellulosic material and/or other materials such rubber and plastics due to the stronger chemical bonds in these types of lignocellulosic feedstock.

Suitable alcohols may comprise between one and about ten carbon atoms. Non-limiting examples of suitable alcohols include methanol, ethanol, isopropyl alcohol, isobutyl alcohol, pentyl alcohol, hexanol and iso-hexanol.

The slurry may comprise more than about 5 wt %, 10 wt %, 15 wt %, 20 wt %, 25 wt %, 30 wt %, 35 wt %, 40 wt %, 45 wt % or 50 wt % alcohol aqueous alcohol.

In certain embodiments, the solvent comprises a mixture of two or more aqueous alcohols. Preferably, the alcohol is ethanol, methanol or a mixture thereof.

Solid Substrate Component

A slurry for use in accordance with the methods of the present invention may comprise a solid substrate component as described herein.

Favourable characteristics of the solid substrate may include any one or more of the following: it remains inert or substantially inert at the reaction temperature and pressure used; it remains unaltered or substantially unaltered upon completion of the process; it remains as a solid or substantially solid at the reaction temperatures and pressures used; it is of low or moderate hardness so that it does not induce substantial abrasion or erosive corrosion in reactors (e.g. continuous flow reactors); it has a high internal or external specific surface area so that it can adsorb and/or absorb large quantities of bio-products and/or other precipitates during the conversion process.

The solid substrate may be a carbonaceous material. By way of non-limiting example only, the solid substrate may be a carbonaceous material comprising at least 50%, at least 60%, at least 70%, at least 80%, at least 90%, or at least 95% by weight carbon.

Non-limiting examples of suitable carbonaceous materials for use as the solid substrate include coals (e.g. anthracitic coals such as meta-anthracite, anthracite and semianthracite; bituminous coals, subbituminous coals, lignite (i.e. brown coal), coking coal, coal tar, coal tar derivatives, coal char); cokes (e.g. high temperature coke, foundry coke, low and medium temperature coke, pitch coke, petroleum coke, coke oven coke, coke breeze, gas coke, brown coal coke, semi coke); charcoal; pyrolysis char; hydrothermal char; carbon black; graphite fine particles; amorphous carbon; carbon nanotubes; carbon nanofibers; vapor-grown carbon fibers; and any combination thereof.

In some preferred embodiments of the present invention the solid substrate may be a carbon rich char made from the previous processing of organic matter according to the present invention followed by a thermal treatment in the substantial absence of oxygen to remove volatile materials (e.g. by pyrolysis or vacuum distillation at temperatures in the range of 200° C. to 800° C.).

The solid substrate may be a non-carbonaceous material. By way of non-limiting example only, the solid substrate may be a non-carbonaceous material comprising less than 20%, less than 10%, less than 5%, less than 3%, less than 2%, or less than 1%, by weight carbon, or comprise no carbon.

Non-limiting examples of suitable non-carbonaceous materials for use as the solid substrate include ash (e.g. fly ash); minerals (e.g. calcium carbonate, calcite, silicates, silica, quartz, oxides including iron ore, clay minerals, talc, gypsum); an insoluble or substantially insoluble metal salt; and any combination thereof.

Further non-limiting examples of suitable materials for use as the solid substrate include carbonates of calcium, carbonates of magnesium, carbonates of calcium and magnesium, calcite, limestone, dolomite, hydroxides of calcium, hydroxides of magnesium, oxides of calcium, oxides of magnesium, hydrogen carbonates of calcium, hydrogen carbonates of magnesium, kaolinite, bentonite, illite, zeolites, calcium phosphate, hydroxyapataite, phyllosilicates, and any combination thereof.

In certain embodiments of the present invention, the concentration of solid substrate in the slurry may be less than about 20 wt %, less than about 15 wt %, or less than about 10 wt %. Alternatively, the concentration of solid substrate may be more than about 0.5 wt %, more than about 1 wt %, more than about 3 wt %, more than about 5 wt %, more than about 50 8 wt %, or more than about 10 wt %.

The optimal particle size and optimal concentration of the solid substrate may depend upon factors such as, for example, the heat transfer capacity of the organic matter utilised (i.e. the rate at which heat can be transferred into and through individual particles), the desired rheological properties of the slurry and/or the compatibility of the slurry with component/s of a given apparatus within which the methods of the invention may be performed (e.g. reactor tubing). The optimal particle size and/or concentration of the solid substrate component in a slurry used for the methods of the invention can readily be determined by a person skilled in the art using standard techniques. For example, a series of slurries may be generated, each sample in the series comprising a specific solid substrate of different size and/or different concentration to those of other samples. Each slurry can then be treated in accordance with the methods of the invention under a conserved set of reaction conditions. The optimal solid substrate size and/or concentration can then be determined upon analysis and comparison of the products generated from each slurry using standard techniques in the art.

In certain embodiments of the invention, the size of a solid substrate component in the slurry may be between about 10 microns and about 10,000 microns. For example, the size may be more than about 50, 100, 500, 750, 1000, 2000, 3000, 4000, 5000, 6000, 7000, 8000 or 9000 microns. Alternatively, the size may less than about 50, 100, 500, 750, 1000, 2000, 3000, 4000, 5000, 6000, 7000, 8000 or 9000 microns. In some embodiments, the size is between about 10 microns and about 50 microns, between about 10 microns and about 100 microns, between about 10 microns and about 200 microns, between about 10 microns and about 500 microns, between about 10 microns and about 750 microns, or between about 10 microns and about 1000 microns. In other embodiments, the size is between about between about 100 microns and about 1000 microns, between about 100 microns and about 750 microns, between about 100 microns and about 500 microns, or between about 100 microns and about 250 microns.

In some embodiments of the invention, the particle size distributions and particle surface charge characteristics of the organic matter component of the slurry and/or the solid substrate component of the slurry may be optimized in order to provide desirable slurry characteristics when mixed, for example, to obtain minimum viscosity for a given solids content. The optimal particle size and/or particle surface charge of solid components in a given slurry used can readily be determined by a person skilled in the art using standard techniques. For example, a series of slurries may be generated, each sample in the series comprising different particle sizes and/or different concentrations of solid components compared to the other samples. Each slurry can then be treated in accordance with the methods of the invention under a conserved set of reaction conditions. The optimal particle size and/or particle surface charge of solid organic matter components can then be determined upon analysis and comparison of the products generated from each slurry using standard techniques known in the art.

Catalysts

Although the present invention contemplates the use of pulping liquors as an adequate source of catalysts for converting organic matter into bio-products using the methods described herein, intrinsic catalysts and/or additional catalysts may be employed if so desired.

An "intrinsic catalyst" is catalyst that is innately present in a given reaction component such as, for example, any one or more of organic matter feedstock, an aqueous solvent, and/or vessel walls of a reactor apparatus, or, a catalyst that form in situ during the treatment process.

As used herein, a "additional catalysts" is a catalyst incorporated into a feedstock slurry and/or reaction mixture that is supplementary to catalytic compounds present in pulping liquor included in the feedstock slurry, and supplementary to catalytic compounds intrinsically present in organic matter feedstock treated in accordance with the methods of the invention, catalytic compounds intrinsically present in any solvent used in accordance with the methods of the invention, catalytic compounds intrinsically present in a solid substrate used to perform the methods of the invention, and/or catalytic compounds intrinsically present in the walls of a reactor apparatus used to perform the methods of the invention.

Although the use of additional catalyst additive/s (i.e. beyond those in intrisic catalysts) may be advantageous in certain circumstances, the skilled addressee will recognise that the methods of the invention may be performed without using them.

A catalyst additive as contemplated herein may be any catalyst that enhances the formation of biofuel from organic matter (e.g. lignocellulosic feedstock and/or coals such as lignite) using the methods of the invention, non-limiting examples of which include base catalysts, acid catalysts, alkali metal hydroxide catalysts, transition metal hydroxide catalysts, alkali metal formate catalysts, transition metal formate catalysts, reactive carboxylic acid catalysts, transition metal catalysts, sulphide catalysts, noble metal catalysts, water-gas-shift catalysts, and combinations thereof. Suitable catalysts are described, for example, in United States of America patent publication number 2012-0311658 A1 entitled "Methods for biofuel production", the entire contents of which are incorporated herein by reference.

In certain embodiments, an additional catalysts or combination of additional catalysts may be used in an amount of between about 0.1% and about 10% w/v catalysts, between about 0.1% and about 7.5% w/v catalysts, between about 0.1% and about 5% w/v catalysts, between about 0.1% and about 2.5% w/v catalysts, between about 0.1% and about 1% w/v catalysts, or between about 0.1% and about 0.5% w/v catalysts (in relation to the solvent).

Table 1 below provides a summary of various exemplary additional catalysts that may be employed in the methods of the invention and the corresponding reactions that they may catalyse.

TABLE 1

Summary catalysts and corresponding reactions

| Reaction Type | Catalyst Family | Catalyst Family Member | Specific example(s) | Preferred catalysts/ comments |
|---|---|---|---|---|
| Hydrolysis | Base catalysts | Sub/super-critical water | Hydroxide ion in sub/super-critical water | |
| | | All alkali and transition metal salts, both cations and anions can contribute. Include all common inorganic anions | M = any alkali or transition metal<br>A = anions, including: aluminate, sulfate, sulfite, sulfide phosphate, phosphite nitrate, nitrite silicate hydroxide alkoxide carbonate oxide | M = Na, K, Fe, Ca, Ba<br>A = aluminate, phosphate, silicate, hydroxide, methoxide, ethoxide carbonate sulphate sulphide disulphide ($FeS_2$) oxide |
| | | Any organic base | ammonia, pyridine, etc. | |
| Hydrolysis | Acid catalysts (slower) | Sub/super-critical water | Hydronium ion in sub/super-critical water | |
| | | Any liquid mineral or organic acid | HA, where A = anions, including: aluminate, sulfate, sulfite, sulfide phosphate, phosphite nitrate, nitrite silicate hydroxide alkoxide carbonate carboxy group | Acids may form from the in-situ formation of carboxylic acids, phenolics and the presence of minerals |
| Dehydration (elimination) | Acid catalysts | Sub/super-critical water | Hydronium ion in sub/super-critical water | |
| | | Any liquid mineral or organic acid | HA, where A = anions, including: aluminate, sulfate, sulfite, sulfide phosphate, phosphite nitrate, nitrite silicate hydroxide alkoxide carbonate carboxy group | Acids may form from the in-situ formation of carboxylic acids, phenolics and the presence of minerals. zeolites or alumino-silicates in general may be added |
| Transfer Hydrogenation or in-situ $H_2$ generation | Transfer hydrogenation catalysts | All alkali and transition metal hydroxides and formates | M = any alkali or transition metal | M = Na, K |
| | | All reactive carboxylic acids | A = hydroxide, formate | A = hydroxide, formate formic, acetic |
| | | All transition and noble metals | All transition and noble metals | M = Fe, Pd, Pd, Ni Ru Rh |
| Decarboxylation | Largely thermal | Acid and transition (noble) metal cats have been reported to aid the process | All transition and noble metals supported on solid acids | $Pt/Al_2O_3/SiO_2$<br>$Pd/Al_2O_3/SiO_2$<br>$Ni/Al_2O_3/SiO_2$ |

TABLE 1-continued

Summary catalysts and corresponding reactions

| Reaction Type | Catalyst Family | Catalyst Family Member | Specific example(s) | Preferred catalysts/ comments |
|---|---|---|---|---|
| Decarbonylation | Largely thermal | As for decarboxylation | As for decarboxylation | As for decarboxylation |
| In-situ gasification | Largely thermal | Transition metals | supported transition metals | $Pt/Al_2O_3/SiO_2$ $Pd/Al_2O_3/SiO_2$ $Ni/Al_2O_3/SiO_2$ Fe |
| | | | sulfides | $Fe_xS_y$ $FeS/Al_2O_3$ $FeS/SiO_2$ $FeS/Al_2O_3/SiO_2$ |
| Water-Gas Shift | WGS catalysts | Standard WGS catalysts | As per literature | As per literature |
| Direct Hydrogenation with $H_2$ | Transition metals | Zero valent metals Sulfides | | Fe, Pt, P, Ni as zero valent FeS, $Fe_xS_y$ |
| Hydrode-oxygenation | Combined acid and hydrogenation catalyst | Transition metal and solid acid | M = transition metal A = acidic solid | $Pt/Al_2O_3/SiO_2$ $Pd/Al_2O_3/SiO_2$ $Ni/Al_2O_3/SiO_2$ $NiO/MoO_3$ $CoO/MoO_3$ $NiO/WO_2$ zeolites loaded with noble metals, e.g. ZSM-5, Beta, ITQ-2 |

Additional catalysts for use in the methods of the invention may be produced using chemical methods known in the art and/or purchased from commercial sources.

It will be understood that no particular limitation exists regarding the timing at which the additional catalysts may be applied when performing the methods of the invention. For example, the catalyst additive(s) may be added to the organic matter, solvent, pulping liquor, solid substrate, oil additive, or a mixture of one or more of these components (e.g. a slurry) before heating/pressurisation to target reaction temperature and pressure, during heating/pressurisation to target reaction temperature and pressure, and/or after reaction temperature and pressure are reached. The timing at which the additional catalyst is applied may depend on the reactivity of the feedstock utilised. For example, highly reactive feedstocks may benefit from applying the additional catalyst close to or at the target reaction temperature and pressure, whereas less reactive feedstocks may have a broader process window for applying the additional catalyst (i.e. the catalysts may be added prior to reaching target reaction temperature and pressure).

The additional catalysts may be included in a reaction mixture used for treatment according to the present invention prior to heating and/or pressurising the reaction mixture, during heating and/or pressurising of the reaction mixture, and/or after the reaction mixture reaches a desired reaction temperature and/or reaction pressure.

Oil Component

In some preferred embodiments of the invention, the slurry, the reaction mixture, or both comprises organic matter mixed with an oil additive. The oil additive may act as an oil-solvent in the reaction. The oil may be any suitable oil, non-limiting examples of which include paraffinic oil, gas-oil, crude oil, synthetic oil, coal-oil, bio-oil, shale oil/ kerogen oil, aromatic oils (i.e. single or multi-ringed components or mixtures thereof), tall oils, triglyceride oils, fatty acids, ether extractables, hexane extractables and any mixture of any of the previous components. The oil may be incorporated into the slurry mixture at any point before target reaction temperature and/or pressure are reached. For example, the oil may be added to the slurry in a slurry mixing tank. Additionally or alternatively, the oil may be added to the slurry en route to a reactor and/or during heating/pressurisation of the slurry.

In particularly preferred embodiments, the oil is a bio-oil product recycled from the process. For example, a portion of the bio-oil produced may be taken off as a side stream and recycled into the slurry, reaction mixture, or both.

In some preferred embodiments, the bio-oil is recycled in combination with solid substrate, each being a component of the bio-product. For example, a portion of the bio-oil produced mixed with solid substrate may be taken off as a side stream and recycled into the slurry, reaction mixture, or both.

No particular limitation exists regarding the proportion of oil additive in a slurry comprising organic matter treated in accordance with the methods of the present invention. For example, the slurry may comprise more than about 2 wt % oil, more than about 5 wt % oil, more than about 10 wt % oil, or more than about 20, 30, 40, 50, 60 or 70 wt % oil. Alternatively, the slurry may comprise less than about 98 wt % oil, less than about 95 wt % oil, less than about 90 wt % oil, or less than about 80, 70, 60, 50, 40 or 30 wt % oil.

In some preferred embodiments the slurry comprises between about 10 wt % and about 30 wt % organic matter, between about 2 wt % and about 15 wt % solid substrate, and between about 50 wt % and about 90 wt % solvent where the solvent is a mixture of oil and aqueous phase in any proportion.

In some preferred embodiments, the slurry comprises between about 40 wt % and about 50 wt % oil. In other preferred embodiments, the slurry comprises about 45 wt % oil.

In other preferred embodiments the slurry comprises a feedstock to oil ratio of 0.5-1.2:1. The oil may be paraffinic oil.

Reaction Conditions

In accordance with the methods of the present invention, organic matter feedstock (e.g. lignocellulosic matter and/or coal such as lignite) may be treated with a solvent in the presence of pulping liquor as described herein, and optionally in the presence of an oil additive, solid substrate, and/or additive catalysts, under conditions of increased temperature and pressure to produce bio-products.

The specific conditions of temperature and pressure used when practicing the methods of the invention may depend on a number different factors including, for example, the type of solvent used, the type of organic matter feedstock under treatment, the physical form of the organic matter feedstock under treatment, the relative proportions of components in the reaction mixture (e.g. the proportion of solvent, pulping liquor, organic matter feedstock, and optionally additive oil, catalyst additives, and/or any other additional component/s), the types of additive catalyst(s) utilised (if present), the retention time, and/or the type of apparatus in which the methods are performed. These and other factors may be varied in order to optimise a given set of conditions so as to maximise the yield and/or reduce the processing time. In preferred embodiments, all or substantially all of the organic material used as a feedstock is converted into bio-product(s).

Desired reaction conditions may be achieved, for example, by conducting the reaction in a suitable apparatus (e.g. a sub/supercritical reactor apparatus) capable of maintaining increased temperature and increased pressure.

Temperature and Pressure

According to the methods of the present invention a reaction mixture is provided and treated at a target temperature and pressure for a fixed time period ("retention time") facilitating the conversion of organic matter feedstock (e.g. lignocellulosic matter and/or coal such as lignite) into bio-product(s). The temperature and/or pressure required to drive conversion of organic feedstock into biofuel using the methods of the invention will depend on a number of factors including the type of organic matter under treatment and the relative proportions of components in the reaction (e.g. the proportion of solvent, pulping liquor, organic matter feedstock, and optionally additive oil, catalyst additives, and/or any other additional component/s), the type and amount of pulping liquor used, the retention time, and/or the type of apparatus in which the methods are performed. Based on the description of the invention provided herein the skilled addressee could readily determine appropriate reaction temperature and pressure for a given reaction mixture. For example, the optimal reaction temperature and/or pressure for a given feedstock slurry may be readily determined by the skilled addressee by preparing and running a series of reactions that differ only by temperature and/or pressure utilised and analysing the yield and/or quality of the target bio-product(s) produced. Proportions of relative components in the reaction mixture can be varied and the same tests conducted again at the same of different temperatures and/or pressures.

The skilled addressee will also recognise that the pressure utilised is a function of the slurry components and pressure drop, induced by the slurry, and strongly dependent on any particular reactor design (e.g. pipe diameter and/or length etc.).

In certain embodiments, treatment of organic matter feedstock to produce a bio-product using the methods of the invention may be conducted at temperature(s) of between about 150° C. and about 550° C. and pressure(s) of between about 10 bar and about 400 bar. Preferably, the reaction mixture is maintained at temperature(s) of between about 150° C. and about 500° C. and pressure(s) of between about 80 bar and about 350 bar. More preferably the reaction mixture is maintained at temperature(s) of between about 180° C. and about 400° C. and pressure(s) of between about 100 bar and about 330 bar. Still more preferably the reaction mixture is maintained at temperature(s) of between about 200° C. and about 380° C. and pressure(s) of between about 120 bar and about 250 bar.

In preferred embodiments, the reaction mixture is maintained at temperature(s) of between about 200° C. and about 400° C., and pressure(s) of between about 100 bar and about 300 bar.

In other preferred embodiments, the reaction mixture is maintained at temperature(s) of between about 250° C. and about 380° C., and pressure(s) of between about 50 bar and about 300 bar.

In other preferred embodiments, the reaction mixture is maintained at temperature(s) of between about 320° C. and about 360° C. and pressure(s) of between about 150 bar and about 250 bar. In other preferred embodiments, the reaction mixture is maintained at temperature(s) of between about 330° C. and about 350° C. and pressure(s) of between about 230 bar and about 250 bar. In another particularly preferred embodiment, the reaction mixture is maintained at temperature(s) of about 340° C. and pressure(s) of between about 240 bar.

In other preferred embodiments, the reaction mixture is maintained at temperature(s) of between about 320° C. and about 360° C., and pressure(s) of between about 220 bar and about 250 bar.

In certain embodiments, the reaction mixture is maintained at temperature(s) of above about 180° C. and pressure(s) above about 150 bar. In other embodiments, the reaction mixture is maintained at temperature(s) of above about 200° C. and pressure(s) above about 180 bar. In additional embodiments, reaction mixture is maintained at temperature(s) of above about 250° C. and pressure(s) above about 200 bar. In other embodiments, reaction mixture is maintained at temperature(s) of above about 300° C. and pressure(s) above about 250 bar. In other embodiments, reaction mixture is maintained at temperature(s) of above about 350° C. and pressure(s) above about 300 bar.

It will be understood that in certain embodiments a solvent used in the methods of the present invention may be heated and pressurised beyond its critical temperature and/or beyond its critical pressure (i.e. beyond the 'critical point' of the solvent). Accordingly, the solvent may be a 'supercritical' solvent if heated and pressurised beyond the 'critical point' of the solvent.

In certain embodiments a solvent used in the methods of the present invention may be heated and pressurised to level(s) below its critical temperature and pressure (i.e. below the 'critical point' of the solvent). Accordingly, the solvent may be a 'subcritical' solvent if its maximum temperature and/or maximum pressure is below that of its 'critical point'.

Preferably, the 'subcritical' solvent is heated and/or pressurised to level(s) approaching the 'critical point' of the solvent (e.g. between about 10° C. to about 50° C. below the critical temperature and/or between about 10 atmospheres to about 50 atmospheres below its critical pressure).

In some embodiments, a solvent used in the methods of the present invention may be heated and pressurised to levels both above and below its critical temperature and pressure (i.e. heated and/or pressurised both above and below the 'critical point' of the solvent at different times).

Accordingly, the solvent may oscillate between 'subcritical' and 'supercritical' states when performing the methods.

Retention Time

The specific time period over which the conversion of organic matter feedstock (e.g. lignocellulosic matter and/or coals such as lignite) may be achieved upon reaching a target temperature and pressure (i.e. the "retention time") may depend on a number different factors including, for example, the type of organic matter under treatment and the relative proportions of components in the reaction (e.g. the proportion of solvent, pulping liquor, organic matter feedstock, and optionally additive oil, catalyst additives, and/or any other additional component/s), and/or the type of apparatus in which the methods are performed. These and other factors may be varied in order to optimise a given method so as to maximise the yield and/or reduce the processing time. Preferably, the retention time is sufficient to convert all or substantially all of the organic material used as a feedstock into bio-product(s).

In certain embodiments, the retention time is less than about 60 minutes, 45 minutes, 30 minutes, 25 minutes, 20 minutes, 15 minutes, 10 minutes or less than about 5 minutes. In certain embodiments, the retention time is more than about 60 minutes, 45 minutes, 30 minutes, 25 minutes, 20 minutes, 15 minutes, 10 minutes or more than about 5 minutes. In other embodiments, the retention time is between about 1 minute and about 60 minutes. In additional embodiments, the retention time is between about 5 minutes and about 45 minutes, between about 5 minutes and about 35 minutes, between about 10 minutes and about 35 minutes, or between about 15 minutes and about 30 minutes. In further embodiments, the retention time is between about 20 minutes and about 30 minutes.

The optimal retention time for a given set of reaction conditions as described herein may be readily determined by the skilled addressee by preparing and running a series of reactions that differ only by the retention time, and analysing the yield and/or quality of bio-product(s) produced.

Heating/Cooling, Pressurisation/De-Pressurisation

A reaction mixture (e.g. in the form of a slurry) comprising organic matter feedstock (e.g. lignocellulosic matter and/or coals such as lignite), solvent, pulping liquor, and optionally one or more catalyst additives as defined herein may be brought to a target temperature and pressure (i.e. the temperature/pressure maintained for the "retention time") over a given time period.

Reaction mixes that do not contain a significant proportion of oil additive may require a very fast initial conversion to generate some solvent in-situ. However, the incorporation of oil into the reaction mixture as described herein allows the oil to act as an additional solvent thus alleviating the requirement for rapid heating/pressurisation.

In some embodiments, the reaction mix undergoes a separate pre-heating stage prior to reaching reaction temperature. The pre-heating stage may be performed on a feedstock slurry prior to the full reaction mix being formed. Alternatively the pre-heating stage may be performed on a slurry comprising all components of the reaction mixture. In some embodiments, the pre-heating stage raises the temperature of the feedstock slurry or reaction mixture to a maximum temperature of about: 120° C., 130° C., 140° C., 150° C., 160° C., 170° C., 180° C., 190° C., or 200° C. In other embodiments, the temperature is raised to less than about: 120° C., 130° C., 140° C., 150° C., 160° C., 170° C., 180° C., 190° C., or 200° C. In still other embodiments the temperature is raised to between about 100° C. and about 200° C., between about 100° C. and about 180° C., between about 100° C. and about 160° C., between about 120° C. and about 180° C., or between about 120° C. and about 160° C.

In continuous flow systems, pressure will generally change from atmospheric to target pressure during the time it takes to cross the pump (i.e. close to instantaneous) whereas in a batch system it may mirror the time that it takes to heat the mixture up.

In some embodiments, the reaction mixture may be brought to a target temperature and/or pressure in a time period of between about 30 seconds and about 30 minutes.

In some embodiments, the reaction mixture may be brought to a target temperature and/or pressure in a time period less than about 15 minutes, less than about 10 minutes, less than about 5 minutes, or less than about 2 minutes.

In certain embodiments, the reaction mixture may be brought to a target pressure substantially instantaneously and brought to a target temperature in less than about 20 minutes, less than about 10 minutes, or less than about 5 minutes. In other embodiments, the reaction mixture may be brought to a target pressure substantially instantaneously and brought to a target temperature in less than about two minutes. In other embodiments, the reaction mixture may be brought to a target pressure substantially instantaneously and brought to a target temperature in between about 1 and about 2 minutes.

Additionally or alternatively, following completion of the retention time period the product mixture generated may be cooled to between about 150° C. and about 200° C., between about 160° C. and about 200° C., preferably between about 170° C. and about 190° C., and more preferably about 180° C., in a time period of less than about 10 minutes, preferably less than about 7 minutes, more preferably less than about 6 minutes, preferably between about 4 and about 6 minutes, and more preferably about 5 minutes. Following the initial cooling period, the temperature may further reduced to ambient temperature with concurrent de-pressurisation by fast release into a cool aqueous medium (e.g. cooled water).

The processes of heating/pressurisation and cooling/de-pressurisation may be facilitated by performing the methods of the present invention in a continuous flow system (see section below entitled "Continuous flow").

Continuous Flow

Bio-product generation from organic matter feedstocks (e.g. lignocellulosic matter and/o coals such as lignite) using the methods of the present invention may be assisted by performing the methods under conditions of continuous flow.

Although the methods need not be performed under conditions of continuous flow, doing so may provide a number of advantageous effects. For example, continuous flow may facilitate the accelerated implementation and/or removal of heat and/or pressure applied to the slurry. This may assist in achieving the desired rates of mass and heat transfer, heating/cooling and/or pressurisation/de-pressurisation. Continuous flow may also allow the retention time to be tightly controlled. Without limitation to a particular mode of action, it is postulated that the increased speed of heating/cooling and/or pressurisation/de-pressurisation facilitated by continuous flow conditions along with the capacity to tightly regulate retention time assists in preventing the occurrence of undesirable side-reactions (e.g. polymerisation) as the slurry heats/pressurises and/or cools/de-pressurises. Continuous flow is also believed to enhance reactions responsible for conversion of organic matter to biofuel by virtue of generating mixing and shear forces believed to aid in emulsification which may be an important mechanism involved in the transport and "storage" of the oils generated away from the reactive surfaces of the feedstock as well as providing interface surface area for so-called 'on-water catalysis'.

Accordingly, in preferred embodiments the methods of the present invention are performed under conditions of continuous flow. As used herein, the term "continuous flow" refers to a process wherein organic matter feedstock mixed with a solvent and pulping liquor in the form of a slurry (which may further comprise any one or more of a solid substrate, an oil additive and/or a catalyst additive) is subjected to:

(a) heating and pressurisation to a target temperature and pressure, (b) treatment at target temperature(s) and pressure(s) for a defined time period (i.e. the "retention time"), and (c) cooling and de-pressurisation, while the slurry is maintained in a stream of continuous movement along the length (or partial length) of a given surface. It will be understood that "continuous flow" conditions as contemplated herein are defined by a starting point of heating and pressurisation (i.e. (a) above) and by an end point of cooling and de-pressurisation (i.e. (c) above).

Continuous flow conditions as contemplated herein imply no particular limitation regarding flow velocity of the slurry provided that it is maintained in a stream of continuous movement.

Preferably, the minimum (volume-independent) flow velocity of the slurry along a given surface exceeds the settling velocity of solid matter within the slurry (i.e. the terminal velocity at which a suspended particle having a density greater than the surrounding solution moves (by gravity) towards the bottom of the stream of slurry).

For example, the minimum flow velocity of the slurry may be above about 0.01 cm/s, above about 0.05 cm/s, preferably above about 0.5 cm/s and more preferably above about 1.5 cm/s. The upper flow velocity may be influenced by factors such as the volumetric flow rate and/or retention time. This in turn may be influenced by the components of a particular reactor apparatus utilised to maintain conditions of continuous flow.

Continuous flow conditions may be facilitated, for example, by performing the methods of the invention in a suitable reactor apparatus. A suitable reactor apparatus will generally comprise heating/cooling, pressurising/de-pressuring and reaction components in which a continuous stream of slurry is maintained.

The use of a suitable flow velocity (under conditions of continuous flow) may be advantageous in preventing scale-formation along the length of a particular surface that the slurry moves along (e.g. vessel walls of a reactor apparatus) and/or generating an effective mixing regime for efficient heat transfer into and within the slurry.

Bio-Products

The methods of the present invention may be used to produce bio-product(s) from organic matter feedstocks (e.g. lignocellulosic matter and/or coals such as lignite). The nature of the bio-product(s) may depend on a variety of different factors including, for example, the organic matter feedstock treated, and/or the reaction conditions/reagents utilised in the methods.

In certain embodiments, the bio-product(s) may comprise one or more biofuels (e.g. bio-oils, char products, gaseous products) and chemical products (e.g. platform chemicals, organic acids, furanics, furfural, hydroxymethylfurfural, levoglucosan, sorbitol, cylitol, arabinitol, formaldehyde, acetaldehyde).

In general, bio-product(s) produced in accordance with the methods of the present invention comprise or consist of a bio-oil. The bio-oil may comprise compounds including, but not limited to, any one or more of alkanes, alkenes, aldehydes, carboxylic acids, carbohydrates, phenols, furfurals, alcohols, and ketones. The bio-oil may comprise compounds including but not limited to aldehydes, carboxylic acids, carbohydrates, phenols, furfurals, alcohols, and ketones, resins and resin acids, and compounds structurally related to resin acids, alkanes and alkenes, fatty acids and fatty acid esters, sterols and sterol-related compounds, furanic oligomers, cyclopentanones, and cyclohexanones, alkyl- and alkoxy-cyclopentanones, and cyclohexanones, cyclopenteneones, alkyl- and alkoxy-cyclopentenones, aromatic compounds including naphthalenes and alkyl- and alkoxy-substituted naphthalenes, cresols, alkyl- and alkoxy-phenols, alkyl- and alkoxy-catechols, alkyl- and alkoxy-dihydroxybezenes, alkyl- and alkoxy-hydroquinones, indenes and indene-derivatives.

The bio-oil may comprise multiple phases, including but not limited to a water-soluble aqueous phase which may comprise, compounds including, but not limited to, any one or more of carbohydrates, aldehydes, carboxylic acids, carbohydrates, phenols, furfurals, alcohols, and ketones, resins and resin acids, and compounds structurally related to resin acids, alkanes and alkenes, fatty acids and fatty acid esters, sterols and sterol-related compounds, furanic oligomers, cyclopentanones, and cyclohexanones, alkyl- and alkoxy-cyclopentanones, and cyclohexanones, cyclopenteneones, alkyl- and alkoxy-cyclopentenones, aromatic compounds including naphthalenes and alkyl- and alkoxy-substituted naphthalenes, cresols, alkyl- and alkoxy-phenols, alkyl- and alkoxy-catechols, alkyl- and alkoxy-dihydroxybezenes, alkyl- and alkoxy-hydroquinones, indenes and indene-derivatives; and a water-insoluble phase which may comprise, compounds including, but not limited to, any one or more of waxes, aldehydes, carboxylic acids, carbohydrates, phenols, furfurals, alcohols, and ketones, resins and resin acids, and compounds structurally related to resin acids, alkanes and alkenes, fatty acids and fatty acid esters, sterols and sterol-related compounds, furanic oligomers, cyclopentanones, and cyclohexanones, alkyl- and alkoxy-cyclopentanones, and cyclohexanones, cyclopenteneones, alkyl- and alkoxy-cyclopentenones, aromatic compounds including naphthalenes and alkyl- and alkoxy-substituted naphthalenes, cresols, alkyl- and alkoxy-phenols, alkyl- and alkoxy-catechols, alkyl- and alkoxy-dihydroxybezenes, alkyl- and alkoxy-hydroquinones, indenes and indene-derivatives.

Other non-limiting examples of the bio-products include oil char (e.g. carbon char with bound oils), char, and gaseous product (e.g. methane, hydrogen, carbon monoxide and/or carbon dioxide, ethane, ethene, propene, propane).

In some embodiments, a biofuel may be produced from organic matter comprising lignocellulosic matter. The biofuel may comprise a liquid phase comprising bio-oil.

Biofuels (e.g. bio-oils) produced in accordance with the methods of the invention may comprise a number of advantageous features, non-limiting examples of which include reduced oxygen content, increased hydrogen content, increased energy content and increased stability. In addition, bio-oils produced by the methods of the invention may comprise a single oil phase containing the liquefaction product. The product may be separated from the oil phase using, for example, centrifugation eliminating the need to evaporate large amounts of water.

In some embodiments, a bio-oil product made in accordance with the methods of the present invention may be purified by dissolving the bio-oil in a purifying solvent followed by filtration of the resulting solution to remove particulates and insoluble material. Dissolving the bio-oil in the purifying solvent may have the effect of reducing the viscosity of the bio-oil which may assist the filtration process.

Optionally, the purifying solvent may be wholly or partly recovered by distillation following filtration, for example, by distillation under reduced pressure, thereby causing residual water in the oil to separate as a discrete phase, after which the water may be recovered by physical means such as decantation from the oil. If the purifying solvent used forms an azeotrope with water, this property may also be used to remove water from the bio-oil during the distillation processes.

Any purifying solvent in which the bio-oil dissolves may be used. Non-limiting examples of suitable purifying solvents include acetone, ethyl acetate, ethanol, benzene, toluene, xylene, tetralin, tetrahydrofuran, methyl ethyl ketone, dichloromethane, chloroform, ketones, alcohols, furans, and any combination thereof. Complex multicomponent purifying solvents may be used including, by way of non-limiting example only, light cycle oil, naphtha, and distilled fractions of bio-oil produced according to the methods of the present invention (i.e. a recycled bio-oil product) such as, for example, a fraction of the bio-oil with a boiling point between about 60° C. and about 150° C.).

A bio-oil bio-product produced in accordance with the methods of the invention may comprise an energy content of greater than about 25 MJ/kg, greater than about 30 MJ/kg, more preferably greater than about 32 MJ/kg, more preferably greater than about 35 MJ/kg, still more preferably greater than about 37 MJ/kg, 38 MJ/kg or 39 MJ/kg, and most preferably above about 41 MJ/kg. The bio-oil product may comprise less than about 20% oxygen, preferably less than about 15% wt db oxygen, more preferably less than about 10% wt db oxygen, still more preferably less than about 8% wt db oxygen, still more preferably less than about 7% wt db oxygen, and most preferably less than about 5% wt db oxygen. The bio-oil product may comprise greater than about 6% wt db hydrogen, preferably greater than about 7% wt db hydrogen, more preferably greater than about 8% wt db hydrogen, and still more preferably greater than about 9% wt db hydrogen. The molar hydrogen:carbon ratio of a bio-oil of the invention may be less than about 1.5, less than about 1.4, less than about 1.3, less than about 1.2, or about 1.0.

A bio-oil produced in accordance with the methods of the invention may comprise, for example, any one or more of the following classes of compounds: phenols, aromatic and aliphatic acids, ketones, aldehydes, hydrocarbons, alcohols, esters, ethers, furans, furfurals, terpenes, polycyclics, oligo- and polymers of each of the aforementioned classes, plant sterols, modified plant sterols, asphaltenes, pre-asphaltenes, and waxes.

A char or oil char bio-product produced in accordance with the methods of the invention may comprise an energy content of greater than about 20 MJ/kg, preferably greater than about 25 MJ/kg, more preferably greater than about 30 MJ/kg, and still more preferably greater than about 31 MJ/kg, 32 MJ/kg, 33 MJ/kg or 34 MJ/kg. The char or oil char product may comprise less than about 20% wt db oxygen, preferably less than about 15% wt db oxygen, more preferably less than about 10% wt db oxygen and still more preferably less than about 9% wt db oxygen. The char or oil char product may comprise greater than about 2% wt db hydrogen, preferably greater than about 3% wt db hydrogen, more preferably greater than about 4% wt db hydrogen, and still more preferably greater than about 5% wt db hydrogen. The molar hydrogen:carbon ratio of a char or oil char product of the invention may be less than about 1.0, less than about 0.9, less than about 0.8, less than about 0.7, or less than about 0.6.

An oil char bio-product produced in accordance with the methods of the invention may comprise, for example, any one or more of the following classes of compounds: phenols, aromatic and aliphatic acids, ketones, aldehydes, hydrocarbons, alcohols, esters, ethers, furans, furfurals, terpenes, polycyclics, oligo- and polymers of each of the aforementioned classes, asphaltenes, pre-asphaltenes, and waxes.

A char bio-product (upgraded PCI equivalent coal) produced in accordance with the methods of the invention may comprise, for example, a mixture of amorphous and graphitic carbon with end groups partially oxygenated, giving rise to surface carboxy- and alkoxy groups as well as carbonyl and esters.

Bio-products produced in accordance with the methods of the present invention may comprise one or more biofuels (e.g. bio-oils, char products, gaseous products) and chemical products (e.g. platform chemicals, organic acids, furanics, furfural, hydroxymethylfurfural, levoglucosan, sorbitol, cylitol, arabinitol, formaldehyde, acetaldehyde).

Bio-products produced in accordance with the methods of the present invention may be cleaned and/or separated into individual components using standard techniques known in the art.

For example, solid and liquid phases of biofuel products (e.g. from the conversion of coal) may be filtered through a pressure filter press, or rotary vacuum drum filter in a first stage of solid and liquid separation. The solid product obtained may include a high carbon char with bound oils. In certain embodiments, the oil may be separated from the char, for example, by thermal distillation or by solvent extraction. The liquid product obtained may contain a low percentage of light oils, which may be concentrated and recovered though an evaporator.

Bio-products produced in accordance with the methods of the present invention may be used in any number of applications. For example, biofuels may be blended with other fuels, including for example, ethanol, diesel and the like. Additionally or alternatively, the biofuels may be upgraded into higher fuel products. Additionally or alternatively, the biofuels may be used directly, for example, as petroleum products and the like.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

EXAMPLES

The invention will now be described with reference to specific examples, which should not be construed as in any way limiting.

In the following Examples, the thermochemical conversion process utilised is also referred to as "Cat-HTR".

Example 1: Bio-Oil Production from Feedstocks Using Black Liquor Additive

Materials and Methods

Australian *Radiata* pine was run with black liquor to establish the catalytic action of black liquor and suitable operating temperatures. In the same manner, hog fuel trials were run alternately using sodium hydroxide and then with black liquor. Finally, mixed feedstocks containing hog fuel, SPF wood chip, and paper sludge were processed with black liquor.

Pre-processing trials were conducted on the feedstocks to prepare them to specifications of the small pilot plant (SPP). Dry-milling of the feedstocks followed by Cat-HTR processing in the small pilot plant led to successful production of bio-crude (bio-oil) from the feedstocks, in particular from a mixture of hog fuel, SPF wood chip, sludge and black liquor.

The resulting bio-crudes had gross calorific values (GCV) on a dry ash free basis in the range of 33-36 MJ/kg. For comparison, diesel fuel has a GCV (or energy content) of about 45 MJ/kg and unprocessed dry wood about 18-21 MJ/kg. Licella has demonstrated that distilled bio-crudes from *Radiata* pine wood flour with initial energy contents in this range can be successfully hydroprocessed to give hydrocarbons compatible with refinery streams at an advanced stage of processing to finished fuels. It was confirmed in the trials that the alkaline inorganic components of black liquor are capable of substituting for the alkaline catalysts typically used by Licella in order to produce high energy density bio-crudes. That is, as well as supplying liquid phase biomass to the reactors, the black liquor can obviate the need to add additional alkaline catalysts in the Cat-HTR process. The highest proportion of black liquor used in testing was approximately 1 part of dry wood feedstock to 0.65 parts of black liquor (analysis as per table 4). The highest level of black liquor used was determined in this instance by the level of sulphur compatible with the materials of construction of the SPP and the expected levels of hydrogen sulphide in the producer gas, consistent with safe operation of the plant.

Summary of Feedstock Trials
Feedstock Preparation
Feedstocks utilised were:
  SPF wood chip (spruce-fir-pine wood chip)
  Hog fuel (wood residue including wood chips, bark, and the like)
  Paper sludge
  Black liquor Approximately 100 kg on a dry basis of each solid feedstock was obtained. Most types of feedstock required some degree of preparation before processing. Solid materials are processed as slurries in water or other solvents, and the particle size of the solid materials is of a size suitable for producing a slurry that can be pumped at high pressure. The small pilot plant (SPP), due to its small pump valve orifices, requires a greater degree of comminution of the feedstock than would a commercial facility. For the SPP, specifically, it is preferred to reduce to the maximum particle size to about 150 microns diameter. Both wet and dry grinding have been utilized, and dry grinding has usually been employed for the smaller particle sized required for the SPP.

Solid Feedstock Preparation

Subsequent to the wet-grinding activities, dry grinding of the wood chip, hog fuel and sludge feedstocks was carried out by a contracted firm Aximill, using modified compressed air jet mills, reference http://www.aximill.com. The feedstock is supplied at approximately 10% moisture (however all feedstock mass within this report is quoted on a dry basis). The particle size is reduced to sub 130 micron, typical particle size distribution data is available upon request (however this feedstock is peculiar to the requirements of the SPP and unlikely to be of interests in subsequent large scale testing). The tested feedstock analysis is presented below, including proximate, ultimate, and ash constituent analyses in the feedstock analysis section of this document.

Black Liquor Preparation for Cat-HTR

As received black liquor (per Table 4) was diluted 100% with water by volume. The diluted mixture was filtered through a 250 micron sieve to remove oversize particles and contaminants such as plastic and wood chips etc. to be compliant with pump specifications on the small pilot plant. The amount of material removed was a negligible fraction of the overall sample. The filtered, diluted black liquor was then used as a stock liquor for addition at various levels to other feedstocks for Cat-HTR. This stock liquor is referred to as 'stock black liquor'.

TABLE 2

Properties of Stock Black Liquor

| | | |
|---|---|---|
| The properties of this stock black liquor are | 1.14 | SG of stock black liquor (diluted mixture) kg/L |
| 1 kg Stock Black Liquor Contains: | 0.439 | L of black liquor (per Table 4) |
| 1 kg Stock Black Liquor Contains: | 0.561 | kg of black liquor (per Table 4) |

Run Summary

A detailed description of individual runs is provided in Example 2. Table 3 below gives a summary of all experiments conducted during the course of this study, irrespective of outcome.

TABLE 3

Summary of run conditions

| Run ID No. | Feedstock | Liquid Catalyst | Summary | Outcome |
|---|---|---|---|---|
| 20140521 | 8% Licella radiata pine *note1 | 1 kg stock black liquor per dry kg wood | Successful trial on dry ground radiata pine and black liquor | Successful |
| 20140523 | 8% Licella radiata pine *note1 | 1.3 kg stock black liquor per dry kg wood | Successful trial on dry ground radiata pine and a higher concentration of black liquor | Successful |
| 20140716 | 7.8% hog fuel | 12% sodium hydroxide | Successful trial on dry ground hog fuel slurry. | Successful |
| 20140724 | 8% hog fuel | 1.3 kg stock black liquor per dry kg wood | Successful trial on dry ground hog fuel slurry. | Successful |
| 20140731 | 6.4% hog fuel, 1.44% wood, 0.16% sludge | 1.3 kg stock black liquor per dry kg mix | Successful trial on dry ground mixed component slurry. | Successful |
| 20140814 | 6.4% hog fuel, 1.44% wood, 0.16% sludge | 1.3 kg stock black liquor per dry kg mix | Successful trial on dry ground mixed component slurry. | Successful |

Chemical Analysis

Proximate Analysis

Proximate Analysis methods for Bio-Crude and feedstocks.

Weigh and heat a sample in a crucible at 900° C., volatile matter and fixed carbon are determined according to AS2434.2. Volatile matter and fixed carbon are stated for feedstocks only.

Solid feedstock and oil product ash yield is performed according to HRL method 1.6. The sample is held at 815° C. in an open crucible until the weight is stable.

The results of a proximate analysis are ash content, volatile mater and fixed carbon which are determined as percentages of the sample mass, on dry basis. Results allow for an estimate of the "reactivity" of feedstocks, and amount of "solids" expected.

Ultimate Analysis

Ultimate analysis is performed by HRL method 1.4 sample in a CHN analyser.

Ultimate analysis is a breakdown of the sample in its most important elements—carbon, hydrogen, nitrogen, sulphur and oxygen. The oxygen content is a key indicator as it is inversely correlated to the energy content of the sample. The Cat-HTR process can be operated in a way to retain or to remove oxygen according to the operating conditions. Depending on the target chemical fractions or purpose of the bio-crude, the remaining oxygen may be reduced at the refinery stage by hydrogenation to obtain the highest energy density; or the oxygen is maintained within the bio-crude as an oxygenated chemical feedstock containing phenols (for resins and plasticisers and chemical precursors of pharmaceuticals). The hydrogen and the carbon are the main contributors to the energy content of the bio-crude. Sulphur is of interest for materials selection on the Cat-HTR plant, it is a factor that influences capital cost of Cat-HTR plant. Sulphur in the bio-crude can be removed, along with oxygen and nitrogen in a hydroprocessing unit of a refinery or a dedicated hydrotreater. Sulphur is measured by HRL method 1.14 in an ICP or sulphur analyser mounted within a furnace. Sulphur levels in the oil product are measured by USEPA method 5050. The gross calorific value is a direct result of the composition. It represents the energy available from combustion of the sample. Chlorine is measured as high levels of chlorine or chloride have potential to corrode plant steels.

Ash composition is a measure of inorganic components present in the samples, for general feedstock and product quality assessment. Lignocellulosic materials including black liquor contain inorganic compounds, and some of the insoluble inorganics are expected to be carried over to the bio-crude product. Prior to further refining, e.g. by hydroprocessing, the ash should be removed, as some ash components are likely to adversely affect the catalysts used in hydroprocessing. Distillation is the most common way to do this, and a key difference between bio-crudes from Cat-HTR and pyrolysis bio-oils from e.g. fast pyrolysis is that the bio-crudes can be distilled but the pyrolysis oils cannot. This is because pyrolysis oils have high oxygen contents and low stability. Ash content of bio-crude may be removed by a distillation process at the front end of a refinery. Ash content is reported as a percentage on dry basis, the ash composition as reported in this document assumes that the inorganics are in their oxide forms. This assumption may mean that the sum of ash composition may exceed 100% and some other inorganics might not be accounted for.

Solvent Extraction

Solvent extraction is performed on a measured amount of the water phase product using diethyl ether to dissolve and separate recoverable oils from the water phase. Ether extraction produces results quantifying both the ether extractable chemicals and the residues of ether extraction.

Ether extractable chemicals are oils that are lighter fractions including alcohols, ketones, phenols and short chain hydrocarbons. Many of the phenols are used in the flavouring and essence industries. Solvent extraction is used as a rapid method of quantifying these organic components, that are potentially recoverable in a commercial plant, thereby adding to the overall oil yield and possibly representing an additional product stream of interest to the fine chemicals industry.

Residue from the extraction includes soluble ash from the feedstock, catalyst and water soluble (non-ether soluble) organics. The latter group includes glycolic and lactic acids, used respectively in the cosmetics and biopolymers industries. The catalyst can be regenerated, however, as it is inexpensive the choice between regenerating the catalyst and treating and disposing of the brine generated is influenced by site-specific factors. Potassium-based catalysts can also be used, in which case the catalyst residues plus additional potassium from the biomass may find application as fertilizer products.

Method of Ether Extraction

Weigh 100 g of sample.

Acidify to pH around 5, using sulphuric acid.

Add 100 to 150 ml ether.

Shake not stir.

Settle for 10 minutes, watching for separation by density.

Drain water off the bottom.

Pour ether into an evaporator flask, weighed before and after collection of ether extractables.

The ether extraction cycle is performed 3 times, on the same water, using fresh ether each time.

Residues are extracted from the water by drying at 110° C. in air and collecting (weighing) the solids.

There are some water soluble compounds derived from the wood that are not assessed by these methods, e.g. low molecular weight alcohols and ketones such as methanol, ethanol, and acetone. These compounds are known from 1H NMR and GC analysis to be present in significant quantity Cat-HTR liquors when *Radiata* pine is processed. Based on quantitation from previous studies on *Radiata* pine, a contribution to the mass balance of 6% of the organic material present in the feedstock has been included in the mass balances in this report.

Water Analysis

In addition to the gravimetric analysis by solvent extraction described above, water samples were analysed by Envirolab Services for a range of water quality parameters.

Results

TABLE 4

Feedstock Analysis Results

| | | Radiata Pine | Spruce Pine Fir | Hogfuel | Black Liquor |
|---|---|---|---|---|---|
| Proximate Analysis | Moisture (% wt ar) | 5.7 | 43.8 | 60.0 | 53.9 |
| | Ash (% wt db) | 0.6 | 0.6 | 2.2 | 47.1 |
| | Volatiles (% wt db) | 79.8 | 79.5 | 79.4 | |
| | Fixed C. (% wt db) | 19.7 | 19.9 | 23.5 | |

TABLE 4-continued

Feedstock Analysis Results

|  |  | Radiata Pine | Spruce Pine Fir | Hogfuel | Black Liquor |
|---|---|---|---|---|---|
| Ultimate Analysis | GCV (MJ/kg db) | 20.8 | 18.6 |  |  |
|  | GCV (MJ/kg daf) | 21.0 | 18.7 |  |  |
|  | Carbon (% wt db) | 52.3 | 52.1 | 52.9 | 37.5 |
|  | Hydrogen (% wt db) | 6.2 | 6.3 | 6.0 | 1.7 |
|  | Nitrogen (% wt db) | 0.06 | 0.21 | 0.25 | <0.01 |
|  | Sulphur (% wt db) | 0.01 | 0.01 | 0.02 | 4.77 |
|  | Oxygen (% wt db) | 40.8 | 40.8 | 38.7 | 3.2 |
|  | Chlorine (%) |  |  |  | 0.21 |
|  | Molar H/C Ratio | 1.4 |  |  | 0.04 |
| Ash Constituents (% oxide in ash) | SiO2 (% wt db) |  | 2.3 | 1.1 |  |
|  | Al2O3 (% wt db) |  | 1.1 | 0.62 |  |
|  | Fe2O3 (% wt db) |  | 0.69 | 0.28 |  |
|  | TiO2 (% wt db) |  | 0.04 | 0.02 |  |
|  | K2O (% wt db) |  | 16.3 | 7.6 |  |
|  | MgO (% wt db) |  | 7.9 | 3.2 |  |
|  | Na2O (% wt db) |  | 0.42 | 0.3 |  |
|  | CaO (% wt db) |  | 33.9 | 46.7 |  |
|  | SO3 (% wt db) |  | 1.2 | 1 |  |
|  | P2O5 (% wt db) |  | 2.2 | 2.5 |  |
|  | Mn3O4 (% wt db) |  | 2.3 | 1.5 |  |
|  | SrO (% wt db) |  | 0.12 | 0.24 |  |
|  | BaO (% wt db) |  | 0.3 | 0.6 |  |
|  | ZnO (% wt db) |  | 0.28 | 0.42 |  |
|  | CuO (% wt db) |  | 0.2 | 0.06 |  |
|  | Cr2O3 (% wt db) |  | 0.04 | 0 |  |
|  | Co3O4 (% wt db) |  | 0 | 0 |  |
|  | NiO (% wt db) |  | 0.02 | 0 |  |
|  | V2O5 (% wt db) |  | 0 | 0 |  |

Comparison of Feedstocks

*Radiata* Pine wood flour was used as a benchmark feedstock for biomass Cat-HTR. The SPF woodchip is unsurprisingly quite similar to the *Radiata* Pine in terms of proximate and ultimate analyses. The Hog Fuel has a higher ash content than either of the foregoing feedstocks, this is likely attributable to higher levels of bark, needles and other contaminants. The ash is dominated by calcium, which is basic under most conditions, and may have a catalytic effect in Cat-HTR. The sludge has a high ash content and the composition of the ash is dominated by calcium, which again may have a catalytic effect in Cat-HTR. The mixed feedstock used in the last two runs listed in table 3 can be expected to be dominated by the hog fuel and black liquor properties that comprise most of the feed.

One subtle but potentially significant difference between runs with sodium hydroxide as catalyst and with black liquor as catalyst is the point at which the catalyst is added into the process. In the SPP sodium hydroxide catalyst is normally injected at high pressure, after preheating of the feedstock slurry and mixing with the steam to heat the slurry to reaction temperature have occurred. In contrast, the black liquor trials have black liquor premixed into the slurry in the atmospheric pressure slurry mixing tank. The slurry and black liquor mixture passes through the main slurry high pressure pump, through the preheaters and through to the steam injection point. There it gains its final temperature for entry into the reactors. A consequence of the different processing approach is that the slurries containing the black liquor can be expected to start reacting earlier in the Cat-HTR process than those where the catalyst is added at a later point.

Trial Results

TABLE 5

Summary of experimental trials liquids mass balance

| Run ID No. | 20140521 | 20140523 | 20140716 | 20140724 | 20140731 | 20140814 |
|---|---|---|---|---|---|---|
| Feedstock | 8% Licella radiata pine | 8% Licella radiata pine | 7.8% hog fuel | 8% hog fuel | 6.4% hog fuel, 1.44% wood, 0.16% sludge | 6.4% hog fuel, 1.44% wood, 0.16% sludge |
| Liquid Catalyst | 1 kg diluted black liquor per dry kg wood | 1.3 kg diluted black liquor per dry kg wood | 12% sodium hydroxide | 1.3 kg diluted black liquor per dry kg wood | 1.3 kg diluted black liquor per dry kg mix | 1.3 kg diluted black liquor per dry kg mix |
| T4 Injection time (mins) | 67 | 71 | 68 | 92 | 83 | 61 |
| Percent solids in feed | 9.96% | 10.49% | 7.8% | 10.5% | 9.9% | 9.7% |
| Percent solids in reactors | 4.0% | 4.2% | 2.9% | 4.3% | 4.0% | 3.5% |
| Solids in feed (kg) | 4.1 | 4.5 | 2.8 | 6.2 | 5.0 | 3.0 |
| Product recovered (wet kg) | 1.085 | 1.118 | 0.763 | 1.258 | 1.134 | 0.521 |
| Moisture content of oil (%) | 12.4% | 18.5% | 14.7% | 16.7% | 12.9% | 20.1% |
| Bio crude recovered (dry kg) | 0.951 | 0.912 | 0.651 | 1.048 | 0.988 | 0.416 |
| Bio crude yield (dry) | 23.0% | 20.4% | 23.3% | 17.0% | 19.6% | 13.7% |
| NCG gas measured (m3/hr) | 0.43 | 0.43 | 0.34 | 0.43 | 0.47 | 0.42 |
| NCG density (kg/m3) | 1.59 | 1.55 | 1.23 | 1.60 | 1.60 | 1.52 |
| NCG (kg/hr) | 0.830 | 0.809 | 0.515 | 0.835 | 0.914 | 0.784 |

TABLE 5-continued

Summary of experimental trials liquids mass balance

| Run ID No. | 20140521 | 20140523 | 20140716 | 20140724 | 20140731 | 20140814 |
|---|---|---|---|---|---|---|
| Solids in feed (kg/hr) | 3.709 | 3.767 | 2.434 | 4.018 | 3.635 | 2.990 |
| NCG Yield | 22.4% | 21.5% | 21.2% | 20.8% | 25.1% | 26.2% |
| Total feed to T4 - NCG (kg) | 103.7 | 104.4 | 93.6 | 141.5 | 124.4 | 85.5 |
| Ether extractable in liquor (%) | 0.48% | 0.56% | 0.394% | 0.402% | 1.440% | 0.574% |
| Ether extractable in liquor (kg) | 0.49 | 0.59 | 0.37 | 0.57 | 1.79 | 0.49 |
| Ether extractable yield | 11.9% | 13.2% | 13.2% | 9.2% | 35.6% | 16.1% |
| Solid residue in liquor (%) | 0.64% | 1.05% | 1.40% | 0.81% | 0.88% | 0.66% |
| Solid residue in liquor (kg) | 0.66 | 1.09 | 1.31 | 1.15 | 1.10 | 0.56 |
| Solid residue from catalyst (kg) | 0 | 0 | 0.34 | 0.00 | 0.00 | 0.00 |
| Solid residue in liquor yield | 16.0% | 24.5% | 34.9% | 18.7% | 21.8% | 18.4% |
| % black liquor solids in feed | 25.6% | 30.9% | 0.0% | 31.0% | 30.9% | 30.9% |
| % Inorganic material in feed | 12.1% | 14.5% | 0.0% | 14.6% | 15.9% | 15.9% |
| Organic material in feed (kg) | 3.64 | 3.81 | 2.79 | 5.26 | 4.23 | 4.23 |
| Methanol ethanol & acetone yield (kg) | 0.22 | 0.23 | 0.17 | 0.32 | 0.25 | 0.25 |
| Methanol, ethanol & acetone yield (%) | 5.28% | 5.13% | 6.00% | 5.13% | 5.04% | 5.04% |
| Yield Summary | | | | | | |
| Oil Yield (dry) | 23.0% | 20.4% | 23.3% | 17.0% | 19.6% | 13.7% |
| NCG Yield | 22.4% | 21.5% | 21.2% | 20.8% | 25.1% | 26.2% |
| Ether extractable yield | 11.9% | 13.2% | 13.2% | 9.2% | 35.6% | 16.1% |
| Solid residue in liquor yield | 16.0% | 24.5% | 34.9% | 18.7% | 21.8% | 18.4% |
| Methanol, ethanol & acetone yield (%) | 5.3% | 5.1% | 6.0% | 5.1% | 5.0% | 5.0% |
| Total | 78.54% | 84.76% | 98.58% | 70.87% | 107.24% | 79.54% |
| Cooler inlet temp | 335 | 335 | 315 | 315 | 310 | 335 |
| Estimated mixing(Reactor inlet) temp | 355 | 355 | 335 | 335 | 330 | 355 |
| Liquor pH | 5.59 | 7.17 | 8.18 | 7.15 | 7.09 | 7.07 |

TABLE 6

Summary of Cat-HTR trials non-condensable gases

| | Run ID No. | Methane | Carbon Monoxide | Hydrogen | Ethylene | Ethane | Propylene | Propane | Carbon Dioxide | H2S (ppm) | HHV (MJ/kg) | NCG Yield |
|---|---|---|---|---|---|---|---|---|---|---|---|---|
| R pine + 1:1 black liquor | 20140521 | 4.51% | 0.11% | 10.11% | 0.43% | 0.69% | 1.84% | 0.37% | 81.68% | 2537 | 3.50 | 22.37% |
| R pine + 1:1.3 black liquor | 20140523 | 5.34% | 0.05% | 12.00% | 0.37% | 0.83% | 1.60% | 0.38% | 79.21% | 2173 | 3.84 | 21.48% |
| Hogfuel + catalyst | 20140716 | 3.69% | 0.01% | 31.24% | 0.36% | 0.58% | 1.04% | 0.38% | 62.71% | <150 | 5.61 | 21.16% |
| Hogfuel + BL | 20140724 | 5.00% | 0.05% | 9.56% | 0.29% | 0.71% | 1.59% | 0.38% | 82.23% | 1779 | 3.40 | 20.79% |
| Full mix | 20140731 | 4.79% | 0.04% | 9.74% | 0.28% | 0.77% | 1.46% | 0.41% | 82.32% | 1749 | 3.33 | 25.15% |
| Full mix higher temp | 20140814 | 5.12% | 0.04% | 13.75% | 0.36% | 0.86% | 1.36% | 0.38% | 77.93% | 2582 | 3.88 | 26.24% |

The mass balances are closed to the extent that 79-107% of the mass of feedstock entering the Cat-HTR reactor during a certain steady state period of operation has been identified in the products collected from the tank in which it was captured (known as T4) or the gas stream venting from it. The exception is the run of 24/07/14 (hog fuel plus black liquor) which was very poorly closed. Typically with *radiata* pine wood flour runs we expect the mass balance to close in the vicinity of 85-100%. It should be noted that the mass balances are approximate only and are based on a number of simplifications and approximations, for the reason that it is not possible to quantify every component in the complex.

The wider variation in the extent of closure of the mass balance in with the feedstocks is most probably related to the greater complexity of the black liquor's inorganic components and the resulting uncertainty in the water phase composition.

Bio-Crude Yields

Typical bio-crude yields from a *Radiata* pine wood flour feedstock in the Small Pilot Plant are mid-to-low twenties percent on a dry wood feed basis. Those yields are lower than obtained in Licella's Larger Pilot Plants which are typically around mid-thirties percent or more.

The main reason for the difference is the lower maximum slurry concentrations that can be pumped in the SPP, and the amount of steam used for heating the slurry to reaction temperature, which is much larger for the SPP than for the LPP. Generally, higher concentrations of biomass in the Cat-HTR reactor (and lower concentrations of water) favour higher yields of bio-crude at the expense of the proportion of the organic material that dissolves in the water phase.

Superficially, conversion of around ⅓ of the feed biomass to bio-crude may like quite a low yield, however, considerable energy densification has occurred in that step by removal of oxygen. More than half of mass of the sugar polymers comprising hemicellulose and cellulose is oxygen. The oxygen is removed mainly as carbon dioxide gas but also as salts of small carboxylic acids such as sodium acetate which dissolve in the water phase. A rule of thumb for the fate of woody biomass in Cat-HTR is that one third of the mass is converted to biocrude, one third to gas, mainly CO2, and one third to water soluble chemicals. The bio-crude yields from the feedstocks are generally in line with those expected from the SPP, with the exception of 14/08/14 run where the amount of bio-crude recovered was low. The reason for this is unknown, but it is likely that some bio-crude was trapped in the apparatus and not recovered.

Gas Yields & Compositions

Generally, non-condensable gas (NCG) yields are slightly lower for all experiments than typical (30%) for *Radiata*

Pine wood flour under conditions of 12% catalyst loading, 240 bar pressure and 340 degrees. In the case of the *radiata* pine plus black liquor runs this is likely due to slightly lower gasification activity of the black liquor derived catalysts and to the reduced proportion of cellulose (black liquor contains mostly lignin and hemicellulose as organic components) compared to *radiata* pine wood flour. In the case of the hog fuel dominated runs the lower NCG make is probably also related to the lower temperature reaction temperatures chosen. The main difference in gas composition between sodium hydroxide catalysed runs and black liquor catalysed runs is that the hydrogen make is lower and the hydrogen sulphide make is higher for the latter systems. The H2S make for sodium hydroxide catalysed systems with *radiata* pine feed is essentially negligible. The proportion of H2S in the gas is not a simple function of black liquor concentration, as can be seen from the first two entries in tables 5 and 6. This is possibly a function of the pH of the aqueous phase. A typical wood+sodium hydroxide catalyst product by Licella produces approximately 20% $H_2$ by volume in the non-condensable gas product. The hog fuel+sodium hydroxide run produced a greater fraction of $H_2$ than this, possibly indicating that the ash components in the hog fuel have some catalytic activity in gasification.

Water-Phase Components

The water-soluble components have the greatest uncertainty associated with them, particularly in the case of those runs utilizing black liquor. In the case of *radiata* pine plus sodium hydroxide catalyst, the dominant water soluble components are acetates, hydrogen carbonates, phenols, ketones, catechols, ethanol and methanol, and humic materials (brown water soluble compounds, insoluble in diethyl ether). In the case of the black liquor as catalyst, the water soluble chemistry is likely to be more complex still.

The Ultimate and Proximate analysis of bio-crude product is tabulated below, providing direct comparison of all successful Cat-HTR trials. Individual runs are described in Table 7.

TABLE 7

Summary of Experimental Trials Bio-Crude Product

| | Description | Radiata Pine BL 20140521 | Radiata Pine BL 20140523 | Hog Fuel + Catalyst 20140716 | Hog Fuel + BL 20140724 | Mixed Feed + BL 20140731 | Mixed Feed + BL 20140814 | Radiata Pine Typical |
|---|---|---|---|---|---|---|---|---|
| Proximate Analysis | Moisture (% wt ar) | 8 | 1.6 | | 6 | 7.5 | 4 | |
| | Ash (% wt db) | 0.5 | 0.4 | 6.6 | 2.8 | 2.6 | 2.0 | |
| | Volatiles (% wt db) | | | | | | | 0.79 |
| | Fixed C. (% wt db) | | | | | | | |
| Ultimate Analysis | GCV (MJ/kg db) | 34.8 | 34.2 | 33.9 | 32.6 | 33.0 | 33.0 | |
| | GCV (MJ/kg daf) | 34.97 | 34.34 | 36.29 | 33.50 | 33.89 | 33.66 | 33.50 |
| | Carbon (% wt db) | 73.4 | 80.3 | 76.7 | 75.1 | 79.2 | 77.6 | 33.8 |
| | Hydrogen (% wt db) | 6.5 | 7.2 | 7.2 | 6.6 | 6.4 | 6.9 | |
| | Nitrogen (% wt db) | 0.1 | 0.2 | 0.3 | 0.3 | 0.4 | 0.3 | |
| | Sulphur (% wt db) | 0.6 | 0.7 | 0.1 | 1.1 | 0.6 | 0.6 | |
| | Oxygen (% wt db) | 18.9 | 13.0 | 9.6 | 12.7 | 10.2 | 12.4 | |
| | Chlorine (%) | | | | | | | |
| | Molar H/C Ratio | | | | | | | |
| Ash Constituents (% oxide in ash) | $SiO_2$ (% wt db) | 3.6 | 5.4 | 0.8 | 3 | 3.3 | 3.3 | |
| | $Al_2O_3$ (% wt db) | 4.4 | 3.9 | 1.7 | 3.7 | 4.9 | 5 | |
| | $Fe_2O_3$ (% wt db) | 5.6 | 2.5 | 1.4 | 9.9 | 6.6 | 5.1 | |
| | $TiO_2$ (% wt db) | 0.08 | 0.07 | 0.05 | 0.13 | 0.15 | 0.21 | |
| | $K_2O$ (% wt db) | 1.4 | 3.7 | 0.34 | 0.44 | 0.72 | 0.81 | |
| | MgO (% wt db) | 1.7 | 2 | 3.7 | 3.7 | 4.8 | 4.8 | |
| | $Na_2O$ (% wt db) | 13.1 | 27.9 | 7.2 | 3.6 | 5.5 | 6.7 | |
| | CaO (% wt db) | 3.2 | 3.7 | 46.6 | 36.2 | 42.1 | 42.4 | |
| | $SO_3$ (% wt db) | 19.1 | 38 | 1.1 | 24.3 | 20.6 | 19.9 | |
| | $P_2O_5$ (% wt db) | 0.6 | 0.51 | 2.5 | 3.6 | 3.5 | 3.5 | |

TABLE 7-continued

Summary of Experimental Trials Bio-Crude Product

| Description | Radiata Pine BL 20140521 | Radiata Pine BL 20140523 | Hog Fuel + Catalyst 20140716 | Hog Fuel + BL 20140724 | Mixed Feed + BL 20140731 | Mixed Feed + BL 20140814 | Radiata Pine Typical |
|---|---|---|---|---|---|---|---|
| Mn3O4 (% wt db) | 0.24 | 0.32 | 1.17 | 1.39 | 0.3 | 0.3 | |
| SrO (% wt db) | <0.01 | <0.01 | 0.17 | 0.17 | 0.6 | 0.5 | |
| BaO (% wt db) | 0.04 | 0.04 | 0.4 | 0.5 | <0.1 | 0.1 | |
| ZnO (% wt db) | 0.2 | 0.16 | 0.31 | 0.56 | <0.1 | <0.1 | |
| CuO (% wt db) | 0.36 | 0.32 | 0.11 | 0.17 | 0.2 | 0.2 | |
| Cr2O3 (% wt db) | 0.16 | 0.07 | 0.02 | 0.02 | 1.7 | 2.3 | |
| Co3O4 (% wt db) | 0 | 0 | <0.1 | <0.1 | <0.1 | <0.1 | |
| NiO (% wt db) | 0.04 | 0.05 | 0.02 | 0.02 | <0.1 | <0.1 | |
| V2O5 (% wt db) | 0.52 | 0.09 | 0 | 0 | 0.5 | 0.6 | |

*Radiata* Pine Wood Flour with Black Liquor 20140521

Operating Conditions (Wood Flour w/-Black Liquor 20140521)

Table 8 below shows the operating conditions of the mass balance run on *Radiata* Pine Wood Flour. This run produced the samples of Bio-Crude Oil, syngas and water, that are presented in the next section.

TABLE 8

Cat-HTR Operating Conditions, Radiata Wood Flour 20140521

| | |
|---|---|
| Reactor Temperature | 355° C. |
| Reactor Pressure | 220 to 249 bar |
| Reactor Residence Time | 25 minutes |

Mass Balance (Wood Flour w/-Black Liquor 20140521)

A product mass balance summary of the trial is provided in Table 9 below. 4.1 kg of Stock Black liquor was used in this feedstock slurry (1:1 by mass db).

TABLE 9

Wood Flour Black Liquor Mass Balance 20140521

| | |
|---|---|
| Date | 20140521 |
| Feedstock | 8% Licella radiata pine |
| Liquid Catalyst | 1 kg stock black liquor per dry kg wood |
| T4 Injection time (mins) | 67 |
| Percent Solids in Feed | 9.96% |
| Percent solids in reactors | 4.0% |
| Solids in feed (kg) | 4.1 |
| product recovered (wet kg) | 1.085 |
| Moisture content of oil (%) | 12.4% |

TABLE 9-continued

Wood Flour Black Liquor Mass Balance 20140521

| | |
|---|---|
| Bio crude recovered (dry kg) | 0.951 |
| Bio crude yield (dry) | 23.0% |
| NCG gas measured (m3/hr) | 0.43 |
| NCG density (kg/m3) | 1.59 |
| NCG (kg/hr) | 0.830 |
| Solids in feed (kg/hr) | 3.709 |
| NCG yield | 22.4% |
| Total feed to T4 - NCG (kg) | 103.7 |
| Ether extractable in liquor (%) | 0.48% |
| Ether extractable in liquor (kg) | 0.49 |
| Ether extractable yield | 11.9% |
| Solid residue in liquor (%) | 0.64% |
| Solid residue in liquor (kg) | 0.66 |
| Solid residue from catalyst (kg) | 0 |
| Solid residue in liquor yield | 16.0% |
| % black liquor solids in feed | 25.6% |
| % Inorganic material in feed | 12.1% |
| Organic material in feed (kg) | 3.64 |
| Methanol ethanol & acetone yield (kg) | 0.22 |
| Methanol, ethanol & acetone yield (%) | 5.28% |
| Yield Summary | |
| Bio crude yield (dry) | 23.0% |
| NCG yield | 22.4% |
| Ether extractable yield | 11.9% |
| Solid residue in liquor yield | 16.0% |
| Methanol, ethanol & acetone yield (%) | 5.3% |
| Total | 78.54% |
| Cooler inlet temp | 335 |
| Estimated mixing (Reactor inlet) temp | 355 |

Notes:
All mass balance data is referenced to the feedstock mass on a dry basis.

Gas Analysis (Wood Flour w/-Black Liquor 20140521)

TABLE 10

Non Condensable Gas Analysis from Radiata Wood Flour 20140521

| Methane | CO | Hydrogen | Ethylene | Ethane | Propylene | Propane | CO$_2$ | H$_2$S |
|---|---|---|---|---|---|---|---|---|
| 4.51 | 0.11% | 10.11% | 0.43% | 0.43% | 1.84% | 0.37% | 81.7% | 0.25% |

Bio-Crude Analysis of Wood Chip 20140521

TABLE 11

Analysis of Bio-Crude Oil (wood flour w/- black liquor 20140521)

| Description | | Pine BL 20140521 |
|---|---|---|
| Proximate Analysis | Moisture (% wt ar) | 8 |
| | Ash (% wt db) | 0.5 |
| | Volatiles (% wt db) | |
| | Fixed C. (% wt db) | |
| Ultimate Analysis | GCV (MJ/kg | 34.8 |
| | Carbon (% wt db) | 73.4 |
| | Hydrogen (% wt db) | 6.5 |
| | Nitrogen (% wt db) | 0.11 |
| | Sulphur (% wt db) | 0.56 |
| | Oxygen (% wt db) | |
| | Chlorine (%) | |
| | Molar H/C Ratio | |
| Ash Constituents (% oxide in ash) | SiO2 (% wt db) | 3.6 |
| | Al2O3 (% wt db) | 4.4 |
| | Fe2O3 (% wt db) | 5.6 |
| | TiO2 (% wt db) | 0.08 |
| | K2O (% wt db) | 1.4 |
| | MgO (% wt db) | 1.7 |
| | Na2O (% wt db) | 13.1 |
| | CaO (% wt db) | 3.2 |
| | SO3 (% wt db) | 19.1 |
| | P2O5 (% wt db) | 0.6 |
| | Mn3O4 (% wt db) | 0.24 |
| | SrO (% wt db) | <0.01 |
| | BaO (% wt db) | 0.04 |
| | ZnO (% wt db) | 0.2 |
| | CuO (% wt db) | 0.36 |
| | Cr2O3 (% wt db) | 0.16 |
| | Co3O4 (% wt db) | 0 |
| | NiO (% wt db) | 0.04 |
| | V2O5 (% wt db) | 0.52 |

The Bio-Crude Oil has a gross calorific value of 35 MJ/kg.

Solvent Extraction of Bio-Crude

Extraction of the oil from wood chip process water with the solvent diethyl ether gave 11.9% extractables as a fraction of the feedstock (dry basis). Total oils recoverable (bio-crude plus ether extractables were 34.9% of the feed mass.

*Radiata* Pine Wood Flour with Black Liquor 20140523

Operating Conditions (Wood Flour w/-Black Liquor 20140523)

Table 12 below shows the operating conditions of the mass balance run using wood flour w/-black liquor.

TABLE 12

Operating Conditions for Radiata Pine Wood Flour with Black Liquor 20140523

| | |
|---|---|
| Reactor Temperature | 355° C. |
| Reactor Pressure | 224 to 241 bar |
| Reactor Residence Time | 25 minutes |

Mass Balance (Wood Flour w/-Black Liquor 20140523)

This trial was performed using black liquor at a ratio of 7.75 kg of stock black liquor to 150 L of slurry. Slurry contained 8% *Radiata* pine wood flour db. Stock black liquor to wood ratio is 1:1.3 db.

TABLE 13

Mass Balance wood flour w/- black liquor 20140523

| | |
|---|---|
| Date | 20140523 |
| Feedstock | 8% Licella radiata pine |
| Liquid Catalyst | 1.3 kg stock black liquor per dry kg wood |
| T4 Injection time (mins) | 71 |
| Percent Solids in Feed | 10.49% |
| Percent solids in reactors | 4.2% |
| Solids in feed (kg) | 4.5 |
| product recovered (wet kg) | 1.118 |
| Moisture content of oil (%) | 18.5% |
| Bio crude recovered (dry kg) | 0.912 |
| Bio crude yield (dry) | 20.4% |
| NCG gas measured (m3/hr) | 0.43 |
| NCG density (kg/m3) | 1.55 |
| NCG (kg/hr) | 0.809 |
| Solids in feed (kg/hr) | 3.767 |
| NCG yield | 21.5% |
| Total feed to T4 - NCG (kg) | 104.4 |
| Ether extractable in liquor (%) | 0.56% |
| Ether extractable in liquor (kg) | 0.59 |
| Ether extractable yield | 13.2% |
| Solid residue in liquor (%) | 1.05% |
| Solid residue in liquor (kg) | 1.09 |
| Solid residue from catalyst (kg) | 0 |
| Solid residue in liquor yield | 24.5% |
| % black liquor solids in feed | 30.9% |
| % Inorganic material in feed | 14.5% |
| Organic material in feed (kg) | 3.81 |
| Methanol ethanol & acetone yield (kg) | 0.23 |
| Methanol, ethanol & acetone yield (%) | 5.13% |
| Yield Summary | |
| Bio crude yield (dry) | 20.4% |
| NCG yield | 21.5% |
| Ether extractable yield | 13% |
| Solid residue in liquor yield | 25% |
| Methanol, ethanol & acetone yield (%) | 5% |
| Total | 84.76% |
| Cooler inlet temp | 335 |
| Estimated mixing (Reactor inlet) temp | 355 |

Gas Analysis (Wood Flour w/-Black Liquor 20140523)

TABLE 14

Non Condensable Gas Analysis for Radiata Pine Wood Flour with Black Liquor 20140523

| Methane | CO | Hydrogen | Ethylene | Ethane | Propylene | Propane | $CO_2$ | $H_2S$ |
|---|---|---|---|---|---|---|---|---|
| 5.34% | 0.05% | 12.00% | 0.37% | 0.83% | 1.60% | 0.38% | 79.2% | 0.22% |

Bio-Crude Analysis (Wood Flour w/-Black Liquor 20140523)

TABLE 15

Analysis of Bio-Crude Oil

| | Description | Pine BL 20140523 |
|---|---|---|
| Proximate Analysis | Moisture (% wt ar) | 1.6 |
| | Ash (% wt db) | 0.4 |
| | Volatiles (% wt db) | |
| | Fixed C. (% wt db) | |
| Ultimate Analysis | GCV (MJ/kg) | 34.2 |
| | Carbon (% wt db) | 80.3 |
| | Hydrogen (% wt db) | 7.2 |
| | Nitrogen (% wt db) | 0.18 |
| | Sulphur (% wt db) | 0.68 |
| | Oxygen (% wt db) | 13.0 |
| | Chlorine (%) | |
| | Molar H/C Ratio | |
| Ash Constituents (% oxide in ash) | $SiO_2$ (% wt db) | 5.4 |
| | $Al_2O_3$ (% wt db) | 3.9 |
| | $Fe_2O_3$ (% wt db) | 2.5 |
| | $TiO_2$ (% wt db) | 0.07 |
| | $K_2O$ (% wt db) | 3.7 |
| | MgO (% wt db) | 2 |
| | $Na_2O$ (% wt db) | 27.9 |
| | CaO (% wt db) | 3.7 |
| | $SO_3$ (% wt db) | 38 |
| | $P_2O_5$ (% wt db) | 0.51 |
| | $Mn_3O_4$ (% wt db) | 0.32 |
| | SrO (% wt db) | <0.01 |
| | BaO (% wt db) | 0.04 |
| | ZnO (% wt db) | 0.16 |
| | CuO (% wt db) | 0.32 |
| | $Cr_2O_3$ (% wt db) | 0.07 |
| | $Co_3O_4$ (% wt db) | 0 |
| | NiO (% wt db) | 0.05 |
| | $V_2O_5$ (% wt db) | 0.09 |

The Cat-HTR processing temperatures (355° C. to 335° C.) were again within the normal Biomass processing temperatures The ash content of the Bio-Crude Oil was about 0.4%. The Bio-Crude Oil has a gross calorific value of 34.3 MJ/kg.

Solvent Extraction of Bio-Crude (Wood Flour w/-Black Liquor 20140523)

Extraction of the oil from wood chip process water with the solvent diethyl ether gave 13.2% extractables as a fraction of the feedstock (dry basis). Total oils recoverable (bio-crude plus ether extractables) were 33.6% of the feed mass.

Hog Fuel w/-Sodium Hydroxide 20140716

Operating Conditions (Hog Fuel w/-Sodium Hydroxide 20140716)

Table 16 below shows the operating conditions of the mass balance run on 16 Jul. 2014, on Hog Fuel and sodium hydroxide. This run produced the samples of Bio-Crude Oil, syngas and water, that are presented in the next section.

TABLE 16

Operating Conditions (Hog Fuel w/- Sodium Hydroxide 20140716)

| | |
|---|---|
| Reactor Temperature | 335 to 315° C. |
| Reactor Pressure | 227 bar |
| Reactor Residence Time | 25 minutes |

Mass Balance (Hog Fuel w/-Sodium Hydroxide 20140716)

This trial was performed using sodium hydroxide at a ratio of 11.2% by weight to feedstock db (target ratio was 12%, catalyst injection VSD was at 100% and pump stroke length was not adjustable during the run). Slurry contained 7.8% hog fuel db.

TABLE 17

Mass Balance (Hog Fuel w/- Sodium Hydroxide 20140716)

| | |
|---|---|
| Date | 20140716 |
| Feedstock | 7.8% hog fuel |
| Liquid Catalyst | 12% sodium hydroxide |
| T4 Injection time (mins) | 68 |
| Percent Solids in Feed | 7.8% |
| Percent solids in reactors | 2.9% |
| Solids in feed (kg) | 2.8 |
| product recovered (wet kg) | 0.763 |
| Moisture content of oil (%) | 14.7% |

TABLE 17-continued

Mass Balance (Hog Fuel w/- Sodium Hydroxide 20140716)

| | |
|---|---|
| Bio crude recovered (dry kg) | 0.651 |
| Bio crude yield (dry) | 23.3% |
| NCG gas measured (m3/hr) | 0.34 |
| NCG density (kg/m3) | 1.23 |
| NCG (kg/hr) | 0.515 |
| Solids in feed (kg/hr) | 2.434 |
| NCG yield | 21.2% |
| Total feed to T4 - NCG (kg) | 93.6 |
| Ether extractable in liquor (%) | 0.394% |
| Ether extractable in liquor (kg) | 0.37 |
| Ether extractable yield | 13.2% |
| Solid residue in liquor (%) | 1.40% |
| Solid residue in liquor (kg) | 1.31 |
| Solid residue from catalyst (kg) | 0.34 |
| Solid residue in liquor yield | 34.9% |
| % black liquor solids in feed | 0.0% |
| % Inorganic material in feed | 0.0% |
| Organic material in feed (kg) | 2.79 |
| Methanol ethanol & acetone yield (kg) | 16.8% |
| Methanol ethanol & acetone yield (%) | 6.00% |
| Yield Summary | |
| Bio crude yield (dry) | 23.3% |
| NCG yield | 21.2% |
| Ether extractable yield | 13.2% |
| Solid residue in liquor yield | 34.9% |
| Methanol, ethanol & acetone yield (%) | 6.0% |
| Total | 98.58% |
| Cooler inlet temp | 315 |
| Estimated mixing (Reactor inlet) temp | 335 |

Gas Analysis (Hog Fuel w/-Sodium Hydroxide 20140716)

TABLE 18

Non Condensable Gas Analysis (Hog Fuel w/- Sodium Hydroxide 20140716)

| Methane | CO | Hydrogen | Ethylene | Ethane | Propylene | Propane | $CO_2$ | $H_2S$ |
|---|---|---|---|---|---|---|---|---|
| 3.69% | 0.01% | 31.24% | 0.36% | 0.58% | 1.04% | 0.38% | 62.7% | 0.00% |

Bio-Crude Analysis (Hog Fuel w/-Sodium Hydroxide 20140716)
Data presented in Table 19 below is from the mass balance run.

TABLE 19

Analysis of Bio-Crude Oil (Hog Fuel w/- Sodium Hydroxide 20140716)

| Description | | Hog Fuel + Catalyst 20140716 |
|---|---|---|
| Proximate Analysis | Moisture (% wt ar) | |
| | Ash (% wt db) | 6.6 |
| | Volatiles (% wt db) | |
| | Fixed C. (% wt db) | |
| Ultimate Analysis | GCV (MJ/kg) | 33.9 |
| | Carbon (% wt db) | 76.7 |
| | Hydrogen (% wt db) | 7.2 |
| | Nitrogen (% wt db) | 0.3 |
| | Sulphur (% wt db) | 0.1 |

TABLE 19-continued

Analysis of Bio-Crude Oil (Hog Fuel w/- Sodium Hydroxide 20140716)

| Description | | Hog Fuel + Catalyst 20140716 |
|---|---|---|
| | Oxygen (% wt db) | 9.6 |
| | Chlorine (%) | |
| | Molar H/C Ratio | |
| Ash Constituents (% oxide in ash) | $SiO2$ (% wt db) | 0.8 |
| | $Al2O3$ (% wt db) | 1.7 |
| | $Fe2O3$ (% wt db) | 1.4 |
| | $TiO2$ (% wt db) | 0.05 |
| | $K2O$ (% wt db) | 0.34 |
| | MgO (% wt db) | 3.7 |
| | $Na2O$ (% wt db) | 7.2 |
| | CaO (% wt db) | 46.6 |
| | $SO3$ (% wt db) | 1.1 |
| | $P2O5$ (% wt db) | 2.46 |
| | $Mn3O4$ (% wt db) | 1.17 |

TABLE 19-continued

Analysis of Bio-Crude Oil (Hog Fuel w/- Sodium Hydroxide 20140716)

| Description | Hog Fuel + Catalyst 20140716 |
|---|---|
| SrO (% wt db) | 0.17 |
| BaO (% wt db) | 0.4 |
| ZnO (% wt db) | 0.31 |
| CuO (% wt db) | 0.11 |
| $Cr2O3$ (% wt db) | 0.02 |
| $Co3O4$ (% wt db) | |
| NiO (% wt db) | 0.02 |
| $V2O5$ (% wt db) | |

The Cat-HTR processing temperatures for the Hog Fuel Sodium Hydroxide were steady for the most part at 335° C. reactor inlet temperature (variable between 326° C. and 337° C.), pressure was steady for the most part at 271 bar, variable at its lowest to 230 bar.

The ash content of the Bio-Crude Oil was about 6.6%.

The Bio-Crude Oil has a gross calorific value of 36.3 MJ/kg, for comparison purposes diesel is around 45 MJ/kg.

Solvent Extraction of Bio-Crude (Hog Fuel w/-Sodium Hydroxide 20140716)

Extraction of the oil from Hog Fuel Cat-HTR water with the solvent diethyl ether gave 13.2% extractables as a fraction of the feedstock (dry basis). Total oils recoverable (bio-crude plus ether extractables) were 36.5% of the feed mass.

Hog Fuel w/-Black Liquor (20140724)

Operating Conditions (Hog Fuel w/-Black Liquor 20140724)

Table 20 below shows the operating conditions of a mass balance run using Hog Fuel Black Liquor.

TABLE 20

| Operating Conditions (Hog Fuel w/-Black Liquor 20140724) | |
| --- | --- |
| Reactor Temperature | 335 to 315° C. |
| Reactor Pressure | 226 to 244 bar |
| Reactor Residence Time | 25 minutes |

Mass Balance (Hog Fuel w/-Black Liquor 20140724)

This trial was performed using black liquor at a ratio of 9.7 kg of stock black liquor to 7.44 kg of hog fuel db. Slurry contained 8.6% Hog Fuel db. Stock black liquor to Hog fuel ratio is 1:1.3 db.

TABLE 21

| Mass Balance (Hog Fuel w/-Black Liquor 20140724) | |
| --- | --- |
| Date | 20140724 |
| Feedstock | 8% hog fuel |
| Liquid Catalyst | 1.3 kg stock black liquor per dry kg wood |
| T4 injection time (mins) | 92 |
| Percent Solids in Feed | 10.5% |
| Percent solids in reactors | 4.3% |
| Solids in feed (kg) | 6.2 |
| product recovered (wet kg) | 1.258 |
| Moisture content of oil (%) | 16.7% |
| Bio crude recovered (dry kg) | 1.048 |
| Bio crude yield (dry) | 17.0% |
| NCG gas measured (m3/hr) | 0.43 |
| NCG density (kg/m3) | 1.60 |
| NCG (kg/hr) | 0.835 |
| Solids in feed (kg/hr) | 4.018 |
| NCG yield | 20.8% |
| Total feed to T4-NCG (kg) | 141.5 |
| Ether extractable in liquor (%) | 0.402% |
| Ether extractable in liquor (kg) | 0.57 |
| Ether extractable yield | 9.2% |

TABLE 21-continued

| Mass Balance (Hog Fuel w/-Black Liquor 20140724) | |
| --- | --- |
| Solid residue in liquor (%) | 0.81% |
| Solid residue in liquor (kg) | 1.15 |
| Solid residue from catalyst (kg) | 0.00 |
| Solid residue in liquor yield | 18.7% |
| % black liquor solids in feed | 31.0% |
| % inorganic material in feed | 14.6% |
| Organic material in feed (kg) | 526.2% |
| Methanol ethanol & acetone yield (kg) | 31.6% |
| Methanol, ethanol & acetone yield (%) | 5.13% |
| Yield Summary | |
| Bio crude yield (dry) | 17.0% |
| NCG yield | 20.8% |
| Ether extractable yield | 9.2% |
| Solid residue in liquor yield | 18.7% |
| Methanol, ethanol & acetone yield (%) | 5.1% |
| Total | 70.87% |
| Cooler inlet temp | 315 |
| Estimated mixing (Reactor inlet) temp | 335 |

Gas Analysis (Hog Fuel w/-Black Liquor 20140724)

TABLE 22

| Non Condensable Gas Analysis (Hog Fuel w/-Black Liquor 20140724) | | | | | | | | |
| --- | --- | --- | --- | --- | --- | --- | --- | --- |
| Methane | CO | Hydrogen | Ethylene | Ethane | Propylene | Propane | $CO_2$ | $H_2S$ |
| 5.00% | 0.05% | 9.56% | 0.29% | 0.71% | 1.59% | 0.38% | 82.2% | 0.18% |

Bio-Crude Analysis (Hog Fuel w/-Black Liquor 20140724)

Data presented in the Table 23 below is from the mass balance run.

TABLE 23

| Analysis of Bio-Crude Oil (Hog Fuel w/-Black Liquor 20140724) | | |
| --- | --- | --- |
| Description | | Hog Fuel + BL 20140724 |
| Proximate Analysis | Moisture (% wt ar) | 6 |
| | Ash (% wt db) | 2.8 |
| | Volatiles (% wt db) | |
| | Fixed C. (% wt db) | |
| Ultimate Analysis | GCV (MJ/kg | 32.6 |
| | Carbon (% wt db) | 75.1 |
| | Hydrogen (% wt db) | 6.6 |
| | Nitrogen (% wt db) | 0.3 |
| | Sulphur (% wt db) | 1.1 |

TABLE 23-continued

Analysis of Bio-Crude Oil (Hog Fuel w/-Black Liquor 20140724)

| Description | | Hog Fuel + BL 20140724 |
|---|---|---|
| | Oxygen (% wt db) | 12.7 |
| | Chlorine (%) | |
| | Molar H/C Ratio | |
| Ash Constituents (% oxide in ash) | SiO2 (% wt db) | 3 |
| | Al2O3 (% wt db) | 3.7 |
| | Fe2O3 (% wt db) | 9.9 |
| | TiO2 (% wt db) | 0.13 |
| | K2O (% wt db) | 0.44 |
| | MgO (% wt db) | 3.7 |
| | Na2O (% wt db) | 3.6 |
| | CaO (% wt db) | 36.2 |
| | SO3 (% wt db) | 24.3 |
| | P2O5 (% wt db) | 3.55 |
| | Mn3O4 (% wt db) | 1.39 |
| | SrO (% wt db) | 0.17 |
| | BaO (% wt db) | 0.5 |
| | ZnO (% wt db) | 0.56 |
| | CuO (% wt db) | 0.17 |
| | Cr2O3 (% wt db) | 0.02 |
| | Co3O4 (% wt db) | <0.1 |
| | NiO (% wt db) | 0.02 |
| | V2O5 (% wt db) | 0 |

The processing temperatures for the Hog Fuel w/-black liquor was essentially steady around 330° C. reactor inlet temperature. Pressure was variable between 226 and 244 bar.

The ash content of the Bio-Crude Oil was about 2.8%. The Bio-Crude Oil has a gross calorific value of 32.6 MJ/kg, for comparison purposes diesel is around 45 MJ/kg.

Solvent Extraction of Bio-Crude (Hog Fuel w/-Black Liquor 20140724)

Extraction of the oil from Hog Fuel w/-black liquor process water with the solvent diethyl ether gave 9.2% extractables as a fraction of the feedstock (dry basis). Taking the oil yield as 26.3%.

Mixed Kraft Feedstock Moderate Temperature 20140731

Operating Conditions (Mixed Kraft Feedstocks 20140731)

Table 24 below shows the operating conditions of the mass balance run using Mixed Kraft Feedstock. This trial was at moderate temperature of 321° C.

TABLE 24

Operating Conditions (Mixed Kraft Feedstocks 20140731)

| | |
|---|---|
| Reactor Temperature | 335 to 315° C. |
| Reactor Pressure | 250 bar |
| Reactor Residence Time | 25 minutes |

Mass Balance of Mixed Feedstocks Cat-HTR 20140724 The Mixed Kraft Feedstock mixture is composed from solids:

TABLE 25

Mass Balance (Mixed Kraft Feedstocks 20140731)
The mixed kraft feedstock is composed from solids:

| | kg to feed tank | % of dry feed |
|---|---|---|
| Hog Fuel | 8.0 | 55.3% |
| Pine | 1.8 | 12.4% |
| Sludge | 0.2 | 1.4% |
| Black liquor solids | 4.5 | 30.9% |
| Black liquor water | 8.5 | |
| Water | 123.5 | |
| Slurry tank contents | | |
| Total solids | 14.5 | |
| Total water | 132.0 | |
| Total to feed tank | 146.5 | |
| % Solids | 9.88% | |

This trial was performed using black liquor at a ratio of 13 kg of stock black liquor to 10 k g of mixed woody feedstocks db. Slurry contained mixed feedstocks to water at 8.1% db. Stock black liquor to mixed dry feedstocks ratio is 1.3:1 db.

TABLE 26

Mass Balance (Mixed Kraft Feedstocks 20140731)

| | |
|---|---|
| Date | 20140731 |
| Feedstock | 6.4% hog fuel, 1.44% wood, 0.16% sludge |
| Liquid Catalyst | 1.3 kg stock black liquor per dry kg mix |
| T4 injection time (mins) | 83 |
| Percent Solids in Feed | 9.9% |
| Percent solids in reactors | 4.0% |
| Solids in feed (kg) | 5.0 |
| product recovered (wet kg) | 1.134 |
| Moisture content of oil (%) | 12.9% |
| Bio crude recovered (dry kg) | 0.988 |
| Bio crude yield (dry) | 19.6% |
| NCG gas measured (m3/hr) | 0.47 |
| NCG density (kg/m3) | 1.60 |
| NCG (kg/hr) | 0.914 |
| Solids in feed (kg/hr) | 3.635 |
| NCG yield | 25.1% |
| Total feed to T4-NCG (kg) | 124.4 |
| Ether extractable in liquor (%) | 1.440% |
| Ether extractable in liquor (kg) | 1.79 |
| Ether extractable yield | 35.6% |
| Solid residue in liquor (%) | 0.88% |
| Solid residue in liquor (kg) | 1.10 |
| Solid residue from catalyst (kg) | 0.00 |
| Solid residue in liquor yield | 21.8% |
| % black liquor solids in feed | 30.9% |
| % inorganic material in feed | 15.9% |
| Organic material in feed (kg) | 422.8% |
| Methanol ethanol & acetone yield (kg) | 25.4% |
| Methanol, ethanol & acetone yield (%) | 5.04% |

TABLE 26-continued

Mass Balance (Mixed Kraft Feedstocks 20140731)

| Yield Summary | |
|---|---|
| Bio crude yield (dry) | 19.0% |
| NCG yield | 25.1% |
| Ether extractable yield | 35.6% |
| Solid residue in liquor yield | 21.8% |
| Methanol, ethanol & acetone yeild (%) | 5.0% |
| Total | 107.24% |
| Cooler inlet temp | 310 |
| Estimated mixing (Reactor inlet) temp | 330 |

Gas Analysis (Mixed Kraft Feedstocks 20140731)

TABLE 27

Non Condensable Gas Analysis (Mixed Kraft Feedstocks 20140731)

| Methane | CO | Hydrogen | Ethylene | Ethane | Propylene | Propane | $CO_2$ | $H_2S$ |
|---|---|---|---|---|---|---|---|---|
| 4.79% | 0.04% | 9.74% | 0.28% | 0.77% | 1.46% | 0.41% | 82.3% | 0.17% |

Bio-Crude Analysis (Mixed Kraft Feedstocks 20140731)

Data presented in Table 28 below is from the mass balance run.

TABLE 28

Analysis of Bio-Crude Oil (Mixed Kraft Feedstocks 20140731)

| Description | | Mixed Feed + BL 20140731 |
|---|---|---|
| Proximate Analysis | Moisture (% wt ar) | 7.5 |
| | Ash (% wt db) | 2.6 |
| | Volatiles (% wt db) | 0.0 |
| | Fixed C. (% wt db) | 0.0 |
| Ultimate Analysis | GCV (MJ/kg) | 33.0 |
| | Carbon (% wt db) | 79.2 |
| | Hydrogen (% wt db) | 6.36 |
| | Nitrogen (% wt db) | 0.38 |
| | Sulphur (% wt db) | 0.58 |
| | Oxygen (% wt db) | 10.18 |
| | Chlorine (%) | |
| | Molar H/C Ratio | |
| Ash Constituents (% oxide in ash) | SiO2 (% wt db) | 3.3 |
| | Al2O3 (% wt db) | 4.9 |
| | Fe2O3 (% wt db) | 6.6 |
| | TiO2 (% wt db) | 0.15 |
| | K2O (% wt db) | 0.72 |
| | MgO (% wt db) | 4.8 |
| | Na2O (% wt db) | 5.5 |
| | CaO (% wt db) | 42.1 |
| | SO3 (% wt db) | 20.6 |
| | P2O5 (% wt db) | 3.5 |
| | Mn3O4 (% wt db) | 0.3 |
| | SrO (% wt db) | 0.6 |
| | BaO (% wt db) | <0.1 |
| | ZnO (% wt db) | <0.1 |
| | CuO (% wt db) | 0.2 |
| | Cr2O3 (% wt db) | 1.7 |
| | Co3O4 (% wt db) | <0.1 |
| | NiO (% wt db) | <0.1 |
| | V2O5 (% wt db) | 0.5 |

The processing temperatures for the Mixed Kraft Feedstocks were held steady within (331-336° C.) were again steady and stabilised at 331° C. The ash content of the Bio-Crude Oil was about 2.6%, The Bio-Crude Oil has a gross calorific value of 33 MJ/kg, for comparison purposes diesel is around 45 MJ/kg.

Solvent Extraction of Bio-Crude (Mixed Kraft Feedstocks 20140731)

Extraction of the oil from Mixed Feedstocks process water with the solvent diethyl ether gave 35.6% extractables as a fraction of the feedstock (dry basis). Total oils recoverable (biocrude plus ether extractables) were 54.2% of the feed mass.

Mixed Kraft Feedstocks High Temperature 201407814

Operating Conditions (Mixed Kraft Feedstocks 20140814)

Table 29 below shows the operating conditions of the mass balance run on Mixed Kraft Feedstocks.

TABLE 29

Operating Conditions (Mixed Kraft Feedstocks 20140814)

| Reactor Temperature | 355 to 335° C. |
|---|---|
| Reactor Pressure | 238 to 250 bar |
| Reactor Residence Time | 25 minutes |

Mass Balance (Mixed Kraft Feedstocks 20140814)

The Mixed Kraft Feedstock mixture is composed from solids:

TABLE 30

Content (Mixed Kraft Feedstocks 20140814)

|  | kg to feed tank | % of dry feed |
|---|---|---|
| Hog Fuel | 8.0 | 55.3% |
| Pine | 1.8 | 12.4% |
| Sludge | 0.2 | 1.4% |
| Black liquor solids | 4.5 | 30.9% |
| Black liquor water | 8.5 | |
| Water | 127 | |
| Total solids | 14.5 | |
| Total water | 135.5 | |
| Total to feed tank | 150.0 | |
| % Solids | 9.65% | |

TABLE 31

Mass Balance (Mixed Kraft Feedstocks 20140814)

| Date | 20140814 |
|---|---|
| Feedstock | 6.4% hog fuel, 1.44% wood, 0.16% sludge |
| Liquid Catalyst | 1.3 kg stock black liquor per dry kg mix |
| T4 injection time (mins) | 61 |
| Percent Solids in Feed | 9.7% |
| Percent solids in reactors | 3.5% |
| Solids in feed (kg) | 3.0 |
| product recovered (wet kg) | 0.521 |
| Moisture content of oil (%) | 20.1% |
| Bio crude recovered (dry kg) | 0.416 |
| Bio crude yield (dry) | 13.7% |
| NCG gas measured (m3/hr) | 0.42 |
| NCG density (kg/m3) | 1.52 |
| NCG (kg/hr) | 0.784 |
| Solids in feed (kg/hr) | 2.990 |
| NCG yield | 26.2% |
| Total feed to T4-NCG (kg) | 85.5 |
| Ether extractable in liquor (%) | 0.574% |
| Ether extractable in liquor (kg) | 0.49 |
| Ether extractable yield | 16.1% |
| Solid residue in liquor (%) | 0.66% |
| Solid residue in liquor (kg) | 0.56 |
| Solid residue from catalyst (kg) | 0.00 |
| Solid residue in liquor yield | 18.4% |
| % black liquor solids in feed | 30.9% |
| % inorganic material in feed | 15.9% |
| Organic material in feed (kg) | 422.8% |
| Methanol ethanol & acetone yield (kg) | 25.4% |
| Methanol, ethanol & acetone yield (%) | 5.04% |

TABLE 31-continued

Mass Balance (Mixed Kraft Feedstocks 20140814)

| Yield Summary | |
|---|---|
| Bio crude yield (dry) | 13.7% |
| NCG yield | 26.2% |
| Ether extractable yield | 16.1% |
| Solid residue in liquor yield | 18.4% |
| Methanol, ethanol & acetone yeild (%) | 5.0% |
| Total | 79.54% |
| Cooler inlet temp | 335 |
| Estimated mixing (Reactor inlet) temp | 355 |

The mass balance across the Cat-HTR reactor for the Mixed Kraft Feedstocks trial has significant mass missing. This behaviour might be explained by material retained within the internal pipes on the reactor and cooler.

Gas Analysis (Mixed Kraft Feedstocks 20140814)

TABLE 32

Non Condensable Gas Analysis (Mixed Kraft Feedstocks 20140814)

| Methane | CO | Hydrogen | Ethylene | Ethane | Propylene | Propane | $CO_2$ | $H_2S$ |
|---|---|---|---|---|---|---|---|---|
| 5.12% | 0.04% | 13.75% | 0.36% | 0.86% | 1.36% | 0.38% | 77.9% | 0.26% |

Bio-Crude Analysis (Mixed Kraft Feedstocks 20140814)

Data presented in Table 33 below is from a mass balance run.

TABLE 33

Analysis of Bio-Crude Oil (Mixed Kraft Feedstocks 20140814)

| Description | | Mixed Feed + BL 20140814 |
|---|---|---|
| Proximate Analysis | Moisture (% wt ar) | 4 |
| | Ash (% wt db) | 2.04 |
| | Volatiles (% wt db) | |
| | Fixed C. (% wt db) | |
| Ultimate Analysis | GCV (MJ/kg) | 33.0 |
| | Carbon (% wt db) | 77.6 |
| | Hydrogen (% wt db) | 6.85 |
| | Nitrogen (% wt db) | 0.32 |
| | Sulphur (% wt db) | 0.57 |
| | Oxygen (% wt db) | 12.4 |
| | Chlorine (%) | |
| | Molar H/C Ratio | |

TABLE 33-continued

Analysis of Bio-Crude Oil (Mixed Kraft Feedstocks 20140814)

| Description | | Mixed Feed + BL 20140814 |
|---|---|---|
| Ash Constituents (% oxide in ash) | SiO2 (% wt db) | 3.3 |
| | Al2O3 (% wt db) | 5 |
| | Fe2O3 (% wt db) | 5.1 |
| | TiO2 (% wt db) | 0.21 |
| | K2O (% wt db) | 0.81 |
| | MgO (% wt db) | 4.8 |
| | Na2O (% wt db) | 6.7 |
| | CaO (% wt db) | 42.4 |
| | SO3 (% wt db) | 19.9 |
| | P2O5 (% wt db) | 3.5 |
| | Mn3O4 (% wt db) | 0.3 |
| | SrO (% wt db) | 0.5 |
| | BaO (% wt db) | 0.1 |
| | ZnO (% wt db) | <0.1 |
| | CuO (% wt db) | 0.2 |
| | Cr2O3 (% wt db) | 2.3 |
| | Co3O4 (% wt db) | <0.1 |
| | NiO (% wt db) | <0.1 |
| | V2O5 (% wt db) | 0.6 |

The ash content of the Bio-Crude Oil was about 2%.
The Bio-Crude Oil has a gross calorific value of 33.7 MJ/kg dry basis Solvent Extraction of Bio-Crude (Mixed Kraft Feedstocks 20140814)

Extraction of the oil from Mixed Feedstocks process water with the solvent diethyl ether gave 16.1% extractables as a fraction of the feedstock (dry basis). Taking the oil yield (bio-crude plus ether extractables) as 29.8%

Discussion

Bio-Crude Quality

Bio-crude quality is most readily assessed in the first instance by means of its Gross Calorific Value (GCV). This is the gross energy contained in the material and is closely related to the oxygen and hydrogen content of the bio-crude. For *Radiata* pine wood flour with sodium hydroxide catalyst on the SPP, typical GCV of bio-crude is in the range 34-36 MJ/kg dry basis.

The *Radiata* pine wood flour bio-crude has a low ash content, and therefore dry basis values are similar to dry ash free basis (daf) values. The bio-crudes from hog fuel and black liquor feedstocks have significantly higher ash values, and it is more appropriate to compare these on a daf basis.

In Figure One the GCV on a daf basis is plotted against oxygen content for Bio-crudes prepared in this project and for a historical series of Licella bio-crudes (dry basis) from *Radiata* Pine. The oxygen content is determined by difference from the ultimate analysis as [100−% C−% H−% S−% N]. As such it is subject to accumulation of systematic and random errors and consequently the error associated with these values is estimated as +/−1-2 percentage points.

The calorific values of the bio-crudes from this study lie in the range within, or very close to, the target band of 334-36 MJ/kg. Upon distillation, the bio-crude distillates can be expected to have an oxygen content close to 11%. The significance of the target is that commercial hydrotreating technologies exist for hydrodeoxygenation (HDO) of oils at around 11% oxygen. Licella's assessment is that the remaining oxygen in the bio-crudes is more efficiently removed by hydrotreating in conventional refinery processes than by other processes. These values demonstrate that the catalytic components in black liquor can effectively substitute for the basic catalyst sodium hydroxide in Cat-HTR applications. The other main heteroatoms present in the bio-crudes are Nitrogen and Sulphur. Both of these elements are higher in the bio-crudes derived from hog-fuel and black liquor than those derived from *Radiata* pine wood flour. Sulphur is unlikely to present an issue for further upgrading as oil refining processes are designed to accomplish desulphurization. The distribution and nature of the nitrogen content in the bio-crudes will need to be examined post-distillation to assess possible impact on downstream processing. Denitrification steps are well established in oil refining processes.

Aromatic Content

Licella bio-crudes from *Radiata* pine wood flour have about 50% of their carbon atoms in an aromatic environment by 13C NMR spectroscopy. While this does not mean that hydrodeoxygenated bio-crudes will contain 50% aromatics, it is indicative of a high potential to produce aromatic chemicals, for example by catalytic reforming. Bio-crudes based on high proportions of black liquor may be expected to have still higher aromatic contents, however this should be confirmed by testing.

This scenario is commercially interesting because of the increasing influence of shale oils in the US which are relatively low in fractions used to make aromatic chemicals.

Bio-crude Yields Bio-crude yields are generally consistent with other feedstocks processed using the SPP, as discussed in Section 9.0. The SPP uses a relatively large amount of supercritical steam to heat the biomass slurry to reaction temperature, and the consequent dilution favours dissolution of bio-crude into the water phase. This is a phenomenon that has been reported by other investigators, for example.

Waste Water Sample Analysis

TABLE 34

Mixed kraft feedstocks trial (20140814) water sample analysis

| Our Reference | | 114714-1 |
|---|---|---|
| Your Reference | | 1 |
| Type of sample | UNITS | Water |
| VOCs in water | | |
| Date extracted | | 19 Aug. 2014 |
| Date analysed | | 22 Aug. 2014 |
| Dichlorodifluoromethane | µg/L | <1000 |
| Chloromethane | µg/L | <1000 |
| Vinyl Chloride | µg/L | <1000 |
| Bromomethane | µg/L | <1000 |
| Chloroethane | µg/L | <1000 |
| Trichlorofluoromethane | µg/L | <1000 |
| 1,1-Dichloroethane | µg/L | <100 |
| Trans-1,2-dichloroethene | µg/L | <100 |
| Bromochloromethane | µg/L | <100 |
| Chloroform | µg/L | <100 |

TABLE 34-continued

Mixed kraft feedstocks trial (20140814) water sample analysis

| Our Reference | | 114714-1 |
|---|---|---|
| Your Reference | | 1 |
| Type of sample | UNITS | Water |

| | | |
|---|---|---|
| 2,2-dichloropropane | µg/L | <100 |
| 1,2-dichloroethane | µg/L | <100 |
| 1,1,1-trichloroethane | µg/L | <100 |
| 1,1-dichloropropene | µg/L | <100 |
| Cyclohexande | µg/L | <100 |
| Carbon tetrachloride | µg/L | <100 |
| Benzene | µg/L | 180 |
| Dibromomethane | µg/L | <100 |
| 1,2-dichloropropane | µg/L | <100 |
| Trichloroethene | µg/L | <100 |
| Bromodichloromethane | µg/L | <100 |
| trans-1,3-dichloropropene | µg/L | <100 |
| cis-1,3-dichloropropene | µg/L | <100 |
| 1,1,2-trichloroethane | µg/L | <100 |
| Toluene | µg/L | 370 |
| 1,3-dichloropropane | µg/L | <100 |
| Dibromochloromethane | µg/L | <100 |
| 1,2-dibromoethane | µg/L | <100 |
| Tetrachloroethene | µg/L | <100 |
| 1,1,1,2-tetrachloroethane | µg/L | <100 |
| Chlorobenzene | µg/L | <100 |
| Ethylbenzene | µg/L | <100 |
| Bromoform | µg/L | <100 |
| m + p-xylene | µg/L | <200 |
| Styrene | µg/L | <100 |
| 1,1,2,2-tetrachlororethane | µg/L | <100 |
| o-xylene | µg/L | <100 |
| 1,2,3-trichloropropane | µg/L | <100 |
| Isopropylbenzene | µg/L | <100 |
| Bromobenzene | µg/L | <100 |
| n-propyl benzene | µg/L | <100 |
| 2-chlorotoluene | µg/L | <100 |
| 4-chlorotoluene | µg/L | <100 |
| 1,3,5-trimethylbenzene | µg/L | <100 |
| Tert-butyl benzene | µg/L | <100 |
| 1,2,4-trimethyl benzene | µg/L | <100 |
| 1,3-dichlorobenzene | µg/L | <100 |
| Sec-butyl benzene | µg/L | <100 |
| 1,4-dichlorobenzene | µg/L | <100 |
| 4-isopropyl toluene | µg/L | <100 |
| 1,2-dichlorobenzene | µg/L | <100 |
| n-butyl benzene | µg/L | <100 |
| 1,2-dibromo-3-chloropropane | µg/L | <100 |
| 1,2,4-trichlorobenzene | µg/L | <100 |
| Hexachlorobutadiene | µg/L | <100 |
| 1,2,3-trichlorobenzene | µg/L | <100 |
| Surrogate Dibromofluoromethane | % | 100 |
| Surrogate toluene-d8 | % | 101 |
| Surrogate 4-BFB | % | 105 |
| vTRH(C6-C10)/BTEXN in Water | | |
| Date extracted | | 19 Aug. 2014 |
| Date analysed | | 22 Aug. 2014 |
| $TRHC_6-C_9$ | µg/L | 31,000 |
| $TRHC_6-C_{10}$ | µg/L | 34,000 |
| $TRHC_6-C_{10}$ less BTEX (F1) | µg/L | 33,000 |
| Benzene | µg/L | 180 |
| Toluene | µg/L | 370 |
| Ethylbenzene | µg/L | <100 |
| m+p-xylene | µg/L | <200 |
| o-xylene | µg/L | <100 |
| Naphtalene | µg/L | <100 |
| Surrogate Dibromofluoromethane | % | 100 |
| Surrogate toluene-d8 | % | 101 |
| Surrogate 4-BFB | % | 105 |
| svTRH(C6-C40) in Water | | |
| Date extracted | | 18 Aug. 2014 |
| Date analysed | | 19 Aug. 2014 |
| $TRHC_{10}-C_{14}$ | µg/L | 650,000 |
| $TRHC_{15}-C_{28}$ | µg/L | 490,000 |
| $TRHC_{29}-C_{36}$ | µg/L | 14,000 |
| $TRH > C_{10}-C_{15}$ | µg/L | 800,000 |
| $TRH > C_{10}-C_{15}$ less Naphtalene (F2) | µg/L | 800,000 |
| $TRH > C_{15}-C_{34}$ | µg/L | 180,000 |
| $TRH > C_{34}-C_{40}$ | µg/L | 1,800 |
| Surrogate a-Terphenyl | % | |
| HM in water - total | | |
| Date prepared | | 18 Aug. 2014 |
| Date analysed | | 18 Aug. 2014 |
| Arsenic - total | µg/L | 45 |
| Cadmium - total | µg/L | <0.1 |
| Chromium - total | µg/L | 1 |
| Copper - total | µg/L | <1 |
| Lead - total | µg/L | <1 |
| Mercury - total | µg/L | 0.3 |
| Nickel - total | µg/L | <1 |
| Zinc - total | µg/L | 44 |
| Metals in water - Acid extractable | | |
| Date prepared | | 18 Aug. 2014 |
| Date analysed | | 18 Aug. 2014 |
| Sulfur - total | mg/L | 840 |
| Miscallaneous Inorganics | | |
| Date prepared | | 15 Aug. 2014 |
| Date analysed | | 15 Aug. 2014 |
| pH | pH Units | 7 |
| Total Dissolved Solids (grav) | mg/L | 15,000 |
| BOD | mg/L | 600 |
| COD | mg $O_2$/L | 19,000 |
| Total Organic Carbon | mg/L | 5,900 |
| Cations in Water - total | | |
| Date prepared | | 18 Aug. 2014 |
| Date analysed | | 18 Aug. 2014 |
| Sodium- total | mg/L | 2,300 |
| Potassium - total | mg/L | 190 |
| Calcium - total | mg/L | 16 |
| Magnesium - total | mg/L | 3.4 |

| Method ID | Methodology Summary |
|---|---|
| Org-013 | Water samples are analysed directly by purge and trap GC-MS. |
| Org-016 | Soil samples are extracted with methanol and spiked into water prior to analysing by purge and trap GC-MS. Water samples are analysed directly by purge and trap GC-MS. F1 = (C6-C10)-BTEX as per NEPM B1 Guideline on Investigation of Levels for Soil and Groundwater. |
| Org-003 | Soil samples are extracted with Dichloromethane-Acetone and waters with dichloromethane and analysed by GC-FID. F2 = (>C10-C16)-Naphtalene as per NEPM B1 Guideline on Investigation of Levels for Soil and Groundwater (HSLs Tables 1A (3,4)). Note Naphtalene is determined from the VOC analysis. |
| Metals-022ICP-MS | Determination of various metals by ICP-MS. |
| Metals-021 CV-AAS | Determination of Mercury by Cold Vapour AAS. |
| Metals-020ICP-AES | Determination of various metals by ICP-AES. |

TABLE 34-continued

Mixed kraft feedstocks trial (20140814) water sample analysis

| | | |
|---|---|---|
| Our Reference | | 114714-1 |
| Your Reference | | 1 |
| Type of sample | UNITS | Water |

| | |
|---|---|
| Inorg-001 | pH - Measured using pH meter and electrode in accordance with APHA 22nd ED, 4500-H+. Please note that the results for water analyses are indicative only, as analysis outside of the APHA storage times. |
| Inorg-018 | Total Dissolved Solids - Determined gravimetrically. The solids are dried at 180 +/− 5° C. |
| Inorg-091 | BOD - Analysed in accordance with APHA 22nd ED 5210D and in house INORG-091. |
| Inorg-087 | Samples are digested in acid with a known excess of potassium dichromate then titrated agains ammonium ferrous sulphate in accordance with APHA 22nd ED 5310B |
| Inorg-079 | TOC determined using a TOC analyser using the combustion method. DOC is filtered prior to determiantion. Analysis using APHA 22nd ED 5310B. |

| | Units | PQL | Method | Blank | Duplicate Sm# | Duplicate results | Spike Sm# | Spike % Recovery |
|---|---|---|---|---|---|---|---|---|
| Quality Control VOCs in Water | | | | | | | | |
| Date Extracted | | | | 19 Aug. 2014 | (NT) | (NT) | LCS-W1 | 19 Aug. 2014 |
| Date Analysed | | | | 22 Aug. 2014 | (NT) | (NT) | LCS-W1 | 22 Aug. 2014 |
| Dichlorodifluoromethane | µg/L | 10 | Org-013 | <10 | (NT) | (NT) | (NR) | (NR) |
| Chloromethane | µg/L | 10 | Org-013 | <10 | (NT) | (NT) | (NR) | (NR) |
| Vinyl Chloride | µg/L | 10 | Org-013 | <10 | (NT) | (NT) | (NR) | (NR) |
| Bromomethane | µg/L | 10 | Org-013 | <10 | (NT) | (NT) | (NR) | (NR) |
| Chloroethane | µg/L | 10 | Org-013 | <10 | (NT) | (NT) | (NR) | (NR) |
| Trichlorofluoromethane | µg/L | 10 | Org-013 | <10 | (NT) | (NT) | (NR) | (NR) |
| 1,1-Dichloroethane | µg/L | 1 | Org-013 | <1 | (NT) | (NT) | LCS-W1 | 99% |
| Trans-1,2-dichloroethene | µg/L | 1 | Org-013 | <1 | (NT) | (NT) | (NR) | (NR) |
| Bromochloromethane | µg/L | 1 | Org-013 | <1 | (NT) | (NT) | (NR) | (NR) |
| Chloroform | µg/L | 1 | Org-013 | <1 | (NT) | (NT) | LCS-W1 | 96% |
| 2,2-dichloropropane | µg/L | 1 | Org-013 | <1 | (NT) | (NT) | (NR) | (NR) |
| 1,2-dichloroethane | µg/L | 1 | Org-013 | <1 | (NT) | (NT) | LCS-W1 | 94% |
| 1,1,1-trichloroethane | µg/L | 1 | Org-013 | <1 | (NT) | (NT) | LCS-W1 | 96% |
| 1,1-dichloropropene | µg/L | 1 | Org-013 | <1 | (NT) | (NT) | (NR) | (NR) |
| Cyclohexande | µg/L | 1 | Org-013 | <1 | (NT) | (NT) | (NR) | (NR) |
| Carbon tetrachloride | µg/L | 1 | Org-013 | <1 | (NT) | (NT) | (NR) | (NR) |
| Benzene | µg/L | 1 | Org-013 | <1 | (NT) | (NT) | (NR) | (NR) |
| Dibromomethane | µg/L | 1 | Org-013 | <1 | (NT) | (NT) | (NR) | (NR) |
| 1,2-dichloropropane | µg/L | 1 | Org-013 | <1 | (NT) | (NT) | (NR) | (NR) |
| Trichloroethene | µg/L | 1 | Org-013 | <1 | (NT) | (NT) | LCS-W1 | 92% |
| Bromodichloromethane | µg/L | 1 | Org-013 | <1 | (NT) | (NT) | LCS-W1 | 96% |
| trans-1,3-dichloropropene | µg/L | 1 | Org-013 | <1 | (NT) | (NT) | (NR) | (NR) |
| cis-1,3-dichloropropene | µg/L | 1 | Org-013 | <1 | (NT) | (NT) | (NR) | (NR) |
| 1,1,2-trichloroethane | µg/L | 1 | Org-013 | <1 | (NT) | (NT) | (NR) | (NR) |
| Toluene | µg/L | 1 | Org-013 | <1 | (NT) | (NT) | (NR) | (NR) |
| 1,3-dichloropropane | µg/L | 1 | Org-013 | <1 | (NT) | (NT) | (NR) | (NR) |
| Dibromochloromethane | µg/L | 1 | Org-013 | <1 | (NT) | (NT) | LCS-W1 | 96% |
| 1,2-dibromoethane | µg/L | 1 | Org-013 | <1 | (NT) | (NT) | (NR) | (NR) |
| Tetrachloroethene | µg/L | 1 | Org-013 | <1 | (NT) | (NT) | LCS-W1 | 101% |
| 1,1,1,2-tetrachloroethane | µg/L | 1 | Org-013 | <1 | (NT) | (NT) | (NR) | (NR) |
| Chlorobenzene | µg/L | 1 | Org-013 | <1 | (NT) | (NT) | (NR) | (NR) |
| Ethylbenzene | µg/L | 1 | Org-013 | <1 | (NT) | (NT) | (NR) | (NR) |
| Bromoform | µg/L | 1 | Org-013 | <1 | (NT) | (NT) | (NR) | (NR) |
| m + p-xylene | µg/L | 2 | Org-013 | <2 | (NT) | (NT) | (NR) | (NR) |
| Styrene | µg/L | 1 | Org-013 | <1 | (NT) | (NT) | (NR) | (NR) |
| 1,1,2,2-tetrachlororethane | µg/L | 1 | Org-013 | <1 | (NT) | (NT) | (NR) | (NR) |
| o-xylene | µg/L | 1 | Org-013 | <1 | (NT) | (NT) | (NR) | (NR) |
| 1,2,3-trichloropropane | µg/L | 1 | Org-013 | <1 | (NT) | (NT) | (NR) | (NR) |
| Isopropylbenzene | µg/L | 1 | Org-013 | <1 | (NT) | (NT) | (NR) | (NR) |
| Bromobenzene | µg/L | 1 | Org-013 | <1 | (NT) | (NT) | (NR) | (NR) |
| n-propyl benzene | µg/L | 1 | Org-013 | <1 | (NT) | (NT) | (NR) | (NR) |
| 2-chlorotoluene | µg/L | 1 | Org-013 | <1 | (NT) | (NT) | (NR) | (NR) |
| 4-chlorotoluene | µg/L | 1 | Org-013 | <1 | (NT) | (NT) | (NR) | (NR) |
| 1,3,5-trimethylbenzene | µg/L | 1 | Org-013 | <1 | (NT) | (NT) | (NR) | (NR) |
| Tert-butyl benzene | µg/L | 1 | Org-013 | <1 | (NT) | (NT) | (NR) | (NR) |
| 1,2,4-trimethyl benzene | µg/L | 1 | Org-013 | <1 | (NT) | (NT) | (NR) | (NR) |
| 1,3-dichlorobenzene | µg/L | 1 | Org-013 | <1 | (NT) | (NT) | (NR) | (NR) |
| Sec-butyl benzene | µg/L | 1 | Org-013 | <1 | (NT) | (NT) | (NR) | (NR) |
| 1,4-dichlorobenzene | µg/L | 1 | Org-013 | <1 | (NT) | (NT) | (NR) | (NR) |
| 4-isopropyl toluene | µg/L | 1 | Org-013 | <1 | (NT) | (NT) | (NR) | (NR) |
| 1,2-dichlorobenzene | µg/L | 1 | Org-013 | <1 | (NT) | (NT) | (NR) | (NR) |

-continued

|  | Units | PQL | Method | Blank | Duplicate Sm# | Duplicate results | Spike Sm# | Spike % Recovery |
|---|---|---|---|---|---|---|---|---|
| n-butyl benzene | μg/L | 1 | Org-013 | <1 | (NT) | (NT) | (NR) | (NR) |
| 1,2-dibromo-3-chloropropane | μg/L | 1 | Org-013 | <1 | (NT) | (NT) | (NR) | (NR) |
| 1,2,4-trichlorobenzene | μg/L | 1 | Org-013 | <1 | (NT) | (NT) | (NR) | (NR) |
| Hexachlorobutadiene | μg/L | 1 | Org-013 | <1 | (NT) | (NT) | (NR) | (NR) |
| 1,2,3-trichlorobenzene | μg/L | 1 | Org-013 | <1 | (NT) | (NT) | (NR) | (NR) |
| Surrogate Dibromofluoromethane | % |  | Org-013 | 100 | (NT) | (NT) | LCS-W1 | 99% |
| Surrogate toluene-d8 | % |  | Org-013 | 99 | (NT) | (NT) | LCS-W1 | 98% |
| Surrogate 4-BFB | % |  | Org-013 | 104 | (NT) | (NT) | LCS-W1 | 101% |
| Quality Control vTRH(C6-C10)/BTEX in Water |  |  |  |  |  |  |  |  |
| Date Extracted |  |  |  | 19 Aug. 2014 | (NT) | (NT) | LCS-W1 | 19 Aug. 2014 |
| Date Analysed |  |  |  | 22 Aug. 2014 | (NT) | (NT) | LCS-W1 | 22 Aug. 2014 |
| TRH $C_6$-$C_9$ | μg/L | 10 | Org-016 | <10 | (NT) | (NT) | LCS-W1 | 107% |
| TRH $C_6$-$C_{10}$ | μg/L | 10 | Org-016 | <10 | (NT) | (NT) | LCS-W1 | 107% |
| Benzene | μg/L | 1 | Org-016 | <1 | (NT) | (NT) | LCS-W1 | 104% |
| Toluene | μg/L | 1 | Org-016 | <1 | (NT) | (NT) | LCS-W1 | 107% |
| Ethylbenzene | μg/L | 1 | Org-016 | <1 | (NT) | (NT) | LCS-W1 | 107% |
| m + p-xylene | μg/L | 2 | Org-016 | <2 | (NT) | (NT) | LCS-W1 | 109% |
| o-xylene | μg/L | 1 | Org-016 | <1 | (NT) | (NT) | LCS-W1 | 110% |
| Naphtalene | μg/L | 1 | Org-016 | <1 | (NT) | (NT) | (NR) | (NR) |
| Surrogate Dibromofluoromethane | % |  | Org-016 | 100 | (NT) | (NT) | LCS-W1 | 99% |
| Surrogate toluene-d8 | % |  | Org-016 | 99 | (NT) | (NT) | LCS-W1 | 99% |
| Surrogate 4-BFB | % |  | Org-016 | 104 | (NT) | (NT) | LCS-W1 | 100% |
| Quality Control svTRH(C10-C40) in Water |  |  |  |  |  |  |  |  |
| Date extracted |  |  |  | 18 Aug. 2014 | (NT) | (NT) | LCS-W2 | 18 Aug. 2014 |
| Date analysed |  |  |  | 18 Aug. 2014 | (NT) | (NT) | LCS-W2 | 18 Aug. 2014 |
| TRH $C_{10}$-$C_{14}$ | μg/L | 50 | Org-003 | <50 | (NT) | (NT) | LCS-W2 | 88% |
| TRH $C_{15}$-$C_{28}$ | μg/L | 100 | Org-003 | <100 | (NT) | (NT) | LCS-W2 | 86% |
| TRH $C_{29}$-$C_{36}$ | μg/L | 100 | Org-003 | <100 | (NT) | (NT) | LCS-W2 | 84% |
| TRH > $C_{10}$-$C_{16}$ | μg/L | 50 | Org-003 | <50 | (NT) | (NT) | LCS-W2 | 88% |
| TRH > $C_{16}$-$C_{34}$ | μg/L | 100 | Org-003 | <100 | (NT) | (NT) | LCS-W2 | 86% |
| TRH > $C_{34}$-$C_{40}$ | μg/L | 100 | Org-003 | <100 | (NT) | (NT) | LCS-W2 | 84% |
| Surrogate o-Terphenyl | % |  | Org-003 | 90 | (NT) | (NT) | LCS-W2 | 71% |
| Quality Control HM in water - total |  |  |  |  |  |  |  |  |
| Date prepared |  |  |  | 18 Aug. 2014 | (NT) | (NT) | LCS-W2 | 18 Aug. 2014 |
| Date analysed |  |  |  | 18 Aug. 2014 | (NT) | (NT) | LCS-W2 | 18 Aug. 2014 |
| Arsenic - total | μg/L | 1 | Metals-022 ICP-MS | <1 | (NT) | (NT) | LCS-W2 | 106% |
| Cadmium- Total | μg/L | 0.1 | Metals-022 ICP-MS | <0.1 | (NT) | (NT) | LCS-W2 | 118% |
| Chromium - Total | μg/L | 1 | Metals-022 ICP-MS | <1 | (NT) | (NT) | LCS-W2 | 110% |
| Copper - Total | μg/L | 1 | Metals-022 ICP-MS | <1 | (NT) | (NT) | LCS-W2 | 91% |
| Lead -Total | μg/L | 1 | Metals-022 ICP-MS | <1 | (NT) | (NT) | LCS-W2 | 117% |
| Mercury - Total | μg/L | 0.05 | Metals-021 CV-AAS | <0.05 | (NT) | (NT) | LCS-W2 | 96% |
| Nickel - Total | μg/L | 1 | Metals-022 ICP-MS | <1 | (NT) | (NT) | LCS-W2 | 103% |
| Zinc - Total | μg/L | 1 | Metals-022 ICP-MS | <1 | (NT) | (NT) | LCS-W2 | 109% |
| Quality Control Metals in Waters-Acid extractable |  |  |  |  |  |  |  |  |
| Date prepared |  |  |  | 18 Aug. 2014 | (NT) | (NT) | LCS-W1 | 18 Aug. 2014 |
| Date analysed |  |  |  | 18 Aug. 2014 | (NT) | (NT) | LCS-W1 | 19 Aug. 2014 |
| Sulfur - Total | mg/L | 0.5 | Metals-020 ICP-AES | 93 | (NT) | (NT) | LCS-W1 | 93% |

|  | Units | PQL | Method | Blank | Duplicate Sm# | Duplicate results | Spike Sm# | Spike % Recovery |
|---|---|---|---|---|---|---|---|---|
| Quality Control Miscellaneous Inorganics | | | | | | | | |
| Date prepared | | | | 15 Aug. 2014 | 114714-1 | 15 Aug. 2014 II 15 Aug. 2014 | LCS-W1 | 15 Aug. 2014 |
| Date analysed | | | | 15 Aug. 2014 | 114714-1 | 15 Aug. 2014 II 15 Aug. 2014 | LCS-W1 | 15 Aug. 2014 |
| pH | pH Units | | Inorg-001 | (NT) | 114714-1 | 7.0 II (NT) | LCS-W1 | 101% |
| Total Dissolved Solids (grav) | mg/L | 5 | Inorg-018 | <5 | 114714-1 | 15000 II (NT) | LCS-W1 | 95% |
| BOD | mg/L | 5 | Inorg-091 | <5 | 114714-1 | 600 II (NT) | LCS-W1 | 84% |
| COD | mg $O_2$/L | 50 | Inorg-067 | <50 | 114714-1 | 19000 II 19000 | LCS-W1 | 84% |
| Total Organic Carbon | mg/L | 1 | Inorg-079 | <1 | 114714-1 | 5900 II 5800 | LCS-W1 | 104% |
| Quality Control Cations in water-Total | | | | | | | | |
| Date digested | | | | 18 Aug. 2014 | (NT) | (NT) | LCS-W1 | 18 Aug. 2014 |
| Date analysed | | | | 18 Aug. 2014 | (NT) | (NT) | LCS-W1 | 18 Aug. 2014 |
| Sodium -Total | mg/L | 0.5 | Metals-020 ICP-AES | <0.5 | (NT) | (NT) | LCS-W1 | 102% |
| Potassium -Total | mg/L | 0.5 | Metals-020 ICP-AES | <0.5 | (NT) | (NT) | LCS-W1 | 97% |
| Calcium -Total | mg/L | 0.5 | Metals-020 ICP- AES | <0.5 | (NT) | (NT) | LCS-W1 | 104% |
| Magnesium - Total | mg/L | 0.5 | Metals-020 ICP-AES | <0.5 | (NT) | (NT) | LCS-W1 | 108% |

TABLE 35

Water Analysis (Radiata Pine Wood Flour w/- Black Liquor 20140523)

|  |  | Mixed Feedstocks 20140814 | Hog Fuel Sodium Hydroxide 20140716 | Pyrolysed Paper Sludge Black Liquor 20140528 | Radiata Pine Black Liquor 20140523 |
|---|---|---|---|---|---|
| Our Reference: | | 114714-1 | 113424-1 | 110678-1 | 110463-1 |
| Your Reference: | | 20140814 | 20140716 | 20140528 | 20140523 |
| Type of sample | Units | Water | Water | Water | Water |
| VOCs in water | | | | | |
| Date extracted | | 19 Aug. 2014 | 23 Jul. 2014 | 29 May 2014 | 28 May 2014 |
| Date analysed | | 22 Aug. 2014 | 23 Jul. 2014 | 30 May 2014 | 29 May 2014 |
| Dichlorodifluoromethane | μg/L | <1000 | <1000 | <5000 | <1000 |
| Chloromethane | μg/L | <1000 | <1000 | <5000 | <1000 |
| Vinyl Chloride | μg/L | <1000 | <1000 | <5000 | <1000 |
| Bromomethane | μg/L | <1000 | <1000 | <5000 | <1000 |
| Chloroethane | μg/L | <1000 | <1000 | <5000 | <1000 |
| Trichlorofluoromethane | μg/L | <1000 | <1000 | <5000 | <1000 |
| 1,1-Dichloroethane | μg/L | <100 | <100 | <500 | <100 |
| Trans-1,2-dichloroethene | μg/L | <100 | <100 | <500 | <100 |
| Bromochloromethane | μg/L | <100 | <100 | <500 | <100 |
| Chloroform | μg/L | <100 | <100 | <500 | <100 |
| 2,2-dichloropropane | μg/L | <100 | <100 | <500 | <100 |
| 1,2-dichloroethane | μg/L | <100 | <100 | <500 | <100 |
| 1,1,1-trichloroethane | μg/L | <100 | <100 | <500 | <100 |
| 1,1-dichloropropene | μg/L | <100 | <100 | <500 | <100 |
| Cyclohexande | μg/L | <100 | <100 | <500 | <100 |
| Carbon tetrachloride | μg/L | <100 | <100 | <500 | <100 |
| Benzene | μg/L | <180 | 340 | <500 | 340 |
| Dibromomethane | μg/L | <100 | <100 | <500 | <100 |
| 1,2-dichloropropane | μg/L | <100 | <100 | <500 | <100 |
| Trichloroethene | μg/L | <100 | <100 | <500 | <100 |
| Bromodichloromethane | μg/L | <100 | <100 | <500 | <100 |
| trans-1,3-dichloropropene | μg/L | <100 | <100 | <500 | <100 |
| cis-1,3-dichloropropene | μg/L | <100 | <100 | <500 | <100 |
| 1,1,2-trichloroethane | μg/L | <100 | <100 | <500 | <100 |
| Toluene | μg/L | 370 | 890 | 810 | 680 |
| 1,3-dichloropropane | μg/L | <100 | <100 | <500 | <100 |
| Dibromochloromethane | μg/L | <100 | <100 | <500 | <100 |
| 1,2-dibromoethane | μg/L | <100 | <100 | <500 | <100 |
| Tetrachloroethene | μg/L | <100 | <100 | <500 | <100 |

TABLE 35-continued

Water Analysis (Radiata Pine Wood Flour w/- Black Liquor 20140523)

| Our Reference:<br>Your Reference:<br>Type of sample | Units | Mixed<br>Feedstocks<br>20140814<br>114714-1<br>20140814<br>Water | Hog Fuel<br>Sodium<br>Hydroxide<br>20140716<br>113424-1<br>20140716<br>Water | Pyrolysed<br>Paper<br>Sludge Black<br>Liquor<br>20140528<br>110678-1<br>20140528<br>Water | Radiata<br>Pine<br>Black<br>Liquor<br>20140523<br>110463-1<br>20140523<br>Water |
|---|---|---|---|---|---|
| 1,1,1,2-tetrachloroethane | µg/L | <100 | <100 | <500 | <100 |
| Chlorobenzene | µg/L | <100 | <100 | <500 | <100 |
| Ethylbenzene | µg/L | <100 | 120 | <500 | <100 |
| Bromoform | µg/L | <100 | <100 | <500 | <100 |
| m + p-xylene | µg/L | 200 | <200 | <1000 | <200 |
| Styrene | µg/L | <100 | <100 | <500 | <100 |
| 1,1,2,2-tetrachlororethane | µg/L | <100 | <100 | <500 | <100 |
| o-xylene | µg/L | <100 | <120 | <500 | <100 |
| 1,2,3-trichloropropane | µg/L | <100 | <100 | <500 | <100 |
| Isopropylbenzene | µg/L | <100 | <100 | <500 | <100 |
| Bromobenzene | µg/L | <100 | <100 | <500 | <100 |
| n-propyl benzene | µg/L | <100 | <100 | <500 | <100 |
| 2-chlorotoluene | µg/L | <100 | <100 | <500 | <100 |
| 4-chlorotoluene | µg/L | <100 | <100 | <500 | <100 |
| 1,3,5-trimethylbenzene | µg/L | <100 | <100 | <500 | <100 |
| Tert-butyl benzene | µg/L | <100 | <100 | <500 | <100 |
| 1,2,4-trimethyl benzene | µg/L | <100 | <100 | <500 | <100 |
| 1,3-dichlorobenzene | µg/L | <100 | <100 | <500 | <100 |
| Sec-butyl benzene | µg/L | <100 | <100 | <500 | <100 |
| 1,4-dichlorobenzene | µg/L | <100 | <100 | <500 | <100 |
| 4-isopropyl toluene | µg/L | <100 | <100 | <500 | <100 |
| 1,2-dichlorobenzene | µg/L | <100 | <100 | <500 | <100 |
| n-butyl benzene | µg/L | <100 | <100 | <500 | <100 |
| 1,2-dibromo-3-chloropropane | µg/L | <100 | <100 | <500 | <100 |
| 1,2,4-trichlorobenzene | µg/L | <100 | <100 | <500 | <100 |
| Hexachlorobutadiene | µg/L | <100 | <100 | <500 | <100 |
| 1,2,3-trichlorobenzene | µg/L | <100 | <100 | <500 | <100 |
| Surrogate Dibromofluoromethane | % | 100% | 106% | 112% | 105% |
| Surrogate toluene-d8 | % | 101% | 105% | 100% | 100% |
| Surrogate 4-BFB | % | 106% | 95% | 100% | 99% |
| vTRH(C6-C10)/BTEXN in Water | | | | | |
| Date extracted | | 19 Aug. 2014 | 23 Jul. 2014 | 29 May 2014 | 28 May 2014 |
| Date analysed | | 22 Aug. 2014 | 23 Jul. 2014 | 30 May 2014 | 29 May 2014 |
| TRH$C_6$-$C_9$ | µg/L | 31,000 | 42,000 | 26,000 | 33,000 |
| TRH$C_6$-$C_{10}$ | µg/L | 34,000 | 50,000 | 27,000 | 36,000 |
| TRH$C_6$-$C_{10}$ less BTEX (F1) | µg/L | 33,000 | 49,000 | 26,000 | 35,000 |
| Benzene | µg/L | 180 | 430 | <500 | 340 |
| Toluene | µg/L | 370 | 890 | 810 | 680 |
| Ethylbenzene | µg/L | <100 | 120 | <500 | 130 |
| m+p-xylene | µg/L | <200 | <200 | <1000 | <200 |
| o-xylene | µg/L | <100 | 120 | <500 | <100 |
| Naphtalene | µg/L | <100 | <100 | <500 | <100 |
| Surrogate Dibromofluoromethane | % | 100% | 106% | 112% | 105% |
| Surrogate toluene-d8 | % | 101% | 105% | 100% | 100% |
| Surrogate 4-BFB | % | 106% | 95% | 100% | 99% |
| svTRH(C10-C40) in Water | | | | | |
| Date extracted | | 19 Aug. 2014 | 24 Jul. 2014 | 30 May 2014 | 28 May 2014 |
| Date analysed | | 22 Aug. 2014 | 24 Jul. 2014 | 31 May 2014 | 29 May 2014 |
| TRH$C_{10}$-$C_{14}$ | µg/L | 650,000 | 430,000 | 25,000 | 860,000 |
| TRH$C_{15}$-$C_{28}$ | µg/L | 490,000 | 190,000 | 160,000 | 510,000 |
| TRH$C_{29}$-$C_{36}$ | µg/L | 14,000 | 6,600 | 16,000 | 18,000 |
| TRH > $C_{10}$-$C_{15}$ | µg/L | 800,000 | 450,000 | 260,000 | 860,000 |
| TRH > $C_{10}$-$C_{15}$ less Naphtalene (F2) | µg/L | 800,000 | 450,000 | 260,000 | 860,000 |
| TRH > $C_{15}$-$C_{34}$ | µg/L | 180,000 | 91,000 | 120,000 | 260,000 |
| TRH > $C_{34}$-$C_{40}$ | µg/L | 1,800 | <1,000 | 4,800 | 5,300 |
| Surrogate a-Terphenyl | % | # | # | # | # |
| HM in Water - Total | | | | | |
| Date prepared | | 18 Aug. 2014 | 23 Jul. 2014 | 30 May 2014 | 27 May 2014 |
| Date analysed | | 18 Aug. 2014 | 23 Jul. 2014 | 30 May 2014 | 27 May 2014 |
| Arsenic - total | µg/L | 45 | 2 | 29 | 27 |
| Cadmium - total | µg/L | 0.1 | <0.1 | 5.7 | <0.1 |
| Chromium - total | µg/L | 1 | 1 | 110 | <1 |
| Copper - total | µg/L | 1 | <1 | 180 | 1 |

TABLE 35-continued

Water Analysis (Radiata Pine Wood Flour w/- Black Liquor 20140523)

| Our Reference:<br>Your Reference:<br>Type of sample | Units | Mixed<br>Feedstocks<br>20140814<br>114714-1<br>20140814<br>Water | Hog Fuel<br>Sodium<br>Hydroxide<br>20140716<br>113424-1<br>20140716<br>Water | Pyrolysed<br>Paper<br>Sludge Black<br>Liquor<br>20140528<br>110678-1<br>20140528<br>Water | Radiata<br>Pine<br>Black<br>Liquor<br>20140523<br>110463-1<br>20140523<br>Water |
|---|---|---|---|---|---|
| Lead - Total | μg/L | 1 | <1 | 40 | <1 |
| Mercury - Total | μg/L | 0.3 | 0.06 | 1 | 0.58 |
| Nickel - Total | μg/L | 1 | <1 | 97 | <1 |
| Zinc - Total | μg/L | 44 | 8 | 1,100 | 14 |
| Metals in Waters - Acid extractable | | | | | |
| Date prepared | | 18 Aug. 2014 | 23 Jul. 2014 | 30 May 2014 | 27 May 2014 |
| Date analysed | | 18 Aug. 2014 | 23 Jul. 2014 | 30 May 2014 | 27 May 2014 |
| Sulfur - Total | mg/L | 840 | 6.3 | 26 | 150 |
| Miscellaneous Inorganics | | | | | |
| Date prepared | | 15 Aug. 2014 | 22 Jul. 2014 | 29 May 2014 | 26 May 2014 |
| Date analysed | | 15 Aug. 2014 | 22 Jul. 2014 | 29 May 2014 | 26 May 2014 |
| pH | pH Units | 7 | 7.8 | 9.7 | 6.3 |
| Total Dissolved Solids (grav) | mg/L | 15,000 | 630 | 26,000 | 9,800 |
| BOD | mg/L | 600 | 7,200 | 6,900 | 11,000 |
| COD | mg $O_2$/L | 19,000 | 18,000 | 50,000 | 24,000 |
| Total Organic Carbon | mg/L | 5,900 | 6,500 | 17,000 | 6,600 |
| Cations in water - Total | | | | | |
| Date digested | | 18 Aug. 2014 | 23 Jul. 2014 | 30 May 2014 | 27 May 2014 |
| Date analysed | | 18 Aug. 2014 | 23 Jul. 2014 | 30 May 2014 | 27 May 2014 |
| Sodium - total | mg/L | 2,300 | 5,200 | 5,500 | 2,100 |
| Potassium - total | mg/L | 190 | 54 | 16 | 150 |
| Calcium - total | mg/L | 16 | <0.5 | 680 | 3.8 |
| Magnesium - total | mg/L | 3.4 | 1.6 | 270 | 2.5 |

TABLE 36

Water Analysis (Radiata Pine Wood Flour w/- Black Liquor 20140523)

| VOCs in water<br>Our Reference:<br>Your Reference<br>Type of sample<br>Date extracted<br>Date analysed | Units | Mixed<br>Feedstocks<br>20140814<br>114714-1<br>20140814<br>Water<br>19 Aug. 2014<br>22 Aug. 2014 | Hog Fuel<br>Sodium<br>Hydroxide<br>20140716<br>113424-1<br>20140716<br>Water<br>23 Jul. 2014<br>23 Jul. 2014 | Pyrolysed<br>Paper<br>Sludge Black<br>Liquor<br>20140528<br>110678-1<br>20140528<br>Water<br>29 May 2014<br>30 May 2014 | Radiata<br>Black Liquor<br>20140523<br>110463-1<br>20140523<br>Water<br>28 May 2014<br>29 May 2014 |
|---|---|---|---|---|---|
| Dichlorodifluoromethane | μg/L | <1,000 | <1,000 | <5,000 | <1,000 |
| Chloromethane | μg/L | <1,000 | <1,000 | <5,000 | <1,000 |
| Vinyl Chloride | μg/L | <1,000 | <1,000 | <5,000 | <1,000 |
| Bromomethane | μg/L | <1,000 | <1,000 | <5,000 | <1,000 |
| Chloroethane | μg/L | <1,000 | <1,000 | <5,000 | <1,000 |
| Trichlorofluoromethane | μg/L | <1,000 | <1,000 | <5,000 | <1,000 |
| 1,1-Dichloroethane | μg/L | <100 | <100 | <500 | <100 |
| Trans-1,2-dichloroethane | μg/L | <100 | <100 | <500 | <100 |
| 1,1-dichloroethane | μg/L | <100 | <100 | <500 | <100 |
| Cis-1,2-dichloroethane | μg/L | <100 | <100 | <500 | <100 |
| Bromochloromethane | μg/L | <100 | <100 | <500 | <100 |
| Chloroform | μg/L | <100 | <100 | <500 | <100 |
| 2,2-dichloropropane | μg/L | <100 | <100 | <500 | <100 |
| 1,2-dichloroethane | μg/L | <100 | <100 | <500 | <100 |
| 1,1,1-trichloroethane | μg/L | <100 | <100 | <500 | <100 |
| 1,1-dichloropropene | μg/L | <100 | <100 | <500 | <100 |
| Cyclohexane | μg/L | <100 | <100 | <500 | <100 |
| Carbon tetrachloride | μg/L | <100 | <100 | <500 | <100 |
| Benzene | μg/L | <180 | 340 | <500 | 340 |
| Dibromomethane | μg/L | <100 | <100 | <500 | <100 |
| 1,2-dichloropropane | μg/L | <100 | <100 | <500 | <100 |

TABLE 36-continued

Water Analysis (Radiata Pine Wood Flour w/- Black Liquor 20140523)

| | | | | | |
|---|---|---|---|---|---|
| Trichloroethene | µg/L | <100 | <100 | <500 | <100 |
| Bromodichloromethane | µg/L | <100 | <100 | <500 | <100 |
| trans-1,3-dichloropropene | µg/L | <100 | <100 | <500 | <100 |
| cis-1,3-dichloropropene | µg/L | <100 | <100 | <500 | <100 |
| 1,1,2-trichloroethane | µg/L | <100 | <100 | <500 | <100 |
| Toluene | µg/L | 370 | 890 | 810 | 680 |
| 1,3-dichloropropane | µg/L | <100 | <100 | <500 | <100 |
| Dibromochloromethane | µg/L | <100 | <100 | <500 | <100 |
| 1,2-dibromoethane | µg/L | <100 | <100 | <500 | <100 |
| Tetrachloroethane | µg/L | <100 | <100 | <500 | <100 |
| 1,1,1,2-tetrachloroethane | µg/L | <100 | <100 | <500 | <100 |
| Chlorobenzene | µg/L | <100 | <100 | <500 | <100 |
| Ethylbenzene | µg/L | <100 | 120 | <500 | <130 |
| Bromoform | µg/L | <100 | <100 | <500 | <100 |
| m + p-xylene | µg/L | 200 | <200 | <1000 | <200 |
| Styrene | µg/L | <100 | <100 | <500 | <100 |
| 1,1,2,2-tetrachloroethane | µg/L | <100 | <100 | <500 | <100 |
| o-xylene | µg/L | <100 | <120 | <500 | <100 |
| 1,2,3-trichloropropane | µg/L | <100 | <100 | <500 | <100 |
| Isopropylbenzene | µg/L | <100 | <100 | <500 | <100 |
| Bromobenzene | µg/L | <100 | <100 | <500 | <100 |
| n-propyl benzene | µg/L | <100 | <100 | <500 | <100 |
| 2-chlorotoluene | µg/L | <100 | <100 | <500 | <100 |
| 4-chlorotoluene | µg/L | <100 | <100 | <500 | <100 |
| 1,3,5-trimethyl benzene | µg/L | <100 | <100 | <500 | <100 |
| Tert-butyl benzene | µg/L | <100 | <100 | <500 | <100 |
| 1,2,4-trimethyl benzene | µg/L | <100 | <100 | <500 | <100 |
| 1,3-dichlorobenzene | µg/L | <100 | <100 | <500 | <100 |
| Sec-butyl benzene | µg/L | <100 | <100 | <500 | <100 |
| 1,4-dichlorobenzene | µg/L | <100 | <100 | <500 | <100 |
| 4-isopropyl toluene | µg/L | <100 | <100 | <500 | <100 |
| 1,2-dichlorobenzene | µg/L | <100 | <100 | <500 | <100 |
| n-butyl benzene | µg/L | <100 | <100 | <500 | <100 |
| 1,2-dibromo-3-chloropropane | µg/L | <100 | <100 | <500 | <100 |
| 1,2,4-trichlorobenzene | µg/L | <100 | <100 | <500 | <100 |
| Hexachlorobutadiene | µg/L | <100 | <100 | <500 | <100 |
| 1,2,3-trichlorobenzene | µg/L | <100 | <100 | <500 | <100 |
| Surrogate Dibromofluoromethane | µg/L | 100% | 106% | 112% | 105% |
| Surrogate toluene-d8 | µg/L | 101% | 105% | 100% | 100% |
| Surrogate 4-BFB | µg/L | 106% | 95% | 100% | 99% |

| vTRH(C6-C10)/BTEXN in Water | | Mixed Feedstocks 20140814 | Hog Fuel Sodium Hydroxide 20140716 | Pyrolysed Paper Sludge Black Liquor 20140528 | Radiata Black Liquor 20140523 |
|---|---|---|---|---|---|
| Our Reference: | | 114714-1 | 113424-1 | 110678-1 | 110463-1 |
| Your Reference | | 20140814 | 20140716 | 20140528 | 20140523 |
| Type of sample | | Water | Water | Water | Water |
| Date extracted | | 19 Aug. 2014 | 23 Jul. 2014 | 29 May 2014 | 28 May 2014 |
| Date analysed | Units | 22 Aug. 2014 | 23 Jul. 2014 | 30 May 2014 | 29 May 2014 |
| TRH C6-C9 | µg/L | 31,000 | 42,000 | 26,000 | 33,000 |
| TRH C6-C10 | µg/L | 34,000 | 50,000 | 27,000 | 36,000 |
| TRH C6-C10 less BTEX (F1) | µg/L | 33,000 | 49,000 | 26,000 | 35,000 |
| Benzene | µg/L | 180 | 430 | <500 | 340 |
| Toluene | µg/L | 370 | 890 | 810 | 680 |
| Ethylbenzene | µg/L | <100 | 120 | <500 | 130 |
| m + p-xylene | µg/L | <200 | <200 | <1000 | <200 |
| o-xylene | µg/L | <100 | 120 | <500 | <100 |
| Naphthalene | µg/L | <100 | <100 | <501 | <100 |
| Surrogate Dibromofluromethane | µg/L | 100% | 106% | 112% | 105% |
| Surrogate toluene-d8 | µg/L | 101% | 105% | 100% | 100% |
| Surrogate 4-BFB | µg/L | 106% | 95% | 100% | 99% |

| svTRH (C10-C40) in Water | | | | Water | |
|---|---|---|---|---|---|
| Our Reference: | | 114714-1 | 113424-1 | 110678-1 | 110463-1 |
| Your Reference | | 20140814 | 20140716 | 20140528 | 20140523 |
| Type of sample | | Water | Water | Water | Water |
| Date extracted | | 18 Aug. 2014 | 24 Jul. 2014 | 30 May 2014 | 28 May 2014 |
| Date analysed | | 19 Aug. 2014 | 24 Jul. 2014 | 31 May 2014 | 29 May 2014 |
| TRH C10-C14 | µg/L | 650,000 | 430,000 | 25,000 | 860,000 |
| TRH C15-C28 | µg/L | 490,000 | 190,000 | 160,000 | 510,000 |
| TRH C29-C36 | µg/L | 14,000 | 6,600 | 16,000 | 18,000 |
| TRH >C10-C16 | µg/L | 800,000 | 450,000 | 260,000 | 860,000 |
| TRH >C10-C16 less Naphthalene (F2) | µg/L | 800,000 | 450,000 | 260,000 | 860,000 |

TABLE 36-continued

Water Analysis (Radiata Pine Wood Flour w/- Black Liquor 20140523)

| | | | | | |
|---|---|---|---|---|---|
| TRH >C16-C34 | μg/L | 180,000 | 91,000 | 120,000 | 260,000 |
| TRH >C34-C40 | μg/L | 1,800 | <1,000 | 4,800 | 5,300 |
| Surrogate o-Terphenyl | % | # | # | # | # |
| HM in water - total | | | | | |
| Our Reference: | | 114714-1 | 113424-1 | 110678-1 | 110463-1 |
| Your Reference | | 20140814 | 20140716 | 20140528 | 20140523 |
| Type of sample | | Water | Water | Water | Water |
| Date prepared | | 18 Aug. 2014 | 23 Jul. 2014 | 30 May 2014 | 27 May 2014 |
| Date analysed | | 18 Aug. 2014 | 23 Jul. 2014 | 30 May 2014 | 27 May 2014 |
| Arsenic-Total | μg/L | 45 | 2 | 29 | 27 |
| Cadmium-Total | μg/L | 0.1 | <01 | 5.7 | <0.1 |
| Chromium-Total | μg/L | 1 | 1 | 110 | <1 |
| Copper-Total | μg/L | 1 | <1 | 180 | 1 |
| Lead-Total | μg/L | 1 | <1 | 40 | <1 |
| Mercury-Total | μg/L | 0.3 | 0.06 | 1 | 0.58 |
| Nickel-Total | μg/L | 1 | <1 | 97 | <1 |
| Zinc-Total | μg/L | 44 | 8 | 1,100 | 14 |
| Metals in Waters - Acid extractable | | | | | |
| Our Reference: | | 114714-1 | 113424-1 | 110678-1 | 110463-1 |
| Your Reference | | 20140814 | 20140716 | 20140528 | 20140523 |
| Type of sample | | Water | Water | Water | Water |
| Date prepared | | 18 Aug. 2014 | 23 Jul. 2014 | 30 May 2014 | 27 May 2014 |
| Date analysed | | 18 Aug. 2014 | 23 Jul. 2014 | 30 May 2014 | 27 May 2014 |
| Sulfur-Total | mg/L | 840 | 6.3 | 26 | 150 |
| Miscellaneous Inorganics | | | | | |
| Our Reference: | | 114714-1 | 113424-1 | 110678-1 | 110463-1 |
| Your Reference | | 20140814 | 20140716 | 20140528 | 20140523 |
| Type of sample | | Water | Water | Water | Water |
| Date prepared | | 15 Aug. 2014 | 22 Jul. 2014 | 29 May 2014 | 26 May 2014 |
| Date analysed | | 15 Aug. 2014 | 22 Jul. 2014 | 29 May 2014 | 26 May 2014 |
| pH | pH Units | 7 | 7.8 | 9.7 | 6.3 |
| Total Dissolved Solids (grav) | mg/L | 15,000 | 630 | 26,000 | 9,800 |
| BOD | mg/L | 600 | 7,200 | 6,900 | 11,000 |
| COD | mg O2/L | 19,000 | 18,000 | 50,000 | 24,000 |
| Total Organic Carbon | mg/L | 5,900 | 6,500 | 17,000 | 6,600 |
| Cations in water - Total | | | | | |
| Our Reference: | | 114714-1 | 113424-1 | 110678-1 | 110463-1 |
| Your Reference: | | 20140814 | 20140716 | 20140528 | 20140523 |
| Type of sample | | 18 Aug. 2014 | Water | Water | Water |
| Date digested | | 18 Aug. 2014 | 23 Jul. 2014 | 30 May 2014 | 27 May 2014 |
| Date analysed | | 18 Aug. 2015 | 23 Jul. 2014 | 30 May 2014 | 27 May 2014 |
| Sodium - total | mg/L | 2,300 | 5,200 | 5,500 | 2,100 |
| Potassium - total | mg/L | 190 | 54 | 16 | 150 |
| Calcium - total | mg/L | 16 | <0.5 | 680 | 3.8 |
| Magnesium - total | mg/L | 3.4 | 1.6 | 270 | 2.5 |

TABLE 37

Feedstock Comparison

| Run # | Description | Proximate Analysis | | | | Ultimate Analysis | | | | | | | Molar H/C Ratio |
|---|---|---|---|---|---|---|---|---|---|---|---|---|---|
| | | Moisture (% wt ar) | Ash (% wt db) | Volatiles (% wt db) | Fixed C. (% wt db) | GCV (MJ/kg db) | Carbon (% wt db) | Hydrogen (% wt db) | Nitrogen (% wt db) | Sulphur (% wt db) | Oxygen (% wt db) | Chlorine (%) | |
| | radiata pine 150 um | 9 | 0.50 | 79.30 | 20.20 | 21.30 | 52.50 | 6.10 | <0.01 | 0.02 | 40.88 | n/a | 1.38 |
| 1 | SPF wood | 43.8 | 0.6 | 79.5 | 19.9 | 18.6 | 52.1 | 6.3 | 0.21 | | 40.8 | | 1.45 |
| | Hog Fuel | 60.0 | 2.2 | 74.4 | 23.5 | 22.8 | 52.9 | 6.0 | 0.25 | | 38.7 | | 1.36 |
| 2, 3 | Black Liquor | 53.9 | 47.07 | | | | 37.53 | 1.67 | <0.01 | 4.77 | 3.23 | 0.21 | 0.53 |
| | Sludge, as received | 6.4 | 9.7 | 80.4 | 10.0 | 13.82 | 42.8 | 5.7 | 0.23 | | 41.57 | | 1.60 |

TABLE 38

Additional information on Radiata pine wood
Biochemical Composition

| Cellulose (% wt db) | Hemicell. (% wt db) | Lignin (% wt db) | Extractives (% wt db) |
|---|---|---|---|
| 47.03 | 10.39 | 35.96 | 6.47 |

TABLE 39

Feedstock Comparison

| | | Ash Constituents | | | | | | | |
|---|---|---|---|---|---|---|---|---|---|
| Run # | Description | SiO2 (% wt db) | Al2O3 (% wt db) | Fe2O3 (% wt db) | TiO2 (% wt db) | K2O (% wt db) | MgO (% wt db) | Na2O (% wt db) | CaO (% wt db) |
| | radiata pine 150um | 16.10 | 3.10 | 1.60 | 0.14 | 13.30 | 9.80 | 1.60 | 25.70 |
| 1 | SPF wood | 2.3 | 1.1 | 0.69 | 0.04 | 16.3 | 7.9 | 0.42 | 33.9 |
| | Hog Fuel | 1.1 | 0.62 | 0.28 | 0.02 | 7.6 | 3.2 | 0.30 | 46.7 |
| | Sludge, as received | 9.8 | 1.1 | 1.2 | 0.08 | 0.30 | 11.8 | 2.8 | 40.4 |
| 4 | Pyrolysed sludge | | | | | | | | |

| | | Ash Constituents | | | | | | |
|---|---|---|---|---|---|---|---|---|
| Run # | Description | SO3 (% wt db) | P2O5 (% wt db) | Mn3O4 (% wt db) | SrO (% wt db) | BaO (% wt db) | ZnO (% wt db) | V2O5 (% wt db) |
| | radiata pine 150um | 13.10 | 6.60 | 1.40 | 0.11 | 0.07 | 0.20 | <0.01 |
| 1 | SPF wood | 1.2 | 2.2 | 2.3 | 0.12 | 0.30 | 0.28 | 0.00 |
| | Hog Fuel | 1.0 | 2.5 | 1.5 | 0.24 | 0.60 | 0.42 | 0.00 |
| | Sludge, as received | 2.4 | 0.41 | 0.38 | 0.05 | 0.06 | 0.05 | 0.00 |
| 4 | Pyrolysed sludge | | | | | | | |

| | | mg/kg as received basis | | | | | | | | |
|---|---|---|---|---|---|---|---|---|---|---|
| | | Na | K | Fe | Ca | Mg | V | Si | P | S |
| 3 | Black Liquor | 61900 | 5310 | 8 | 35 | 35 | <1 | 100 | 15 | 22400 |

| | | mg/kg as received basis | | | | | | | |
|---|---|---|---|---|---|---|---|---|---|
| | | Ni | Mn | Cr | Cu | Se | Zn | Ba | As | Al |
| 3 | Black Liquor | <1 | 26 | 1 | <1 | <1 | 2 | 1 | <1 | 8 |

TABLE 40

Biocrude Comparison

| | Wt %, dry basis | | | | | GCV dry basis | Wt %, dry ash free basis | | | | | GCV daf basis |
|---|---|---|---|---|---|---|---|---|---|---|---|---|
| Description | Ash | C | H | N | S | O | MJ/kg | C | H | N | S | O | MJ/kg |
| Hog fuel + catalyst | 6.2 | 76.7 | 7.2 | 0.3 | 0.1 | 9.5 | 33.9 | 81.8 | 7.7 | 0.3 | 0.1 | 10.2 | 36.1 |
| Hog fuel + Black liquor | 2.8 | 70.6 | 7.3 | 0.3 | 0.7 | 18.3 | 32.6 | 72.6 | 7.5 | 0.3 | 0.7 | 18.9 | 33.5 |
| Mixed feed + Black liquor 1 | 2.4 | 73.3 | 7.2 | 0.4 | 0.7 | 16.1 | 33.0 | 75.1 | 7.4 | 0.4 | 0.7 | 16.5 | 33.8 |
| Mixed feed + Black liquor 2 | 2.0 | 74.5 | 7.3 | 0.3 | 0.7 | 15.3 | 33.0 | 76.0 | 7.4 | 0.3 | 0.7 | 15.6 | 33.7 |
| Radiata pine biocrude - typical | 0.8 | 78.3 | 7.0 | 0.1 | 0.02 | 13.8 | 34.0 | 78.9 | 7.1 | 0.1 | 0.02 | 13.9 | 34.3 |
| Radiata Pine + Black liquor biocrude | 0.4 | 79.0 | 7.3 | 0.2 | 0.7 | 13.0 | 34.3 | 79.3 | 7.3 | 0.2 | 0.7 | 12.5 | 34.4 |

TABLE 41

Biocrude Comparison - Ash

| | | % oxide in ash | | | | | | | | | |
|---|---|---|---|---|---|---|---|---|---|---|---|
| Run # | Sample Description | SiO2 | Al2O3 | Fe2O3 | TiO2 | K2O | MgO | Na2O | CaO | SO3 | P2O5 |
| 1 | SPF wood biocrude | — | — | — | — | — | — | — | — | — | — |
| 2 | Black liquor biocrude #1 | 3.6 | 4.4 | 5.6 | 0.08 | 1.4 | 1.7 | 13.1 | 3.2 | 19.1 | 0.60 |
| 3 | Black liquor biocrude #2 | 5.4 | 3.9 | 2.5 | 0.07 | 3.7 | 2.0 | 27.9 | 3.7 | 38.0 | 0.51 |

TABLE 41-continued

| | | Biocrude Comparison - Ash | | | | | | | | |
|---|---|---|---|---|---|---|---|---|---|---|
| 4 | Paper sludge oily product | 10.4 | 0.82 | 1.8 | 0.14 | 0.06 | 8.6 | 3.0 | 73.5 | 0.48 0.34 |
| 5 | Hog fuel + catalyst | 0.8 | 1.7 | 1.4 | 0.05 | 0.34 | 3.7 | 7.2 | 46.6 | 1.1 2.459 |
| 6 | Hog fuel + Black liquor | 3 | 3.7 | 9.9 | 0.13 | 0.44 | 3.7 | 3.6 | 36.2 | 24.3 3.55 |
| 7 | Mixed feed + Black liquor 1 | | | | | | | | | |
| 8 | Mixed feed + Black liquor 2 | | | | | | | | | |
| | Radiata pine biocrude | 36.10 | 13.10 | 11.60 | 0.80 | 1.30 | 3.60 | 7.90 | 11.70 | 1.60 1.70 |

| | | % oxide in ash | | | | | | | | |
|---|---|---|---|---|---|---|---|---|---|---|
| Run # | Sample Description | BaO | SrO | CuO | MnO | Cr2O3 | ZnO | V2O5 | Co3O4 | NiO |
| 1 | SPF wood biocrude | — | — | — | — | — | — | — | — | — |
| 2 | Black liquor biocrude #1 | 0.04 | <0.01 | 0.36 | 0.24 | 0.16 | 0.20 | 0.52 | 0.00 | 0.04 |
| 3 | Black liquor biocrude #2 | 0.04 | 0.00 | 0.32 | 0.32 | 0.07 | 0.16 | 0.09 | 0.00 | 0.05 |
| 4 | Paper sludge oily product | 0.07 | 0.07 | 0.03 | 0.38 | 0.03 | 0.04 | <0.01 | <0.01 | 0.01 |
| 5 | Hog fuel + catalyst | 1.17 | 0.17 | 0.4 | 0.31 | 0.11 | 0.02 | 0 | 0.02 | 0 |
| 6 | Hog fuel + Black liquor | 1.39 | 0.17 | 0.5 | 0.56 | 0.17 | 0.02 | 0 | 0.02 | 0 |
| 7 | Mixed feed + Black liquor 1 | | | | | | | | | |
| 8 | Mixed feed + Black liquor 2 | | | | | | | | | |
| | Radiata pine biocrude | 0.21 | 0.05 | | 0.42 | | 0.18 | 0.07 | | |

Example 2: Processing of Feedstocks into Bio-Oil Products Using Black Liquor Additive Materials and Methods
Feedstock Properties of the feedstock and the ash composition of the feedstock are shown in Table 41 and Table 42, respectively.

TABLE 41

Proximate and ultimate analysis of feedstock

| Feedstock | Hog fuel | Lignin | Black Liquor | Tall Oil Soap |
|---|---|---|---|---|
| Moisture % ar | 8.1 | 41 | 80.2 | 37.2 |
| Ash Yield % db at 550° C. | 13.5 | 3.8 | 67.5 | 15 |
| Volatile Matter % db | 68.9 | 69.3 | 53.9 | 90.8 |
| Fixed carbon % db | 17.6 | 26.9 | <0.1 | <0.1 |
| Carbon % db | 46.5 | 65.2 | 10.3 | 47.9 |
| Hydrogen % db | 5.5 | 5.7 | 7.6 | 9.7 |
| Nitrogen % db | 0.32 | 0.06 | <0.01 | <0.01 |
| Sulphur % db | 0.03 | 2.3 | 0.7 | 0.2 |
| Chlorine % db | 0.03 | 0.03 | 0.06 | <0.01 |
| Oxygen (by difference) % db | 34.2 | 22.9 | 14.6 | 27.4 |
| Calorific Value MJ/kg | | | | |
| Gross Dry | 18.6 | 26.5 | | |
| Gross Wet | 17.1 | 15.7 | | |
| Net Wet | 15.8 | 14 | | |

Notes to table: ar—as received, db—dry basis

TABLE 42

Ash composition of the feedstock

| Feedstock | Hog fuel | Lignin | Black Liquor | Tall Oil Soap |
|---|---|---|---|---|
| | % ash analysis | | | |
| $SiO_2$ | 72.5 | 0.5 | 1 | 0.6 |
| $Al_2O_3$ | 6.7 | 0.9 | 0.1 | <0.1 |
| $Fe_2O_3$ | 5.6 | 0.5 | 0.2 | 0.1 |
| $TiO_2$ | 0.38 | 0.02 | <0.01 | <0.01 |
| $K_2O$ | 2.8 | 3.1 | 3.3 | 3.2 |
| MgO | 1.3 | 0.3 | <0.1 | 0.1 |
| $Na_2O$ | 1.3 | 42.8 | 44.2 | 49.3 |
| CaO | 8.4 | 0.5 | 0.1 | 1.7 |

TABLE 42-continued

Ash composition of the feedstock

| Feedstock | Hog fuel | Lignin | Black Liquor | Tall Oil Soap |
|---|---|---|---|---|
| $SO_3$ | 0.1 | 50.3 | 2 | 1.6 |
| $P_2O_5$ | 0.61 | 0.01 | 0.02 | 0.4 |
| NiO | 0.01 | <0.01 | <0.01 | <0.01 |
| BaO | 0.17 | 0.01 | <0.01 | 0.01 |
| SrO | 0.03 | <0.01 | <0.01 | <0.01 |
| CuO | 0.01 | <0.01 | <0.01 | <0.01 |
| MnO | 0.26 | 0.12 | 0.01 | 0.14 |
| $Cr_2O_3$ | 0.04 | <0.01 | <0.01 | <0.01 |
| ZnO | 0.06 | 0.06 | <0.01 | 0.05 |
| $V_2O_5$ | 0.01 | <0.01 | <0.01 | <0.01 |
| $Co_3O_4$ | 0.01 | <0.01 | <0.01 | <0.01 |
| LOI @ 550 to 650° C. | | | 35.7 | 12 |
| Total | 100.3 | 99.3 | | |

The hog fuel feedstock was ground using modified compressed air jet mills to a particle size of less than about 150 microns to suit the pump valve orifices of the pilot plant pump. The pilot plant pump requires a greater degree of comminution of the feedstock than would a commercial facility. Black liquor samples were homogenized as necessary before use to remove agglomerates that could potentially cause pumping difficulties in use. The feedstock analysis in Table 41 for the hog fuel is after grinding. The grinding process reduces the moisture content of the hog fuel.

Run Conditions

Feedstock conversion according to the invention was carried out using a continuous flow process in a pilot plant reactor. The reactor is schematically represented in FIG. 2. Catalyst injection additional to the catalysts in the black liquor was not used in example runs 9-14.

The conditions for the runs in the pilot plant are summarized in Table 43.

TABLE 43

Feedstock and run conditions

| | Feed in Slurry tank | | | | | | | |
|---|---|---|---|---|---|---|---|---|
| Run No. | Hog Fuel % db | Lignin % db | Black Liquor % db | Tall oil soap % db | Methanol % | Pressure Bar | Temperature ° C. | Residence time Minutes |
| 9 | 5.2 | | 5.2 | | | 240 | 347 | 25 |
| 10 | 5.2 | | 5.2 | | | 240 | 360 | 25 |
| 11 | 7.4 | | 2.9 | 0.7 | 0.2 | 240 | 370 | 25 |
| 12 | 8.1 | | 3.2 | 0.8 | 0.2 | 240 | 355 | 25 |
| 13 | 6.6 | | 2.6 | 0.6 | 0.2 | 240 | 320 | 25 |
| 14 | 6.4 | 2.5 | | 0.6 | 0.2 | 240 | 360 | 25 |

Results

After depressurization and cooling of products to ambient temperature the products were separated into the following phases: gas and vapour phase; biocrude oil phase, aqueous phase.

Due to the high ash content of the hog fuel feedstock, the biocrude oil was further separated for the purpose of analysis into acetone-soluble and acetone-insoluble components. Table 44 shows the properties of the biocrude oil phase. Table 45 shows the properties of the gas/vapour phase.

TABLE 44 properties of the biocrude oil phase

| Run no. | Fraction | Fraction | GCV (MJ/kg) | C | H | N | S | O | ash |
|---|---|---|---|---|---|---|---|---|---|
| 9 | Acetone soluble | 0.82 | 32.157 | 73.9 | 7 | 0.18 | 0.0835 | 16.5 | 2.4 |
| 9 | Acet. Insoluble | 0.18 | 17.266 | 21.4 | 2.1 | 0.11 | 0.0193 | 4.7 | 71.7 |
| 10 | Acetone soluble | 0.83 | 32.677 | | | | | | |
| 10 | Acet. Insoluble | 0.17 | 8.833 | | | | | | |
| 11 | Acetone soluble | 0.78 | 34.198 | 75.6 | 7.8 | 0.29 | 0.0564 | 15.6 | 0.7 |
| 11 | Acet. Insoluble | 0.22 | 9.430 | 33.2 | 2.5 | 0.07 | 0.0518 | 11.3 | 52.9 |
| 12 | Acetone soluble | | | | | | | | |
| 12 | Acet. Insoluble | | | | | | | | |
| 13 | Acetone soluble | 0.80 | 33.437 | | | | | | |
| 13 | Acet. Insoluble | 0.20 | 9.915 | | | | | | |
| 14 | Acetone soluble | | | | | | | | |
| 14 | Acet. Insoluble | | | | | | | | |

Note:
% Oxygen by difference

TABLE 45 gas and vapour composition, volume %, corrected for dilution by nitrogen and oxygen

| Run No | Hydrogen | Carbon Dioxide | Carbon Monoxide | Methane | Ethane | Propane | Butane | Pentane | Hydrogen Sulfide | Carbonyl Sulfide | Methyl Mercaptan |
|---|---|---|---|---|---|---|---|---|---|---|---|
| 9 | 27.37 | 43.80 | | 7.30 | 1.42 | 0.69 | 0.51 | 0.25 | 0.76 | 0.047 | 11.132 |
| 10 | 31.21 | 45.99 | | 8.21 | 1.74 | 0.76 | 0.46 | 0.26 | 0.47 | 0.021 | 5.650 |
| 11 | 8.73 | 84.91 | | 3.54 | 0.64 | 0.41 | 0.32 | 0.17 | 0.15 | 0.005 | 0.671 |
| 12 | 4.92 | 90.28 | | 2.13 | 0.38 | 0.28 | 0.26 | 0.15 | 0.19 | | 0.881 |
| 13 | 2.52 | 94.61 | | 0.88 | 0.12 | 0.10 | 0.15 | 0.08 | 0.19 | | 1.143 |
| 14 | | | | | | | | | | | |

| Run No | Ethyl Mercaptan | Dimethyl Sulfide | n-Propyl mercaptan | Ethylmethyl sulfide | Dimethyl Disulphide | Carbon Disulphide | Dimethyl Trisulphide | Thiophene |
|---|---|---|---|---|---|---|---|---|
| 9 | 0.128 | 5.511 | 0.034 | 0.029 | 0.818 | 0.142 | 0.019 | 0.037 |
| 10 | 0.090 | 3.942 | 0.039 | 0.043 | 1.022 | 0.049 | 0.019 | 0.037 |
| 11 | 0.054 | 0.145 | 0.007 | 0.009 | 0.239 | 0.010 | 0.000 | 0.000 |
| 12 | 0.052 | 0.149 | | 0.009 | 0.307 | 0.010 | 0.000 | 0.000 |
| 13 | 0.022 | 0.060 | | | 0.108 | 0.007 | 0.000 | 0.000 |
| 14 | | | | | | | | |

Product Distribution—Gas Yields

TABLE 46

Gas yields from run examples as percentage of total dry mass of feed

| Run # | Gas Yield mass % of total dry feed* |
|---|---|
| 9 | 8.5% |
| 10 | 10.9% |
| 11 | 13.0% |
| 12 | 9.7% |
| 13 | 7.8% |
| 14 | 8.7% |

Note:
*Gas density of 1.5 kg/m$^3$ assumed for mass fraction calculations

The invention claimed is:

1. A method for producing a bio-product from organic matter feedstock, the method comprising:
   providing a reaction mixture comprising the organic matter feedstock, a solvent, and black pulping liquor (black liquor), wherein the black liquor was generated independently of the organic matter feedstock,
   treating the reaction mixture in a reactor vessel at a reaction temperature of between about 300° C. and about 400° C. and a reaction pressure of between about 180 bar and about 350 bar to thereby convert all or a portion of the organic matter feedstock into a product mixture comprising the bio-product; and
   depressurising and cooling the product mixture;
   wherein the reaction mixture and product mixture move in continuous flow through the reactor vessel during said treating.

2. The method of claim 1, wherein the organic matter feedstock comprises or consists of:
   (i) lignite feedstock;
   (ii) lignocellulosic feedstock; or
   (iii) a mixture of lignocellulosic and lignite feedstock.

3. The method of claim 1, wherein the organic matter feedstock comprises or consists of lignocellulosic feedstock.

4. The method of claim 1, wherein the black liquor comprises:
   (i) between about 4 wt % and 10 wt % sodium hydroxide (NaOH), between about 10 wt % and 30 wt % sodium sulfide (Na$_2$S), between about 25 wt % and about 50 wt % sodium carbonate (Na$_2$CO$_3$), between about 5 wt % and about 15 wt % sodium sulfite (Na$_2$SO$_3$), between about 8 wt % and about 20 wt % sodium sulfate (Na$_2$SO$_4$), between about 10 wt % and about 25 wt % sodium thiosulfate (Na$_2$S$_2$O$_3$), and between about 10 wt % and about 90 wt % organic solids or between about 30% and about 70% organic solids; or
   (ii) between about 15 wt % and 25 wt % sodium sulfide (Na$_2$S), between about 25 wt % and about 45 wt % sodium carbonate (Na$_2$CO$_3$), between about 5 wt % and about 15 wt % sodium sulfite (Na$_2$SO$_3$), between about 10 wt % and about 15 wt % sodium sulfate (Na$_2$SO$_4$), between about 13 wt % and about 20 wt % sodium thiosulfate (Na$_2$S$_2$O$_3$), and between about 40 wt % and about 90 wt % organic solids or between about 50% and about 80% organic solids, or between about 60% and about 75% organic solids.

5. The method of claim 1, wherein the reaction mixture further comprises green pulping liquor (green liquor).

6. The method of claim 5, wherein the green liquor comprises:
   (i) between about 4 wt % and 12 wt % sodium hydroxide (NaOH), between about 15 wt % and 25 wt % sodium sulfide (Na$_2$S), between about 50 wt % and about 70 wt % sodium carbonate (Na$_2$CO$_3$), between about 1 wt % and about 7 wt % sodium sulfite (Na$_2$SO$_3$), between about 2 wt % and about 10 wt % sodium sulfate (Na$_2$SO$_4$), and between about 1 wt % and about 5 wt % sodium thiosulfate (Na$_2$S$_2$O$_3$); or
   (ii) between about 5 wt % and 10 wt % sodium hydroxide (NaOH), between about 17 wt % and 23 wt % sodium sulfide (Na$_2$S), between about 55 wt % and about 65 wt % sodium carbonate (Na$_2$CO$_3$), between about 1 wt % and about 4 wt % sodium sulfite (Na$_2$SO$_3$), between about 3 wt % and about 9 wt % sodium sulfate (Na$_2$SO$_4$), and between about 1 wt % and about 5 wt % sodium thiosulfate (Na$_2$S$_2$O$_3$).

7. The method of claim 1, wherein the pulping liquor further comprises white pulping liquor (white liquor).

8. The method of claim 7, wherein the white liquor comprises:
   (i) between about 40 wt % and 65 wt % sodium hydroxide (NaOH), between about 10 wt % and 30 wt % sodium sulfide (Na$_2$S), between about 8 wt % and about 22 wt % sodium carbonate (Na$_2$CO$_3$), between about 1 wt % and about 6 wt % sodium sulfite (Na$_2$SO$_3$), between about 2 wt % and about 10 wt % sodium sulfate (Na$_2$SO$_4$), and between about 1 wt % and about 5 wt % sodium thiosulfate (Na$_2$S$_2$O$_3$), or
   (ii) between about 45 wt % and 60 wt % sodium hydroxide (NaOH), between about 15 wt % and 25 wt % sodium sulfide (Na$_2$S), between about 10 wt % and about 20 wt % sodium carbonate (Na$_2$CO$_3$), between about 2 wt % and about 5 wt % sodium sulfite (Na$_2$SO$_3$), between about 2 wt % and about 7 wt % sodium sulfate (Na$_2$SO$_4$), and between about 1.5 wt % and about 4 wt % sodium thiosulfate (Na$_2$S$_2$O$_3$).

9. The method of claim 1, wherein the treating comprises treating the reaction mixture at a temperature of between 320° C. and 360° C., and a pressure of between 220 bar and 250 bar.

10. The method of claim 1, wherein the method comprises preparing a slurry comprising the organic matter and the pulping liquor, generating subcritical or supercritical steam independently of the slurry, and contacting the slurry with the subcritical or supercritical steam in at least one vessel or chamber of said reactor vessel.

11. The method of claim 1, wherein the reaction mixture comprises between 50% and 95%, between 50% and 95%, between 50% and 90%, between 50% and 80%, between 50% and 70%, between 50% and 60%, between 30% and 90%, between 40% and 90%, between 20% and 75%, between 1% and 30%, between 5% and 30%, between 10% and 30%, between 5% and 30%, between 5% and 20%, between 5% and 15%, between 10% and 30%, between 10% and 30%, between 10% and 15%, less than 20%, less than 30%, less than 25%, less than 15%, less than 10%, or less than 5%, of the pulping liquor by weight.

12. The method of claim 1, wherein the solvent is an aqueous solvent, an oil solvent, or a mixture of an aqueous solvent and an oil solvent, and
   the reaction mixture comprises less than 20%, less than 30%, less than 35%, less than 40%, less than 40%, less than 70%, less than 80%, less than 90%, less than 95%, between 10% and 95%, between 30% and 95%, between 50% to 70%, or between 60% to 80%, of the solvent by weight.

13. The method of claim 1, wherein the aqueous solvent comprises: water, water only, or water and an alcohol.

14. The method of claim 1, wherein the organic matter comprises lignocellulosic feedstock that comprises at least 10% lignin, at least 35% cellulose, and at least 20% hemicellulose.

15. The method of claim 1, wherein the reaction mixture further comprises a solid substrate that is solid or substantially solid at the reaction temperature and pressure, sequesters organic and/or inorganic matter that de-solubilises within the reaction mixture or the product mixture, and/or alters one or more flow characteristics of the reaction mixture and/or the product mixture in the reactor vessel, wherein the solid substrate is chemically inert or substantially chemically inert at the reaction temperature and pressure.

16. The method of claim 15, wherein the solid substrate is present in the reaction mixture at a concentration of more than 0.5%, more than 1%, more than 3%, more than 5%, more than 10%, more than 25%, or more than 30% by weight.

17. The method of claim 1, wherein the reaction mixture further comprises an oil additive, wherein the oil additive is mixed with the feedstock and/or solvent prior to the treating.

18. The method of claim 1, comprising dissolving bio-oil from the bio-product in a purifying solvent and filtering the dissolved bio-oil to remove particulates and solid material.

* * * * *